United States Patent
Puro et al.

(10) Patent No.: US 11,202,828 B2
(45) Date of Patent: Dec. 21, 2021

(54) THERAPEUTIC SIRP-α ANTIBODIES

(71) Applicant: Arch Oncology, Inc., Brisbane, CA (US)

(72) Inventors: Robyn Puro, St. Louis, MO (US); Ronald R. Hiebsch, St. Louis, MO (US); Benjamin J. Capoccia, St. Louis, MO (US); Gabriela Andrejeva, St. Louis, MO (US); Juan C. Almagro, Cambridge, MA (US); Daniel S. Pereira, San Diego, CA (US)

(73) Assignee: Arch Oncology, Inc., Brisbane, CA (US)

( * ) Notice: Subject to any disclaimer, the term of this patent is extended or adjusted under 35 U.S.C. 154(b) by 84 days.

(21) Appl. No.: 16/682,893

(22) Filed: Nov. 13, 2019

(65) Prior Publication Data

US 2020/0297842 A1    Sep. 24, 2020

Related U.S. Application Data

(60) Provisional application No. 62/767,509, filed on Nov. 14, 2018, provisional application No. 62/820,718, filed on Mar. 19, 2019, provisional application No. 62/886,872, filed on Aug. 14, 2019, provisional application No. 62/931,746, filed on Nov. 6, 2019.

(51) Int. Cl.
| | |
|---|---|
| *A61K 39/395* | (2006.01) |
| *A61P 35/00* | (2006.01) |
| *A61K 9/00* | (2006.01) |
| *A61K 45/06* | (2006.01) |
| *C07K 16/28* | (2006.01) |

(52) U.S. Cl.
CPC ........ *A61K 39/3955* (2013.01); *A61K 9/0019* (2013.01); *A61K 39/39558* (2013.01); *A61K 45/06* (2013.01); *A61P 35/00* (2018.01); *C07K 16/2803* (2013.01); *C07K 2317/24* (2013.01); *C07K 2317/31* (2013.01); *C07K 2317/565* (2013.01); *C07K 2317/76* (2013.01)

(58) Field of Classification Search
CPC combination set(s) only.
See application file for complete search history.

(56) References Cited

U.S. PATENT DOCUMENTS

| | | |
|---|---|---|
| 2013/0251733 A1 | 9/2013 | Youd |
| 2014/0271478 A1 | 9/2014 | Nishimura |
| 2014/0302034 A1 | 10/2014 | Bankovich |
| 2014/0314775 A1 | 10/2014 | Bergmann |
| 2018/0312587 A1 | 11/2018 | Van Eenennaam |
| 2020/0087411 A1 | 3/2020 | Kley et al. |

OTHER PUBLICATIONS

Yanagita et al (JCI Insight, 2017, 2:e89140, internet pp. 1-15).*
International Application No. PCT/US2019/061278; International Preliminary Report on Patentability, dated May 25, 2021; 9 pages.
International Application No. PCT/US2019/061278; International Search Report and Written Opinion of the International Searching Authority, dated Apr. 7, 2020; 13 pages.
Ring NG et al., Anti-SIRPα Antibody Immunotherapy Enhances Neutrophil and Macrophage Antitumor Activity, Proc Natl Acad Sci 2017, 114(49), pp. E10578-E10585.
UniprotKB_A0A1V2K656, Uncharacterized protein, Accession No. A0A1V2K656, Last modified: Jun. 7, 2017. [online]. [Retrieved on Feb. 4, 2020] Retrieved from the internet: <URL: https://www.uniport.org/uniport/A0A1V2K656> Protein, and Sequence (159 a.a), the region between amino acid residues 105-116.

* cited by examiner

*Primary Examiner* — Laura B Goddard
(74) *Attorney, Agent, or Firm* — Cooley LLP

(57) ABSTRACT

Anti-SIRPα monoclonal antibodies (anti-SIRPα mAbs), including multispecific SIRPα antibodies, are provided with distinct functional profiles as are related compositions and methods of using anti-SIRPα mAbs as therapeutics for the prevention and treatment of solid and hematological cancers. Also provided are amino acid sequences of exemplary anti-SIRPα monoclonal antibodies.

21 Claims, 24 Drawing Sheets

Specification includes a Sequence Listing.

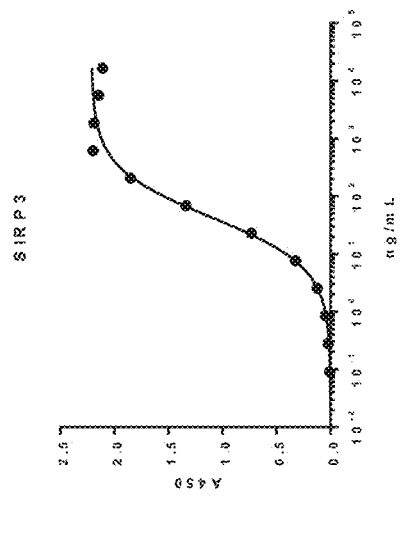
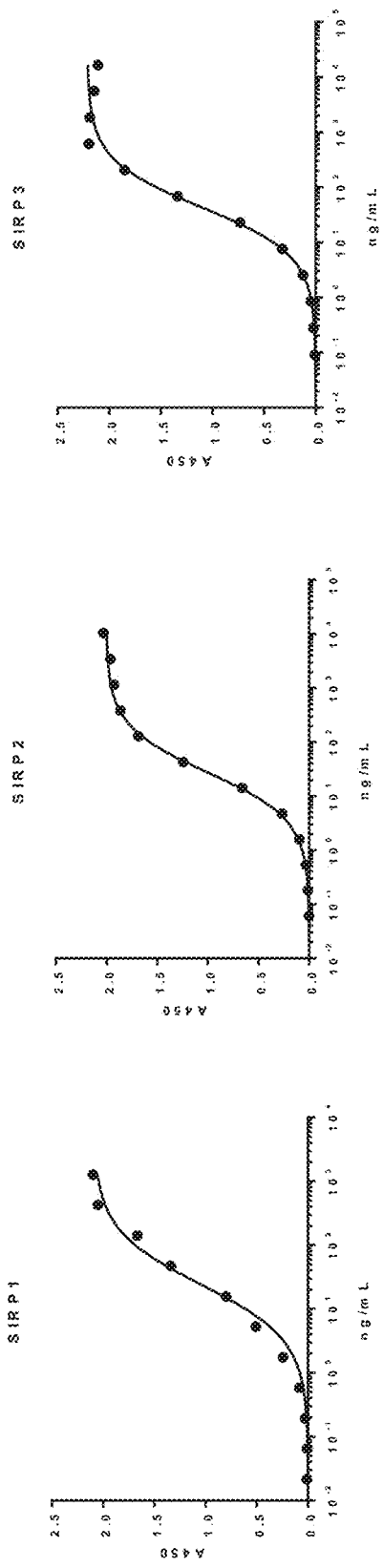
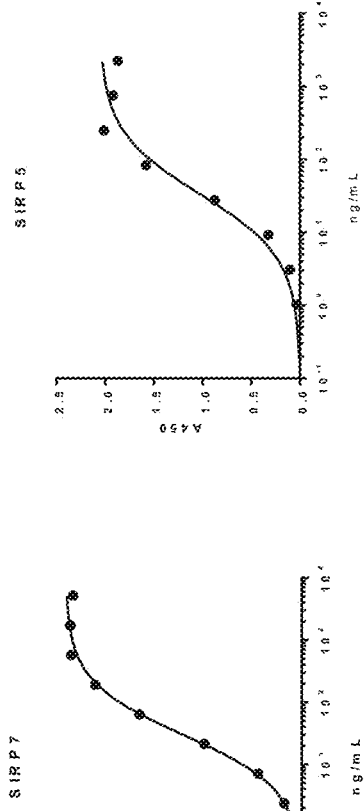
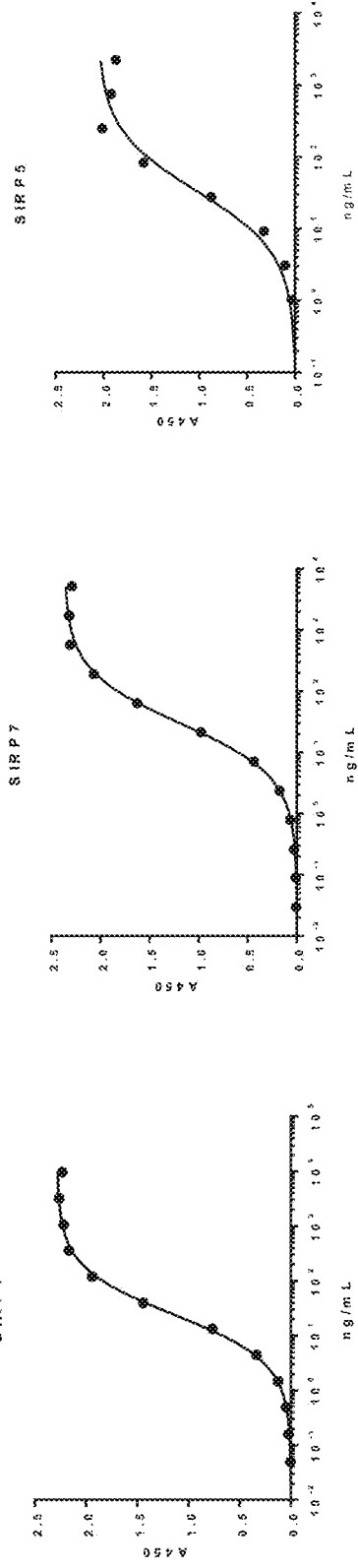
FIG. 1A  FIG. 1B  FIG. 1C
FIG. 1D  FIG. 1E  FIG. 1F

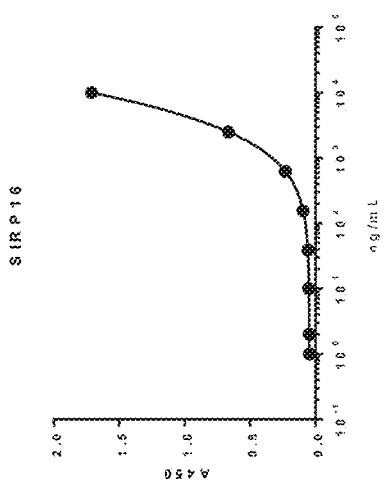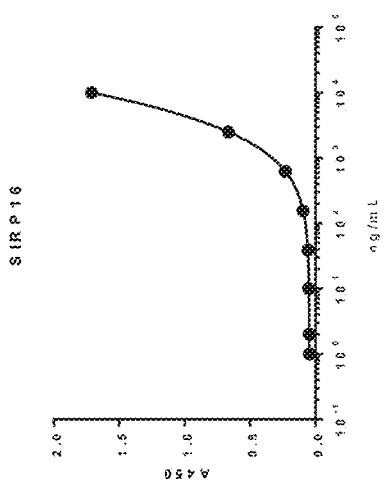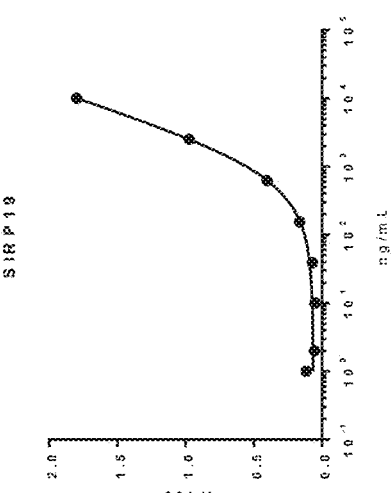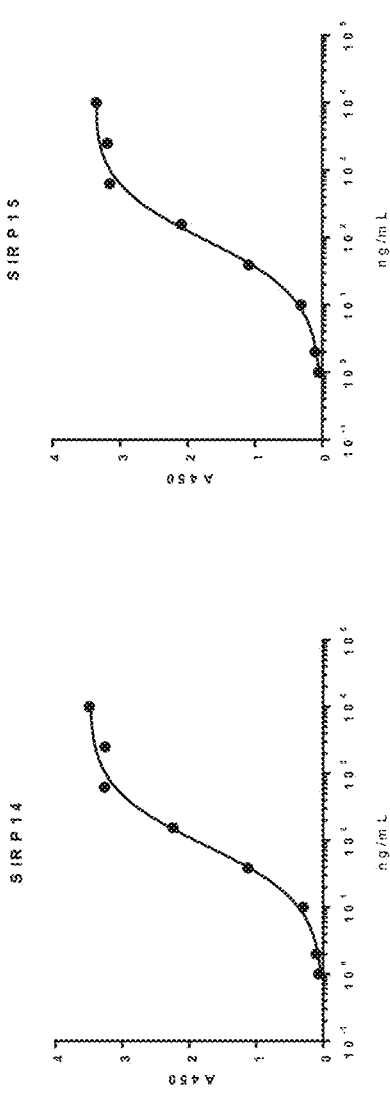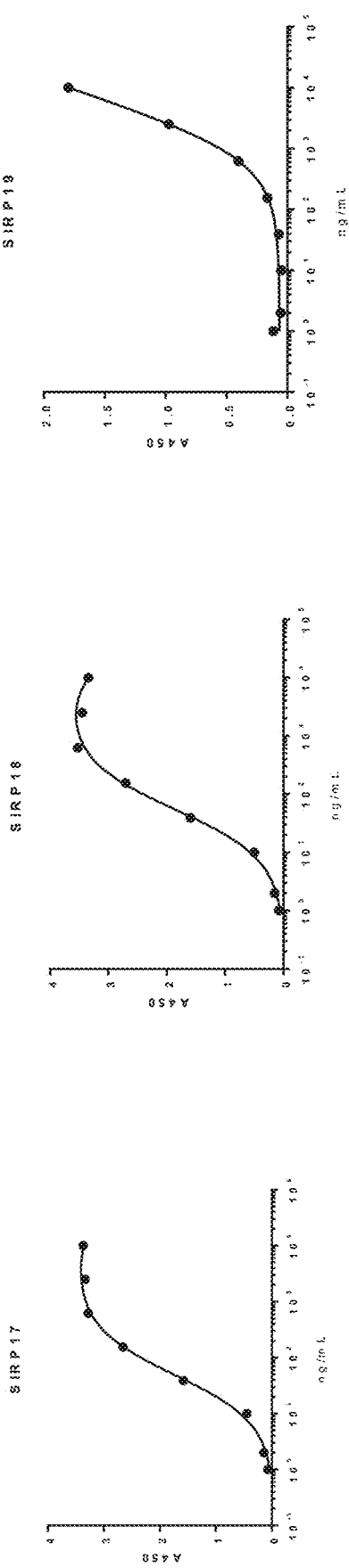

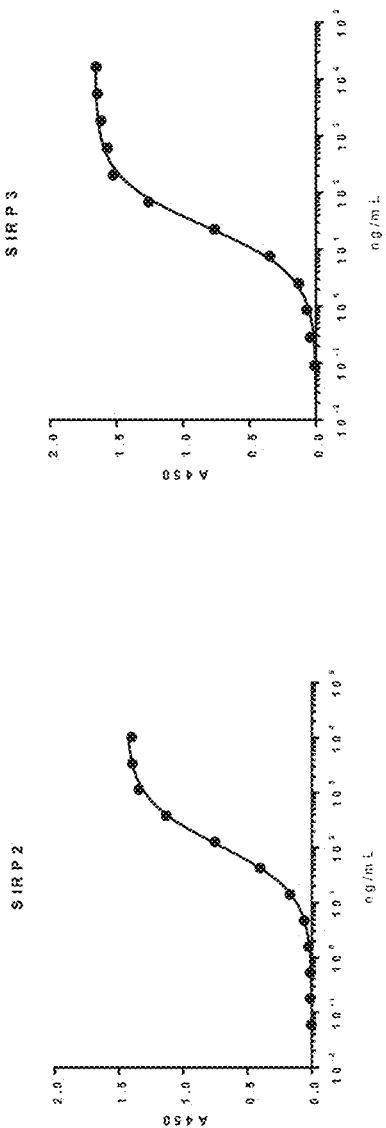
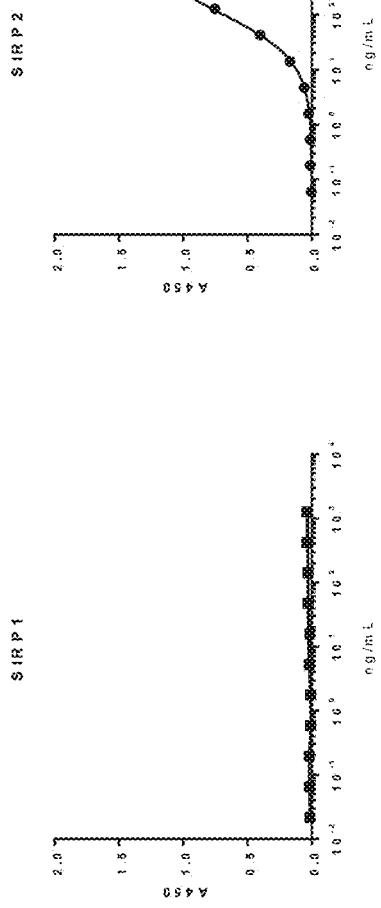
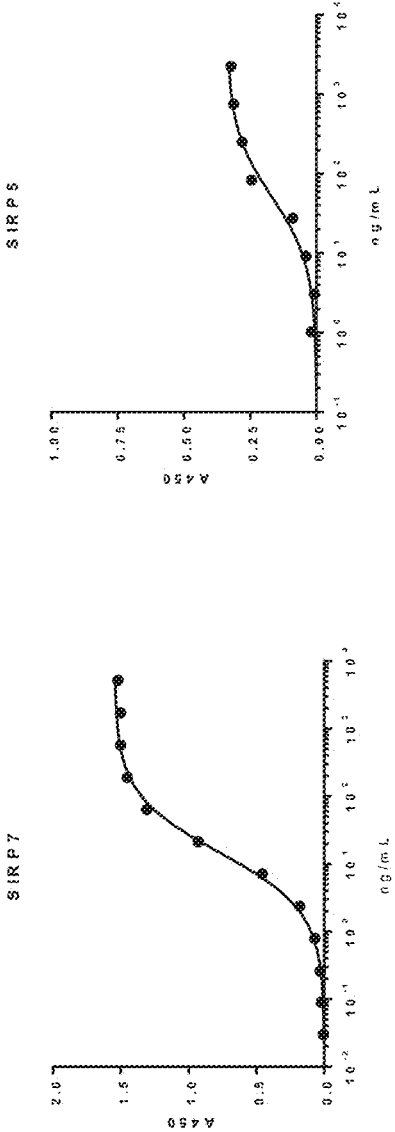
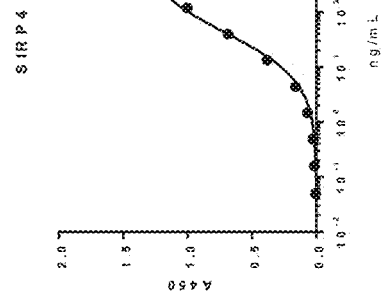

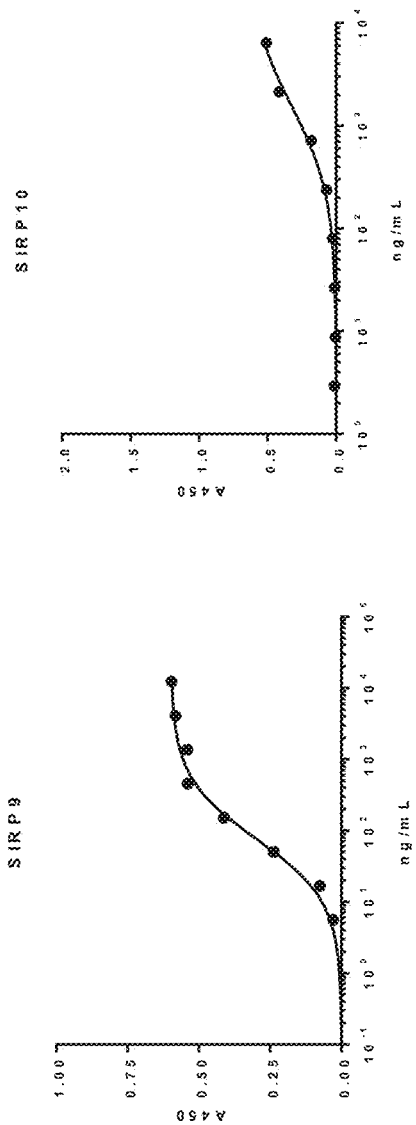
FIG. 3G SIRP8
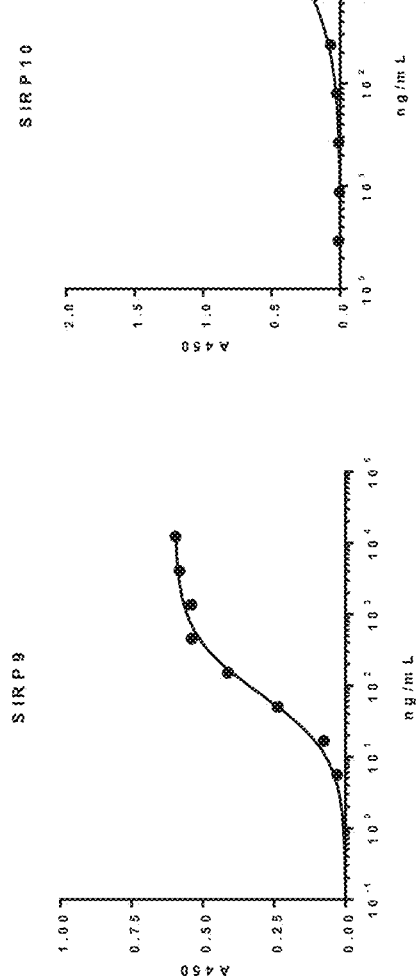
FIG. 3H SIRP9
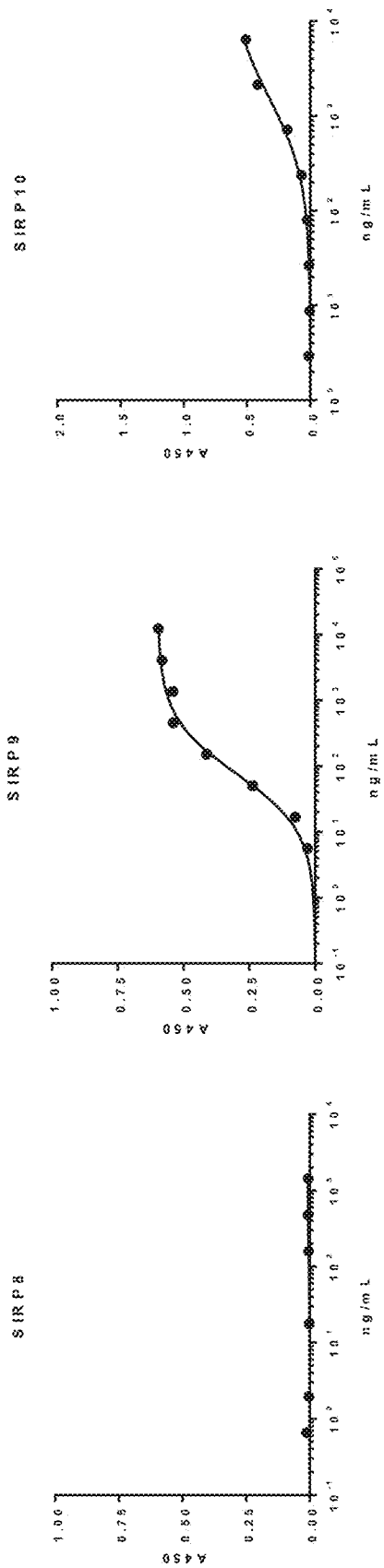
FIG. 3I SIRP10
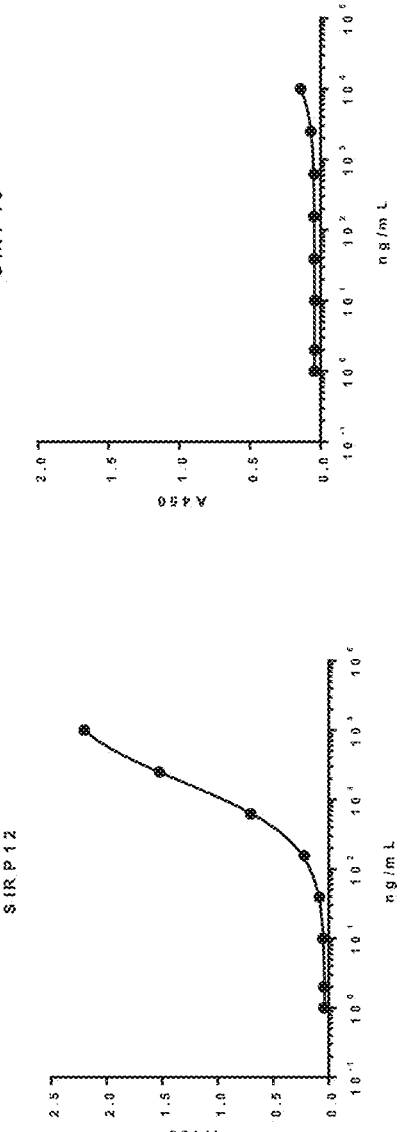
FIG. 3J SIRP11
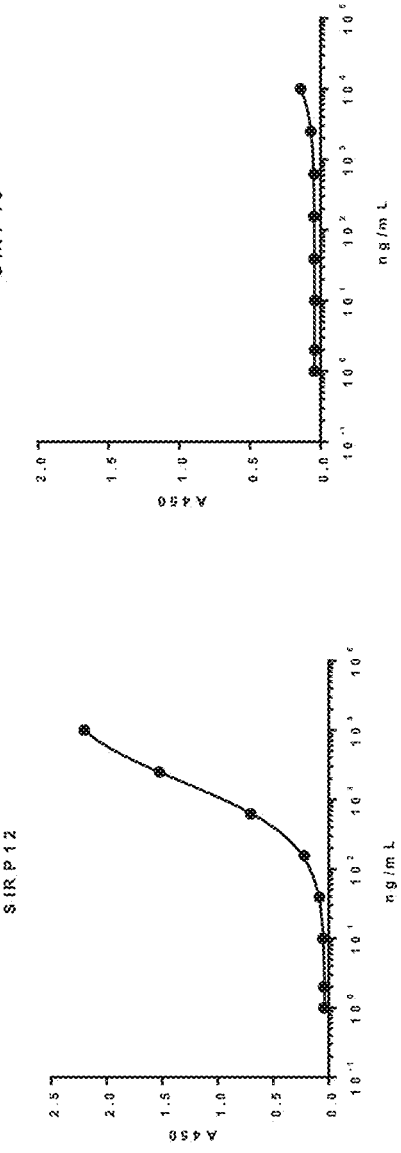
FIG. 3K SIRP12
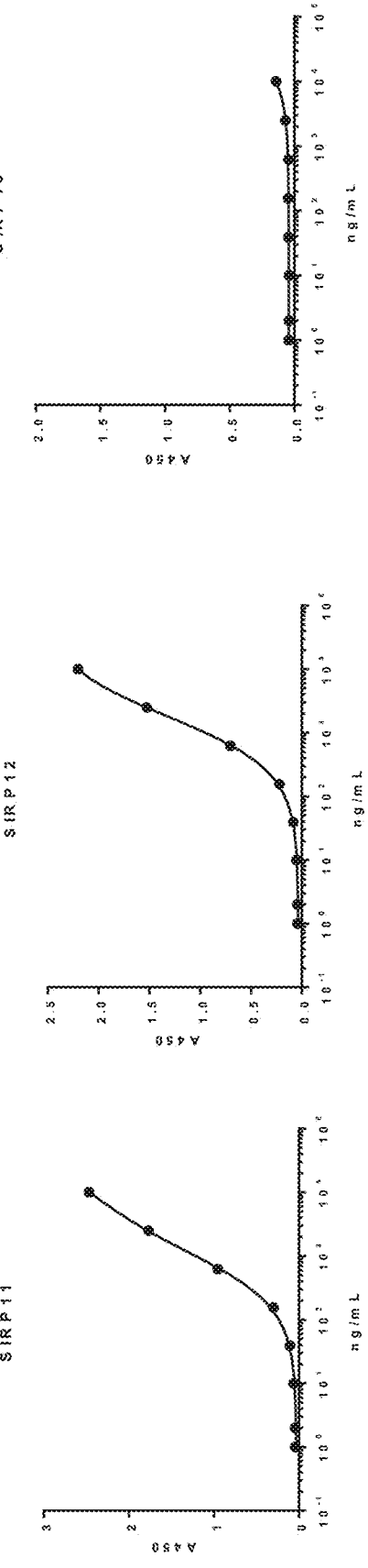
FIG. 3L SIRP13

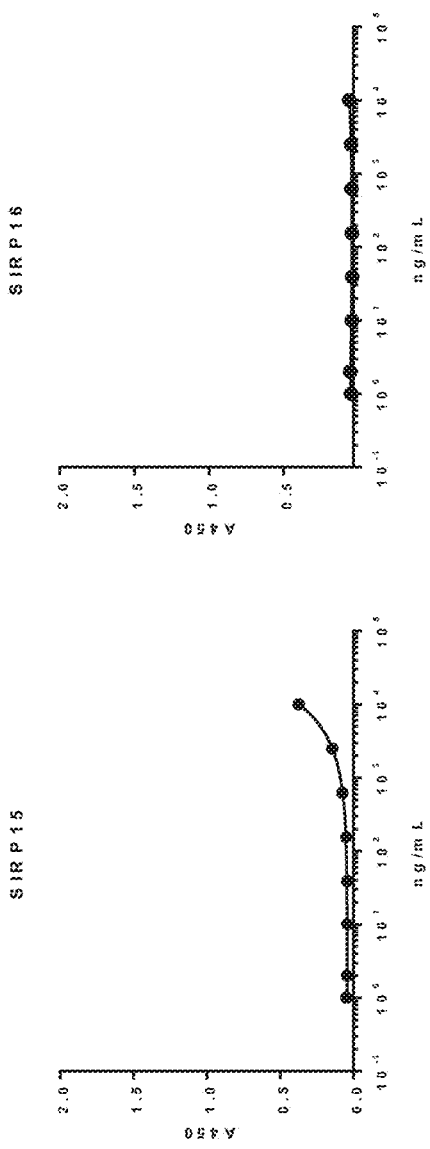
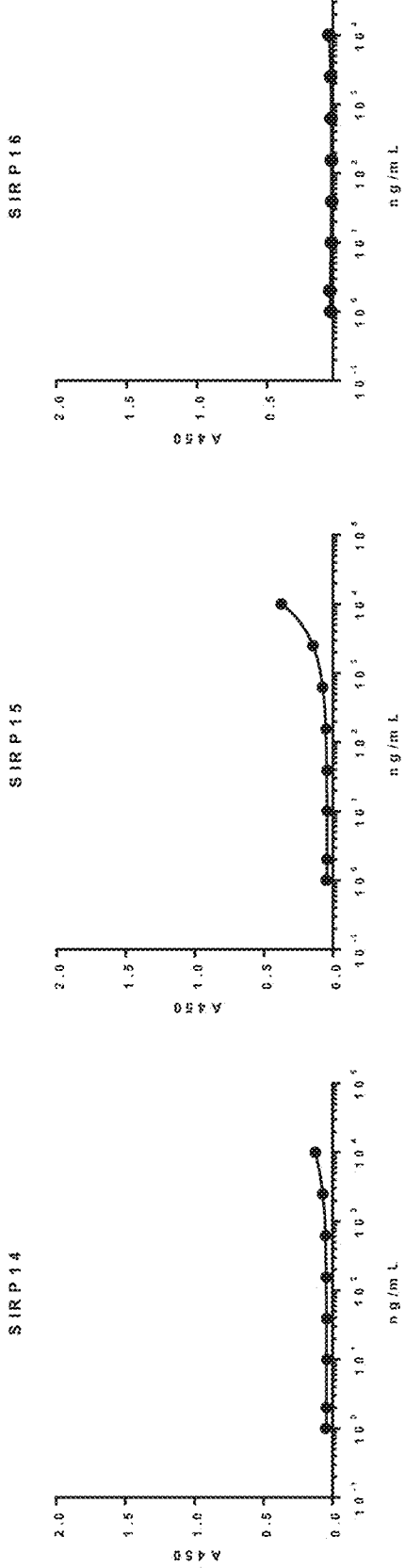
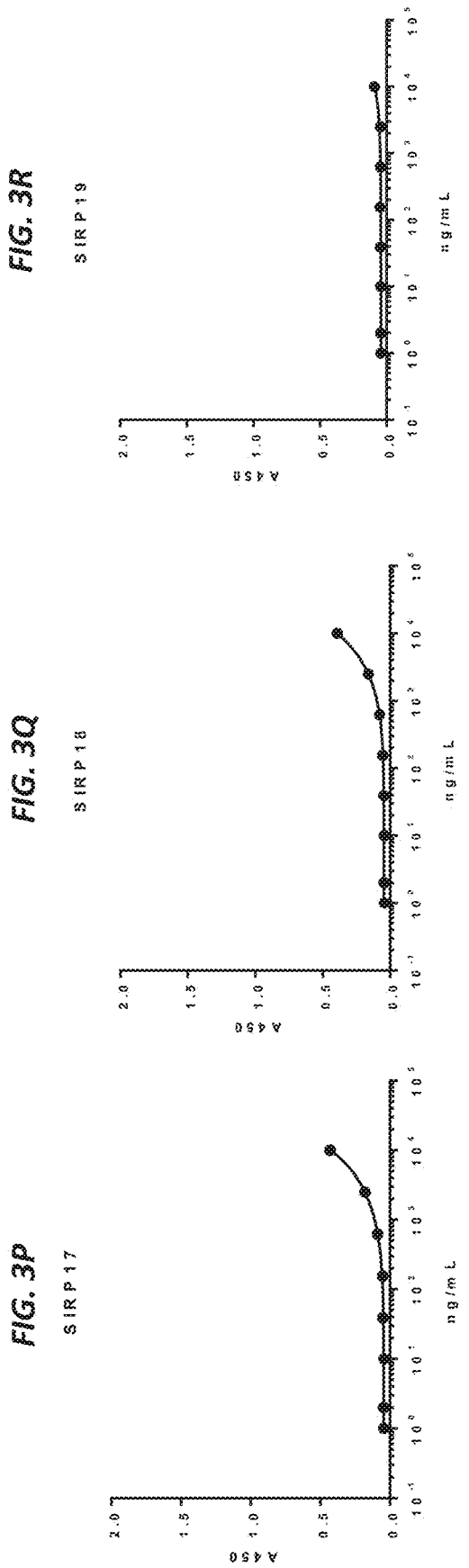
FIG. 3M SIRP14
FIG. 3N SIRP15
FIG. 3O SIRP16
FIG. 3P SIRP17
FIG. 3Q SIRP18
FIG. 3R SIRP19

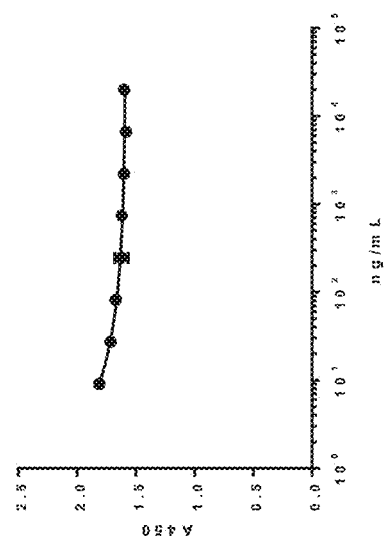
FIG. 5E SIRP7
FIG. 5F SIRP8
FIG. 5G SIRP10

SIRP7

SIRP8

SIRP9

SIRP10

THERAPEUTIC SIRP-α ANTIBODIES

CROSS REFERENCE TO RELATED APPLICATIONS

This application claims the benefit of priority of United States Provisional Application Nos. 62/767,509, filed Nov. 14, 2018, 62/820,718, filed Mar. 19, 2019, 62/886,872, filed Aug. 14, 2019, and 62/931,746, filed Nov. 6, 2019, the disclosures of which are hereby incorporated by reference as if written herein in their entireties.

SEQUENCE LISTING

The instant application contains a Sequence Listing which has been submitted electronically in ASCII format and is hereby incorporated by reference in its entirety. Said ASCII copy, created on Jun. 15, 2020, is named VLX0010-201-US.txt and is 150,083 bytes in size.

FIELD OF THE DISCLOSURE

This disclosure pertains to the field of immunotherapy. The present disclosure provides anti-SIRPα antibodies (anti-SIRPα) which disrupt the interaction between SIRPα and CD47, enhance phagocytosis of tumor cells, cause immunomodulation of immune responses, and methods to generate anti-SIRPα antibodies and use anti-SIRPα antibodies as therapeutic agents for the prevention and treatment of hematological and solid and cancers.

BACKGROUND

Therapeutic antibodies targeting adaptive immunity including the T-cell checkpoints, PD-1, PD-L1 and CTLA-4 to enhance the cytotoxic activity of the T-cell immune response have raised the prospect of long-term remission or even cure for patients with metastatic diseases (Hodi 2010, McDermott 2015). Despite positive results, there remains a significant patient population that either fails to respond to these checkpoint inhibitors (primary resistance) or those that respond, but eventually develop disease progression (acquired resistance) (Pitt 2016, Restifo 2016, Sharma 2017). Recent studies suggest that resistance mechanisms can be both tumor cell intrinsic, including a lack of unique tumor antigen proteins or inhibition of tumor antigen presentation, and tumor cell extrinsic, involving the absence of infiltrating T-cells, redundant inhibitory checkpoints and/or the presence of immunosuppressive cells in the tumor microenvironment (Sharma 2017). Even in tumors considered sensitive to checkpoint inhibitors, or when combining anti-CTLA-4 and anti-PD-1/PDL-1 agents, approximately 50% of patients do not experience tumor shrinkage and the median treatment duration or progression-free survival for all treated patients remains relatively short around 2-5 months (Kazandjian, 2016). In addition, several of the most prevalent solid tumors and the majority of hematological malignancies have shown disappointing results with these checkpoint inhibitors. In particular, hormone receptor-positive breast cancer, colorectal cancer (non-microsatellite instability) and prostate cancer do not appear to be sensitive to this type of immune manipulation and could benefit from a different immunotherapy approach (Le 2015, Dirix 2015, Topalian 2012, Graff 2016). These findings highlight the need for alternative or synergistic approaches that target additional checkpoints to activate the innate immune response in addition to the adaptive immune response to further improve clinical outcomes. Several checkpoints of the innate immune response are present on tumor cells and on myeloid cells (macrophages, dendritic cells, monocyte-derived suppressor cells, granulocytes) which are important cellular components of the tumor microenvironment that influence tumor progression, metastasis and overall outcome (Barclay and van den Berg 2014, Yanagita 2017).

SIgnal Regulatory Protein (SIRP)-α or SIRPα, also known as CD172a, BIT or SHPS-1, is a member of the SIRP paired receptor family of closely related SIRP proteins. SIRPα is expressed mainly by hematopoietic cells, including macrophages, dendritic cells and granulocytes, and is also expressed on neurons, especially in the brain, glia, smooth muscle cells and endothelial and some tumor cells (Barclay and van den Berg 2014). SIPRα is a transmembrane protein with an extracellular domain containing three Ig-like domains and a cytoplasmic region that contains immunoreceptor tyrosine-based inhibitory motifs (ITIMs). The gene encoding human SIRPα is polymorphic with two common variants identified, SIRPαV1 and SIRPαV2, with changes in surface amino acids, but that do not appear to affect binding to its ligand, cluster of differentiation 47 (CD47) (Barclay and van den Berg 2014). The interaction of SIRPα, expressed by myeloid cells, with CD47, expressed or overexpressed on many tumor cells as well as on normal cells, is an important immune checkpoint of the innate response that regulates myeloid functions that include adhesion, migration, activation and inhibitory activities. The CD47/SIRPα interaction regulates macrophage and dendritic cell phagocytosis of target cells sending an inhibitory "don't eat me signal" to the phagocyte. The binding of CD47 to SIRPα initiates an inhibitory signaling cascade resulting in inhibition of phagocytosis following phosphorylation of its cytoplasmic ITIMs (Oldenborg 2000, Oldenborg 2001, Okazawa 2005), recruitment and binding of SHP-1 and SHP-2, Src homology domain-containing protein tyrosine phosphatases (Veillette 1998, Oldenborg 2001), inhibition of non-muscle myosin IIA and ultimately phagocytic function (Tsai and Discher 2008, Barclay and van den Berg 2014, Murata 2014, Veillette and Chen 2018, Matazaki 2009). An important corollary of the action of CD47 as a "don't eat me" signal is its role as a "marker of self". This provides a significant hindrance to phagocytosis of self and blocks a subsequent autoimmune response (Oldenborg, 2002, Oldenborg 2004). Cancer cells use CD47 to mask themselves in "selfness" consequently evading both the innate and adaptive immune systems. Blocking the interaction SIRPα on innate immune cells such as macrophages and dendritic cells with CD47 on tumor cells has emerged as a viable target in cancer therapy. Preclinical data has indicated that, similar to anti-CD47 antibodies, anti-SIRPα antibodies that block the SIRPα/CD47 interaction exhibit anti-tumor efficacy in mouse tumor models, either as monotherapy or in combination with other agents (Gauttier, 2017; Ring, 2017; Yanigita, 2017; Poirier, 2018; and Guattier, 2018). Importantly, generation of an adaptive immune response, in addition to the innate immune response following interruption of the SIRPα/CD47 interaction, appears to be critical to obtaining a robust anti-tumor response (Tseng 2013, Li 2015, Xu 2017).

Expression of SIRPα on DC cells and its interaction with CD47 on T-cells appears to be important in inducing the adaptive immune response. Blockade of the SIRPα/CD47 interaction was reported to affect the DCs ability to stimulate the antigen-specific CD8+ T-cell response and this was correlated with an enhanced DC-mediated response to tumor DNA (Liu 2015, Xu 2017).

Another member of the SIRP family of paired receptors, SIRP-γ, is selectively expressed on the surface of human (but not rodent) T-cells, has a short cytoplasmic region consisting of 4 amino acids. SIRP-γ also binds to CD47 and appears to be important for mediating adhesion between T-cell and APC and for T-cell functions including proliferation and activation (Barclay and van den Berg 2014; and Piccio, 2005). Thus, blocking the interaction between SIRPα and CD47 but not between SIRP-γ and CD47 may provide an advantage to protecting T-cell function.

The present disclosure describes anti-SIRPα mAbs with distinct functional profiles. The antibodies of the disclosure are useful in various therapeutic methods for treating diseases and conditions associated with SIRPα in humans, including using anti-SIRPα mAbs as therapeutics for the prevention and treatment of solid and hematological cancers. The antibodies of the disclosure are also useful as diagnostics to determine the level of anti-SIRPα expression in tissue samples. Embodiments of the disclosure include isolated antibodies and immunologically active binding fragments thereof; pharmaceutical compositions comprising one or more of the anti-SIRPα monoclonal antibodies, preferably chimeric or humanized forms of said antibodies; and methods of therapeutic use of such anti-SIRPα monoclonal antibodies.

The embodiments of the disclosure include the mAbs, or antigen-binding fragments thereof, which are defined by reference to specific structural characteristics, i.e., specified amino acid sequences of either the CDRs or entire heavy and light-chain variable domains or entire heavy- and light-chains. All of these antibodies disclosed herein bind to either SIRPα, SIRPγ, or SIRPα and SIRPγ.

The monoclonal antibodies, or antigen binding fragments thereof may comprise at least one, usually at least three, CDR sequences as provided herein, usually in combination with framework sequences from a human variable region or as an isolated CDR peptide. In some embodiments, an antibody comprises at least one light-chain comprising the three light-chain CDR sequences provided herein situated in a variable region framework, which may be, without limitation, a murine or human variable region framework, and at least one heavy-chain comprising the three heavy-chain CDR sequences provided herein situated in a variable region framework, which may be, without limitation, a human or murine variable region framework.

In some embodiments the combinations of 6 CDRs include, but are not limited to, the combinations of variable heavy-chain CDR1 (HCDR1), variable heavy-chain CDR2 (HCDR2), variable heavy-chain CDR3 (HCDR3), variable light-chain CDR1 (LCDR1), variable light-chain CDR2 (LCDR2), and variable light-chain CDR3 (LCDR3) selected from:

HCDR1 comprising SEQ ID NO:33, HCDR2 comprising SEQ ID NO:34, HCDR3 comprising SEQ ID NO:35, LCDR1 comprising SEQ ID NO:1, LCDR2 comprising SEQ ID NO:2, LCDR3 comprising SEQ ID NO:3;

HCDR1 comprising SEQ ID NO:36, HCDR2 comprising SEQ ID NO:37, HCDR3 comprising SEQ ID NO:38, LCDR1 comprising SEQ ID NO:4, LCDR2 comprising SEQ ID NO:5, LCDR3 comprising SEQ ID NO:6;

HCDR1 comprising SEQ ID NO:39, HCDR2 comprising SEQ ID NO:40, HCDR3 comprising SEQ ID NO:41, LCDR1 comprising SEQ ID NO:7, LCDR2 comprising SEQ ID NO:8, LCDR3 comprising SEQ ID NO:9;

HCDR1 comprising SEQ ID NO:42, HCDR2 comprising SEQ ID NO:43, HCDR3 comprising SEQ ID NO:44, LCDR1 comprising SEQ ID NO:10, LCDR2 comprising SEQ ID NO:11, LCDR3 comprising SEQ ID NO:12;

HCDR1 comprising SEQ ID NO:45, HCDR2 comprising SEQ ID NO:46, HCDR3 comprising SEQ ID NO:47, LCDR1 comprising SEQ ID NO:13, LCDR2 comprising SEQ ID NO:14, LCDR3 comprising SEQ ID NO:15;

HCDR1 comprising SEQ ID NO:48, HCDR2 comprising SEQ ID NO:49, HCDR3 comprising SEQ ID NO:50, LCDR1 comprising SEQ ID NO:16, LCDR2 comprising SEQ ID NO:17, LCDR3 comprising SEQ ID NO:18;

HCDR1 comprising SEQ ID NO:51, HCDR2 comprising SEQ ID NO:52, HCDR3 comprising SEQ ID NO:53, LCDR1 comprising SEQ ID NO:19, LCDR2 comprising SEQ ID NO:20, LCDR3 comprising SEQ ID NO:21.

HCDR1 comprising SEQ ID NO:54, HCDR2 comprising SEQ ID NO:55, HCDR3 comprising SEQ ID NO:56, LCDR1 comprising SEQ ID NO:22, LCDR2 comprising SEQ ID NO:23, LCDR3 comprising SEQ ID NO:24.

HCDR1 comprising SEQ ID NO:57, HCDR2 comprising SEQ ID NO:58, HCDR3 comprising SEQ ID NO:59, LCDR1 comprising SEQ ID NO:25, LCDR2 comprising SEQ ID NO:26, LCDR3 comprising SEQ ID NO:27.

HCDR1 comprising SEQ ID NO:60, HCDR2 comprising SEQ ID NO:61, HCDR3 comprising SEQ ID NO:62, LCDR1 comprising SEQ ID NO:28, LCDR2 comprising SEQ ID NO:29, LCDR3 comprising SEQ ID NO:30.

HCDR1 comprising SEQ ID NO:42, HCDR2 comprising SEQ ID NO:43, HCDR3 comprising SEQ ID NO:44, LCDR1 comprising SEQ ID NO:10, LCDR2 comprising SEQ ID NO:31, LCDR3 comprising SEQ ID NO:12.

HCDR1 comprising SEQ ID NO:42, HCDR2 comprising SEQ ID NO:43, HCDR3 comprising SEQ ID NO:44, LCDR1 comprising SEQ ID NO:10, LCDR2 comprising SEQ ID NO:31, LCDR3 comprising SEQ ID NO:32.

HCDR1 comprising SEQ ID NO:57, HCDR2 comprising SEQ ID NO:58, HCDR3 comprising SEQ ID NO:63, LCDR1 comprising SEQ ID NO:25, LCDR2 comprising SEQ ID NO:26, LCDR3 comprising SEQ ID NO:27.

In some embodiments, the anti-SIRPα antibodies include antibodies or antigen binding fragments thereof, comprising a heavy-chain variable domain ($V_H$) having an amino acid sequence selected from the amino acid sequences of: SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, and SEQ ID NO:97, and amino acid sequences exhibiting at least 85%, 90%, 95%, 97%, 98%, or 99% sequence identity to one of the recited sequences. Alternatively or in addition, anti-SIRPα antibodies, including antibodies or antigen binding fragments thereof, may comprise a light-chain variable domain ($V_L$) having an amino acid sequence selected from the amino acid sequences of SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, and SEQ ID NO:80, and amino acid sequences exhibiting at least 85%, 90%, 95%, 97%, 98%, or 99% sequence identity to one of the recited sequences.

Although all possible pairing of $V_H$ domains and $V_L$ domains selected from the $V_H$ domain and $V_L$ domain sequence groups listed above are permissible, certain combinations of $V_H$ and $V_L$ domains are disclosed. Accordingly, anti-SIRPα antibodies, or antigen binding fragments thereof, are those comprising a combination of a heavy-chain variable domain (V$_H$) and a light-chain variable domain (V$_L$), wherein the combination is selected from:
  i. a heavy chain variable domain comprising the amino acid sequence of SEQ ID NO:81 and a light chain variable domain comprising the amino acid sequence SEQ ID NO:64;
  ii. a heavy chain variable domain comprising the amino acid sequence of SEQ ID NO:82 and a light chain variable domain comprising the amino acid sequence SEQ ID NO:65;
  iii. a heavy chain variable domain comprising the amino acid sequence of SEQ ID NO:83 and a light chain variable domain comprising the amino acid sequence SEQ ID NO:66;
  iv. a heavy chain variable domain comprising the amino acid sequence of SEQ ID NO:84 and a light chain variable domain comprising the amino acid sequence SEQ ID NO:67;
  v. a heavy chain variable domain comprising the amino acid sequence of SEQ ID NO:85 and a light chain variable domain comprising the amino acid sequence SEQ ID NO:68;
  vi. a heavy chain variable domain comprising the amino acid sequence of SEQ ID NO:86 and a light chain variable domain comprising the amino acid sequence SEQ ID NO:69;
  vii. a heavy chain variable domain comprising the amino acid sequence of SEQ ID NO:87 and a light chain variable domain comprising the amino acid sequence SEQ ID NO:70;
  viii. a heavy chain variable domain comprising the amino acid sequence of SEQ ID NO:88 and a light chain variable domain comprising the amino acid sequence SEQ ID NO:71;
  ix. a heavy chain variable domain comprising the amino acid sequence of SEQ ID NO:89 and a light chain variable domain comprising the amino acid sequence SEQ ID NO:72;
  x. a heavy chain variable domain comprising the amino acid sequence of SEQ ID NO:90 and a light chain variable domain comprising the amino acid sequence SEQ ID NO:73;
  xi. a heavy chain variable domain comprising the amino acid sequence of SEQ ID NO:91 and a light chain variable domain comprising the amino acid sequence SEQ ID NO:74;
  xii. a heavy chain variable domain comprising the amino acid sequence of SEQ ID NO:91 and a light chain variable domain comprising the amino acid sequence SEQ ID NO:75;
  xiii. a heavy chain variable domain comprising the amino acid sequence of SEQ ID NO:91 and a light chain variable domain comprising the amino acid sequence SEQ ID NO:76;
  xiv. a heavy chain variable domain comprising the amino acid sequence of SEQ ID NO:92 and a light chain variable domain comprising the amino acid sequence SEQ ID NO:74;
  xv. a heavy chain variable domain comprising the amino acid sequence of SEQ ID NO:92 and a light chain variable domain comprising the amino acid sequence SEQ ID NO:75;
  xvi. a heavy chain variable domain comprising the amino acid sequence of SEQ ID NO:92 and a light chain variable domain comprising the amino acid sequence SEQ ID NO:76;
  xvii. a heavy chain variable domain comprising the amino acid sequence of SEQ ID NO:93 and a light chain variable domain comprising the amino acid sequence SEQ ID NO:74;
  xviii. a heavy chain variable domain comprising the amino acid sequence of SEQ ID NO:93 and a light chain variable domain comprising the amino acid sequence SEQ ID NO:75;
  xix. a heavy chain variable domain comprising the amino acid sequence of SEQ ID NO:93 and a light chain variable domain comprising the amino acid sequence SEQ ID NO:76;
  xx. a heavy chain variable domain comprising the amino acid sequence of SEQ ID NO:94 and a light chain variable domain comprising the amino acid sequence SEQ ID NO:74;
  xxi. a heavy chain variable domain comprising the amino acid sequence of SEQ ID NO:94 and a light chain variable domain comprising the amino acid sequence SEQ ID NO:75;
  xxii. a heavy chain variable domain comprising the amino acid sequence of SEQ ID NO:94 and a light chain variable domain comprising the amino acid sequence SEQ ID NO:76;
  xxiii. a heavy chain variable domain comprising the amino acid sequence of SEQ ID NO:84 and a light chain variable domain comprising the amino acid sequence SEQ ID NO:77;
  xxiv. a heavy chain variable domain comprising the amino acid sequence of SEQ ID NO:95 and a light chain variable domain comprising the amino acid sequence SEQ ID NO:78;
  xxv. a heavy chain variable domain comprising the amino acid sequence of SEQ ID NO:95 and a light chain variable domain comprising the amino acid sequence SEQ ID NO:79;
  xxvi. a heavy chain variable domain comprising the amino acid sequence of SEQ ID NO:95 and a light chain variable domain comprising the amino acid sequence SEQ ID NO:80;
  xxvii. a heavy chain variable domain comprising the amino acid sequence of SEQ ID NO:96 and a light chain variable domain comprising the amino acid sequence SEQ ID NO:78;
  xxviii. a heavy chain variable domain comprising the amino acid sequence of SEQ ID NO:96 and a light chain variable domain comprising the amino acid sequence SEQ ID NO:79;
  xxix. a heavy chain variable domain comprising the amino acid sequence of SEQ ID NO:96 and a light chain variable domain comprising the amino acid sequence SEQ ID NO:80;
  xxx. a heavy chain variable domain comprising the amino acid sequence of SEQ ID NO:97 and a light chain variable domain comprising the amino acid sequence SEQ ID NO:78;
  xxxi. a heavy chain variable domain comprising the amino acid sequence of SEQ ID NO:97 and a light chain variable domain comprising the amino acid sequence SEQ ID NO:79;
  xxxii. a heavy chain variable domain comprising the amino acid sequence of SEQ ID NO:97 and a light chain variable domain comprising the amino acid sequence SEQ ID NO:80; and xxxiii. a heavy chain variable domain comprising the amino acid sequence of SEQ ID NO:89 and a light chain variable domain comprising the amino acid sequence SEQ ID NO:72.

In some embodiments, the anti-SIRPα antibodies or antigen binding fragments thereof may also comprise a combination of a heavy-chain variable domain and a light-chain variable domain wherein the heavy-chain variable domain comprises a $V_H$ sequence with at least 85% sequence identity, or at least 90% sequence identity, or at least 95% sequence identity, or at least 97%, 98% or 99% sequence identity, to the heavy chain amino acid sequences shown above in (i) to (xxxiii) and/or the light chain variable domain comprises a $V_L$ sequence with at least 85% sequence identity, or at least 90% sequence identity, or at least 95% sequence identity, or at least 97%, 98% or 99% sequence identity, to the light-chain amino acid sequences shown above in (i) to (xxxiii). The specific $V_H$ and $V_L$ pairings or combinations in parts (i) through (xxxiii) may be preserved for anti-SIRPα antibodies having $V_H$ and $V_L$ domain sequences with a particular percentage sequence identity to these reference sequences.

For all embodiments the heavy-chain and/or light-chain variable domains of the antibodies or antigen binding fragments are defined by a particular percentage sequence identity to a reference sequence, the $V_H$ and/or $V_L$ domains may retain identical CDR sequences to those present in the reference sequence such that the variation is present only within the framework regions.

In another embodiment, the anti-SIRPα antibodies, or antigen binding fragments thereof, are those comprising a combination of a heavy chain (HC) and a light chain (LC), wherein the combination is selected from:

i. a heavy chain comprising the amino acid sequence of SEQ ID NO:109 and a light chain comprising the amino acid sequence SEQ ID NO:98;
ii. a heavy chain comprising the amino acid sequence of SEQ ID NO:110 and a light chain comprising the amino acid sequence SEQ ID NO:99;
iii. a heavy chain comprising the amino acid sequence of SEQ ID NO:111 and a light chain comprising the amino acid sequence SEQ ID NO:100.
iv. a heavy chain comprising the amino acid sequence of SEQ ID NO:112 and a light chain comprising the amino acid sequence SEQ ID NO:101;
v. a heavy chain comprising the amino acid sequence of SEQ ID NO:112 and a light chain comprising the amino acid sequence SEQ ID NO:102;
vi. a heavy chain comprising the amino acid sequence of SEQ ID NO:112 and a light chain comprising the amino acid sequence SEQ ID NO:103;
vii. a heavy chain comprising the amino acid sequence of SEQ ID NO:113 and a light chain comprising the amino acid sequence SEQ ID NO:101;
viii. a heavy chain comprising the amino acid sequence of SEQ ID NO:113 and a light chain comprising the amino acid sequence SEQ ID NO:102;
ix. a heavy chain comprising the amino acid sequence of SEQ ID NO:113 and a light chain comprising the amino acid sequence SEQ ID NO:103;
x. a heavy chain comprising the amino acid sequence of SEQ ID NO:114 and a light chain comprising the amino acid sequence SEQ ID NO:101;
xi. a heavy chain comprising the amino acid sequence of SEQ ID NO:114 and a light chain comprising the amino acid sequence SEQ ID NO:102;
xii. a heavy chain comprising the amino acid sequence of SEQ ID NO:114 and a light chain comprising the amino acid sequence SEQ ID NO:103;
xiii. a heavy chain comprising the amino acid sequence of SEQ ID NO:115 and a light chain comprising the amino acid sequence SEQ ID NO:101;
xiv. a heavy chain comprising the amino acid sequence of SEQ ID NO:115 and a light chain comprising the amino acid sequence SEQ ID NO:102;
xv. a heavy chain comprising the amino acid sequence of SEQ ID NO:115 and a light chain comprising the amino acid sequence SEQ ID NO:103;
xvi. a heavy chain comprising the amino acid sequence of SEQ ID NO:116 and a light chain comprising the amino acid sequence SEQ ID NO:104;
xvii. a heavy chain comprising the amino acid sequence of SEQ ID NO:117 and a light chain comprising the amino acid sequence SEQ ID NO:105;
xviii. a heavy chain comprising the amino acid sequence of SEQ ID NO:117 and a light chain comprising the amino acid sequence SEQ ID NO:106;
xix. a heavy chain comprising the amino acid sequence of SEQ ID NO:117 and a light chain comprising the amino acid sequence SEQ ID NO:107;
xx. a heavy chain comprising the amino acid sequence of SEQ ID NO:118 and a light chain comprising the amino acid sequence SEQ ID NO:105;
xxi. a heavy chain comprising the amino acid sequence of SEQ ID NO:118 and a light chain comprising the amino acid sequence SEQ ID NO:106;
xxii. a heavy chain comprising the amino acid sequence of SEQ ID NO:118 and a light chain comprising the amino acid sequence SEQ ID NO:107;
xxiii. a heavy chain comprising the amino acid sequence of SEQ ID NO:119 and a light chain comprising the amino acid sequence SEQ ID NO:105;
xxiv. a heavy chain comprising the amino acid sequence of SEQ ID NO:119 and a light chain comprising the amino acid sequence SEQ ID NO:106;
xxv. a heavy chain comprising the amino acid sequence of SEQ ID NO:119 and a light chain comprising the amino acid sequence SEQ ID NO:107; and
xxvi. a heavy chain comprising the amino acid sequence of SEQ ID NO:120 and a light chain comprising the amino acid sequence SEQ ID NO:108.

Various forms of the anti-SIRPα mAbs are disclosed. For example, the anti-CD47 mAbs can be full length humanized antibodies with human frameworks and constant regions of the isotypes, IgA, IgD, IgE, IgG, and IgM, more particularly, IgG1, IgG2, IgG3, IgG4, and in some cases with various mutations to alter Fc receptor function or prevent Fab arm exchange or an antibody fragment, e.g., a F(ab')2 fragment, a F(ab) fragment, a single chain Fv fragment (scFv), etc., as disclosed herein.

In some embodiments, the anti-SIRPα mAbs or antigen-binding fragment thereof comprises an IgG isotype selected from IgG1, IgG1-N297Q, IgG2, IgG4, IgG4 S228P, IgG4 PE and variants thereof.

In some embodiments, the anti-SIRPα mAbs or antigen-binding fragment thereof binds human SIRPγ in addition to human SIRPα.

In some embodiments, the anti-SIRPα mAbs or antigen-binding fragment thereof selectively binds human SIRPα.

In some embodiments, the anti-SIRPα mAbs or antigen-binding fragment thereof increases phagocytosis of human tumor cells.

In some embodiments, the anti-SIRPα mAbs as disclosed herein are multispecific antibodies that specifically bind to SIRPα and at least a second antigen, where the second antigen is a marker of a CD47-expressing cell.

In some embodiments, the second antigen of the multispecific antibody is selected from CD19, CD20, CD22, CD24, CD25, CD30, CD33, CD40, CD44, HER2, CD52, CD56, CD70, CD96, CD97, CD99, CD123, CD279 (PD-1), CD117, C-Met, PTHR2, EGFR, RANKL, SLAMF7, PD-L1, CD38, CD19/CD3, HAVCR2 (TIM3), and GD2.

In some embodiments, the anti-SIRPα mAbs or antigen-binding fragment thereof increases phagocytosis of human tumor cells and are administered in combination with an opsonizing monoclonal antibody that targets an antigen on a tumor cell.

In some embodiments, the anti-SIRPα mAbs or antigen-binding fragment thereof increases phagocytosis of human tumor cells and are administered in combination with an opsonizing monoclonal antibody that targets an antigen on a tumor cell, wherein the opsonizing monoclonal antibody is chosen from rituximab (anti-CD20), trastuzumab (anti-HER2), alemtuzumab (anti-CD52), cetuximab (anti-EGFR), panitumumab (anti-EGFR), ofatumumab (anti-CD20), denosumab (anti-RANKL), pertuzumab (anti-HER2), panitumumab (EGFR), pertuzumab (HER2), elotuzumab (SLAMF7), atezolizumab (anti-PD-L1), avelumab (anti-PD-L1), durvalumab (anti-PD-L1), necitumumab (anti-EGFR), daratumumab (anti-CD38), obinutuzumab (anti-CD20), blinatumomab (anti-CD19/CD3), dinutuximab (anti-GD2)

In some embodiments, the opsonizing monoclonal antibody targets CD20, EGFR, and PD-L1.

In some embodiments, the anti-SIRPα mAbs or antigen-binding fragment thereof exhibits anti-tumor activity.

In some embodiments, the anti-SIRPα mAbs or antigen-binding fragment thereof is administered in combination with an anti-CD47 antibody, wherein the anti-CD47 antibody is described in U.S. Pat. No. 10,239,945, and hereby incorporated by reference in its entirety.

In some embodiments, the anti-SIRPα mAbs or antigen-binding fragment thereof is administered in combination with an anti-EGFR antibody.

In some embodiments, the anti-SIRPα mAbs or antigen-binding fragment thereof is administered in combination with an anti-PD-1 antibody.

In some embodiments, the anti-SIRPα mAbs or antigen-binding fragment thereof is administered in combination with an anti-CTLA-4 antibody.

In some embodiments, the disclosure provides a pharmaceutical composition comprising one or more of the anti-SIRPα mAbs or antigen-binding fragments disclosed herein, optionally in chimeric or humanized forms, and a pharmaceutically or physiologically acceptable carrier, diluent, or excipient.

In some embodiments, the anti-SIRPα mAbs or antigen-binding fragment thereof are for use in human therapy.

In some embodiments, the anti-SIRPα mAbs or antigen-binding fragment thereof are for use in preventing or treating cancer in a human patient.

Prior to the present disclosure, there was a need to identify anti-SIRPα mAbs that possess the functional profiles as described herein. The anti-SIRPα mAbs of the present disclosure exhibit a combination of properties that render the mAbs particularly advantageous for use in human therapy, particularly in the prevention and/or treatment of solid and hematological cancers.

In some embodiments, the cancer is selected from leukemia, a lymphoma, multiple myeloma, ovarian cancer, breast cancer, endometrial cancer, colon cancer (colorectal cancer), rectal cancer, bladder cancer, urothelial cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and a sarcoma.

In some embodiments, the leukemia is selected from leukemia is selected from the group consisting of systemic mastocytosis, acute lymphocytic (lymphoblastic) leukemia (ALL), T-cell—ALL, acute myeloid leukemia (AML), myelogenous leukemia, chronic lymphocytic leukemia (CLL), chronic myeloid leukemia (CML), myeloproliferative disorder/neoplasm, myelodysplastic syndrome, monocytic cell leukemia, and plasma cell leukemia; wherein said lymphoma is selected from the group consisting of histiocytic lymphoma and T-cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia; and wherein said sarcoma is selected from the group consisting of osteosarcoma, Ewing's sarcoma, leiomyosarcoma, synovial sarcoma, alveolar soft part sarcoma, angiosarcoma, liposarcoma, fibrosarcoma, rhabdomyosarcoma, and chrondrosarcoma.

In some embodiments, a method is disclosed to assay SIRPα expression in tumor and/or immune cells using an anti-SIRPα monoclonal antibody or antigen-binding fragment thereof, which specifically binds to an epitope within the sequence of SEQ ID NO:121.

In some embodiments, the method comprises obtaining a patient sample, contacting the patient sample with an anti-SIRPα monoclonal antibody or antigen-binding fragment thereof, which specifically binds to an epitope within the sequence of SEQ ID NO:121, and assaying for binding of the antibody to the patient sample, wherein binding of the antibody to the patient sample is diagnostic of SIRPα expression in a patient sample.

In some embodiments, a method is disclosed to assay SIRPγ expression in tumor and or immune cells using an anti-SIRPα monoclonal antibody or antigen-binding fragment thereof, which specifically binds to an epitope within the sequence of SEQ ID NO:122.

In some embodiments, the method comprises obtaining a patient sample, contacting the patient sample with an anti-SIRPγ monoclonal antibody or antigen-binding fragment thereof, which specifically binds to an epitope within the sequence of SEQ ID NO:122, and assaying for binding of the antibody to the patient sample, wherein binding of the antibody to the patient sample is diagnostic of SIRPγ expression in a patient sample.

In some embodiments, the tumor is primary a cancer tumor or a metastatic cancer tumor.

In some embodiments, assaying for binding of the anti-SIRPα monoclonal antibody or antigen-binding fragment thereof to the patient sample utilizes immunohistochemistry labeling of a tissue sample, enzyme linked immunosorbent assay (ELISA), or flow cytometry.

In some embodiments, the method comprises tumor cells, and the assay comprises assaying for the binding of the anti-SIRPα monoclonal antibody or antigen-binding fragment thereof to tumor cells in the patient sample.

Further scope of the applicability of the present disclosure will become apparent from the detailed description provided below. However, it should be understood that the detailed description and specific examples, while indicating embodiments of the disclosure, are given by way of illustration only since various changes and modifications within the spirit and scope of the disclosure will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only and are not limited in the present disclosure.

FIG. 4B. Cells were washed and then incubated with Alexaflour 647-labelled secondary antibody for 1 hr. Cells were washed and antibody binding measured using flow cytometry.

FIG. 5A-FIG. 5G. Blocking of human CD47/SIRPα binding by anti-SIRP antibodies. The ability of anti-SIRP antibodies to block the interaction between CD47 and recombinant human SIRα was determined by solid-phase ELISA. High-binding ELISA plates were coated with recombinant human SIRPα and increasing concentrations of anti-SIRP antibodies were added for 1 hour. Wells were washed and then incubated with an Fc tagged human CD47 for 1 hours. Wells were washed and then incubated with an HRP-labeled secondary antibody for 1 hour followed by addition of peroxidase substrate and the absorbance at 450 nm was measured.

FIG. 7A or 10 µg/ml of the anti-SIRP antibodies, FIG. 7B, were added to the macrophage cultures and incubated at 37° C. for 3 hours. Non-phagocytosed Jurkat cells were removed and macrophage cultures were washed. Macrophages were trypsinized and stained for CD14. Flow cytometry was used to determine the percentage of $CD14^+$/$CFSE^+$ cells in the total $CD14^+$ population.

DETAILED DESCRIPTION OF THE DISCLOSURE

Definitions

Figure 1I:
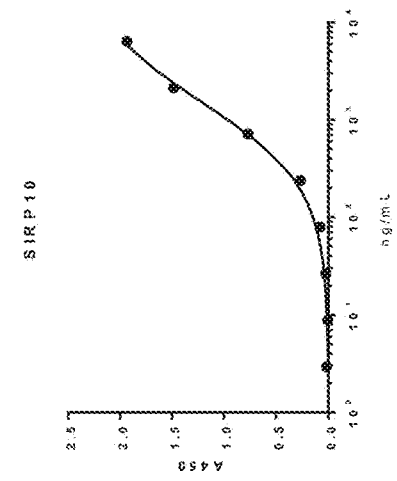
FIG. 1A-FIG. 1V. Binding of anti-SIRP antibodies to human SIRPα. Binding of anti-SIRP antibodies to recombinant human SIRPα was determined by solid-phase ELISA. High-binding ELISA plates were coated with recombinant human SIRPα and increasing concentrations of anti-SIRP antibodies were added for 1 hour. Wells were washed and then incubated with HRP-labeled secondary antibody for 1 hour followed by addition of peroxidase substrate and the absorbance at 450 nm was measured.
Figure 1H:
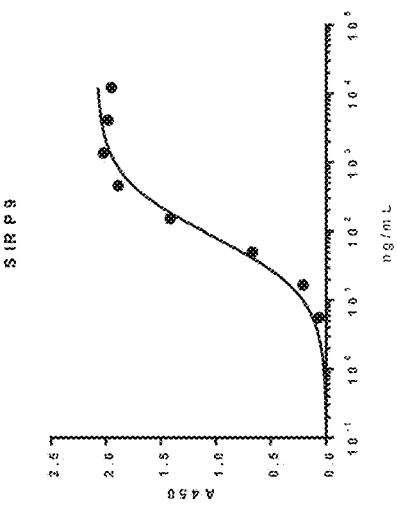
Figure 1G:
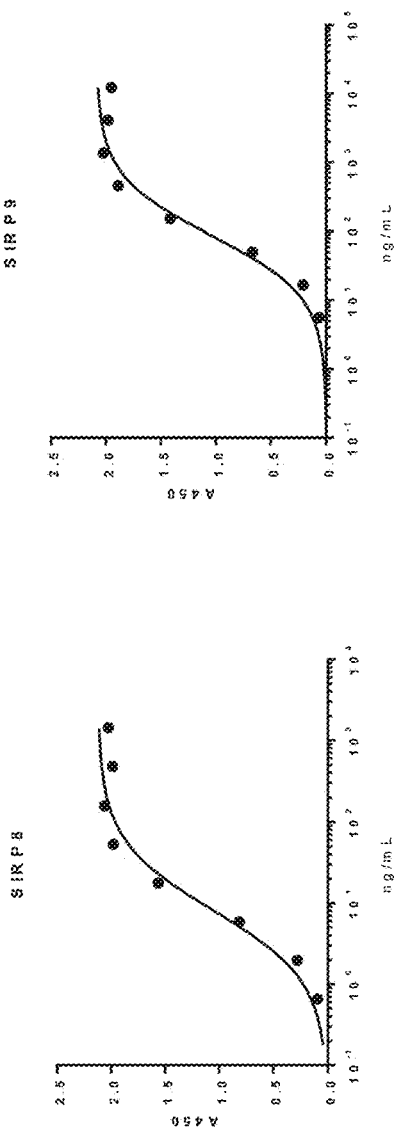
Figure 1L:
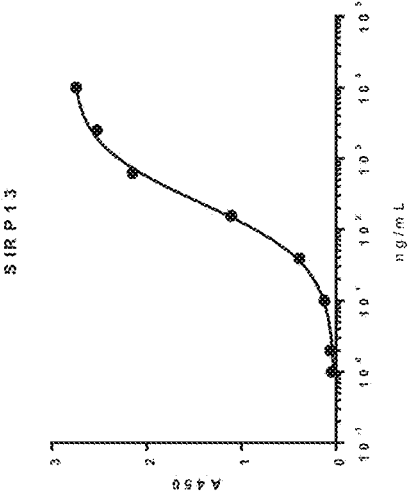
Figure 1K:
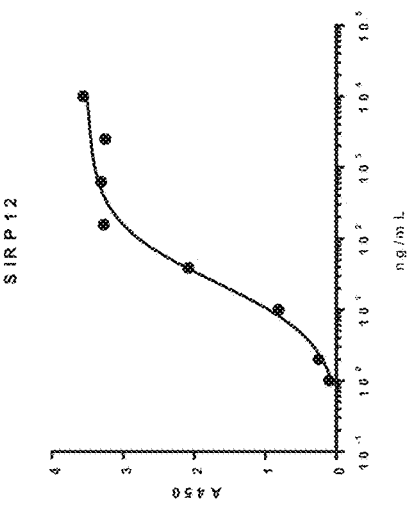
Figure 1J:
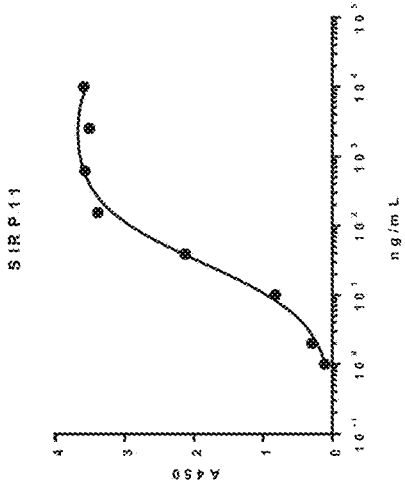
Figure 1S:
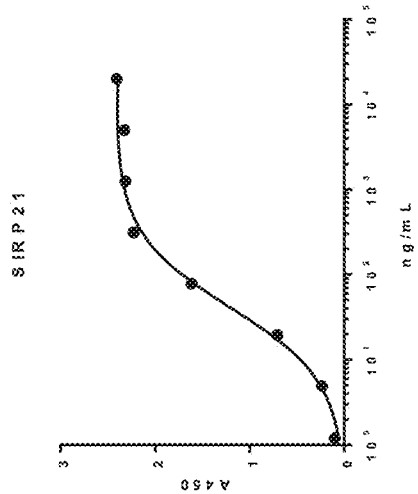
Figure 1T:
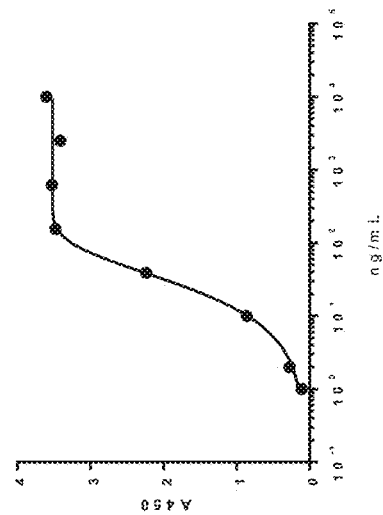
Figure 1U:
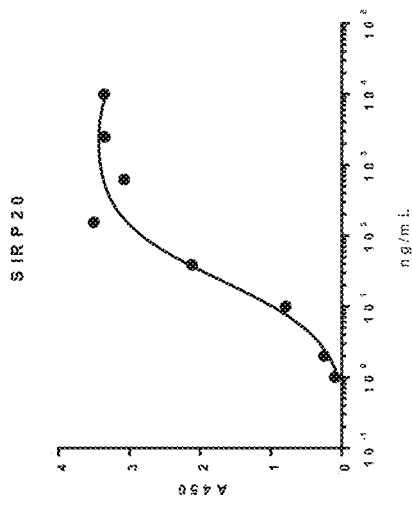

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo or polynucleotide chemistry and hybridization described herein are those well-known and commonly used in the art.

As used herein, the term "SIRPα" and "Src homology 2 (SH2) domain-containing protein tyrosine phosphatase substrate 1 (SHPS-1)" are synonymous and may be used interchangeably.

The term "anti-SIRPα antibody" refer to an antibody of the disclosure which is intended for use as a therapeutic or diagnostic agent, and specifically binds to SIRPα, in particular to a human SIRPα.

The term "anti-SIRP" refer to an antibody of the disclosure which is intended for use as a therapeutic or diagnostic agent, and specifically binds to SIRPα, in particular to a human SIRPα, to one or both of two common variants identified, SIRPαV1 and SIRPαV2, and/or SIRPγ and antibody variants thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts" with or directed against is meant that the antibody reacts with one or more antigenic determinants of the desired antigen and does not react with other polypeptides or binds at a much lower affinity ($K_d > 10^{-6}$ M). Antibodies include but are not limited to, polyclonal, monoclonal, chimeric, Fab fragments, Fab' fragments, F(ab')$_2$ fragments, single chain Fv fragments, and one-armed antibodies.

As used herein, the term "monoclonal antibody (mAb)" as applied to the present anti-SIRPα compounds refer to an antibody that is derived from a single copy or clone including, for example, any eukaryotic, prokaryotic, or phage clone, and not the method by which it is produced. Monoclonal antibodies of the present disclosure preferably exist in a homogeneous or substantially homogeneous population. Complete mAbs contain 2 heavy-chains and 2 light-chains.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multi-specific antibodies formed from antibody fragments.

As disclosed herein, "antibody compounds" refers to mAbs and antigen-binding fragments thereof. Additional antibody compounds exhibiting similar functional properties according to the present disclosure can be generated by conventional methods. For example, mice can be immunized with human SIRPα or fragments thereof, the resulting antibodies can be recovered and purified, and determination of whether they possess binding and functional properties similar to or the same as the antibody compounds disclosed herein can be assessed by the methods disclosed in the Examples. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15.

As disclosed herein, "multispecific antibodies" are e.g., bispecific, trispecific or tetraspecific antibodies. In some embodiments, the multispecific antibodies target SIRPα and/or SIRPγ and at least one other antigen binding specificity in one molecule. In some embodiments, the multispecific antibodies may simultaneously target SIRPα and/or SIRPγ and at least a second antigen (bispecific), or at least a second and third antigen (trispecific), or at least a second, third, and fourth antigen (tetraspecific), wherein the second antigen, third antigen, and fourth antigen is on a tumor cell as disclosed herein.

Bispecific antibodies are antibodies which have two different antigen binding specificities in one molecule. Trispecific antibodies, accordingly, are antibodies which have three different antigen-binding specificities in one molecule. Tetraspecific antibodies are antibodies which have four different antigen-binding specificities in one molecule. In one embodiment, the anti-SIRPα antibodies as disclosed herein are bispecific antibodies targeting SIRPα and/or SIRPγ, and a second antigen on a tumor cell as disclosed herein.

The monoclonal antibodies encompass antibodies in which a portion of the heavy and/or light-chain is identical with, or homologous to, corresponding sequences in murine antibodies, in particular the murine CDRs, while the remainder of the chain(s) is (are) identical with, or homologous to, corresponding sequences in human antibodies. Other embodiments of the disclosure include antigen-binding fragments of these monoclonal antibodies that exhibit binding and biological properties similar or identical to the monoclonal antibodies. The antibodies of the present disclosure can comprise kappa or lambda light-chain constant regions, and heavy-chain IgA, IgD, IgE, IgG, or IgM constant regions, including those of IgG subclasses IgG1, IgG2, IgG3, and IgG4 and in some cases with various mutations to alter Fc receptor function.

The monoclonal antibodies containing the presently disclosed murine CDRs can be prepared by any of the various methods known to those skilled in the art, including recombinant DNA methods.

Reviews of current methods for antibody engineering and improvement can be found, for example, in P. Chames, Ed., (2012) *Antibody Engineering: Methods and Protocols, Second Edition* (*Methods in Molecular Biology, Book* 907), Humana Press, ISBN-10: 1617799734; C. R. Wood, Ed., (2011) *Antibody Drug Discovery* (*Molecular Medicine and Medicinal Chemistry, Book* 4), Imperial College Press; R. Kontermann and S. Dubel, Eds., (2010) *Antibody Engineering Volumes 1 and 2* (Springer Protocols), Second Edition; and W. Strohl and L. Strohl (2012) *Therapeutic antibody engineering: Current and future advances driving the strongest growth area in the pharmaceutical industry*, Woodhead Publishing.

Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15.

A full-length antibody as it exists naturally is a "Y" shaped immunoglobulin (Ig) molecule comprising four polypeptide chains: two identical heavy (H) chains and two identical light (L) chains, interconnected by disulfide bonds. The amino terminal portion of each chain, termed the fragment antigen binding region (FAB), includes a variable region of about 100-110 or more amino acids primarily responsible for antigen recognition via the complementarity determining regions (CDRs) contained therein. The carboxy-terminal portion of each chain defines a constant region (the "Fc" region) primarily responsible for effector function.

The CDRs are interspersed with regions that are more conserved, termed frameworks ("FRs"). Amino acid sequences of many FRs are well known in the art. Each light-chain variable region (LCVR) and heavy-chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light-chain are referred to as "LCDR1, LCDR2, and LCDR3" and the 3 CDRs of the heavy-chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention Kabat et al. (1991) *Sequences of Proteins of Immunological Interest*, Fifth Edition. NIH Publication No. 91-3242.

As described herein, the "antigen-binding site" can also be defined as the "Hypervariable regions", "HVRs", or "HVs", and refer to the structurally hypervariable regions of antibody variable domains as defined by Chothia and Lesk (Chothia and Lesk, *Mol. Biol.* 196:901-917, 1987). There are six HVRs, three in $V_H$ (H1, H2, H3) and three in $V_L$ (L1, L2, L3). CDRs as defined by Kabat were used herein except in H-CDR1, which is extended to include H1.

There are five types of mammalian immunoglobulin (Ig) heavy-chains, denoted by the Greek letters α (alpha), δ (delta), ε (epsilon), γ (gamma), and μ (mu), which define the class or isotype of an antibody as IgA, IgD, IgE, IgG, or IgM, respectively. IgG antibodies can be further divided into subclasses, for example, IgG1, IgG2, IgG3, and IgG4.

Each heavy-chain type is characterized by a particular constant region with a sequence well known in the art. The constant region is identical in all antibodies of the same isotype but differs in antibodies of different isotypes. Heavy-chains γ, α, and δ have a constant region composed of three tandem immunoglobulin (Ig) domains, and a hinge region for added flexibility. Heavy-chains μ and ε have a constant region composed of four Ig domains.

The hinge region is a flexible amino acid stretch that links the Fc and Fab portions of an antibody. This region contains cysteine residues that can form disulfide bonds, connecting two heavy-chains together.

The variable region of the heavy-chain differs in antibodies produced by different B cells but is the same for all antibodies produced by a single B cell or B cell clone. The variable region of each heavy-chain is approximately 110 amino acids long and is composed of a single Ig domain.

In mammals, light-chains are classified as kappa (κ) or lambda (λ), and are characterized by a particular constant region as known in the art. A light-chain has two successive domains: one variable domain at the amino-terminal end, and one constant domain at the carboxy-terminal end. Each antibody contains two light-chains that are always identical; only one type of light-chain, κ or λ, is present per antibody in mammals.

The Fc region, composed of two heavy-chains that contribute three or four constant domains depending on the class of the antibody, plays a role in modulating immune cell activity. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects, including opsonization, cell lysis, and degranulation of mast cells, basophils and eosinophils.

As used herein, the term "epitope" refers to a specific arrangement of amino acids located on a peptide or protein to which an antibody or antibody fragment binds. Epitopes often consist of a chemically active surface grouping of molecules such as amino acids or sugar side chains and have specific three-dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous in the linear sequence.

As used herein, the terms "specifically binds", "bind specifically", "specific binding", and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

As used herein, the term "binding affinity" refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

As used herein, the term "sequence identity" means the percentage of identical nucleotide or amino acid residues at corresponding positions in two or more sequences when the sequences are aligned to maximize sequence matching, i.e., considering gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, Altschul, S. F. et al., *J. Mol. Biol.* 215: 403-410 (1990) and Altschul et al. *Nucl. Acids Res.* 25: 3389-3402 (1997).

One example of an algorithm that is suitable for determining percent sequence identity and sequence similarity is the BLAST algorithm, which is described in (Altschul, S., et al., NCBI NLM NIH Bethesda, Md. 20894; and Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

As used herein, the terms "humanized", "humanization", and the like, refer to grafting of the murine monoclonal antibody CDRs disclosed herein to human FRs and constant regions. Also encompassed by these terms are possible further modifications to the murine CDRs, and human FRs, by the methods disclosed in, for example, Kashmiri et al. (2005) *Methods* 36(1):25-34 and Hou et al. (2008) J. Biochem. 144(1):115-120, respectively, to improve various antibody properties, as discussed below.

As used herein, the term "humanized antibodies" refers to mAbs and antigen binding fragments thereof, including the antibody compounds disclosed herein, that have binding and functional properties according to the disclosure similar to those disclosed herein, and that have FRs and constant regions that are substantially human or fully human surrounding CDRs derived from a non-human antibody.

As used herein, the term "FR" or "framework sequence" refers to any one of FRs 1 to 4. Humanized antibodies and antigen binding fragments encompassed by the present disclosure include molecules wherein any one or more of FRs 1 to 4 is substantially or fully human, i.e., wherein any of the possible combinations of individual substantially or fully human FRs 1 to 4, is present. For example, this includes molecules in which FR1 and FR2, FR1 and FR3, FR1, FR2, and FR3, etc., are substantially or fully human. Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

Fully human frameworks are those that are identical to a known human germline framework sequence. Human FR germline sequences can be obtained from the international ImMunoGeneTics (IMGT) database and from *The Immunoglobulin FactsBook* by Marie-Paule Lefranc and Gerard Lefranc, Academic Press, 2001, the contents of which are herein incorporated by reference in their entirety.

*The Immunoglobulin Facts Book* is a compendium of the human germline immunoglobulin genes that are used to create the human antibody repertoire, and includes entries for 203 genes and 459 alleles, with a total of 837 displayed sequences. The individual entries comprise all the human immunoglobulin constant genes, and germline variable, diversity, and joining genes that have at least one functional or open reading frame allele, and which are localized in the three major loci. For example, germline light-chain FRs can be selected from the group consisting of: IGKV3D-20, IGKV2-30, IGKV2-29, IGKV2-28, IGKV1-27, IGKV3-20, IGKV1-17, IGKV1-16, 1-6, IGKV1-5, IGKV1-12, IGKV1D-16, IGKV2D-28, IGKV2D-29, IGKV3-11, IGKV1-9, IGKV1-39, IGKV1D-39 and IGKV1D-33 and IGKJ1-5 and germline heavy-chain FRs can be selected from the group consisting of: IGHV1-2, IGHV1-18, IGHV1-46, IGHV1-69, IGHV2-5, IGHV2-26, IGHV2-70, IGHV1-3, IGHV1-8, IGHV3-9, IGHV3-11, IGHV3-15, IGHV3-20, IGHV3-66, IGHV3-72, IGHV3-74, IGHV4-31, IGHV3-21, IGHV3-23, IGHV3-30, IGHV3-48, IGHV4-39, IGHV4-59 and IGHV5-51 and IGHJ1-6.

Substantially human FRs are those that have at least 80% sequence identity to a known human germline FR sequence. Preferably, the substantially human frameworks have at least 85%, at least 90%, at least 95%, at least 96%, at least 97%, at least 98%, or at least 99% sequence identity, to a framework sequences disclosed herein, or to a known human germline framework sequence.

CDRs encompassed by the present disclosure include not only those specifically disclosed herein, but also CDR sequences having sequence identities of at least 80%, at least 85%, at least 90%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, or 5 amino acid changes at corresponding positions compared to CDR sequences disclosed herein. Such sequence identical, or amino acid modified, CDRs preferably bind to the antigen recognized by the intact antibody.

Humanized antibodies in addition to those disclosed herein exhibiting similar functional properties according to the present disclosure can be generated using several different methods Almagro et al. *Frontiers in Biosciences.* Humanization of antibodies. (2008) Jan. 1; 13:1619-33. In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. *Bioinformatics.* 2015 Feb. 1; 31(3):434-435 and U.S. Pat. Nos. 4,816,397, 5,225,539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536.

Humanization began with chimerization, a method developed during the first half of the 1980's (Morrison, S. L., M. J. Johnson, L. A. Herzenberg & V. T. Oi: Chimeric human antibody molecules: mouse antigen-binding domains with human constant region domains. *Proc. Natl. Acad. Sci. USA.*, 81, 6851-5 (1984)), consisting of combining the variable (V) domains of murine antibodies with human constant (C) domains to generate molecules with ~70% of human content.

Several different methods can be used to generate humanized antibodies, which are described herein. In one approach, the parent antibody compound CDRs are grafted into a human FR that has a high sequence identity with the parent antibody compound framework. The sequence identity of the new FR will generally be at least 80%, at least 85%, at least 90%, at least 95%, at least 96%, at least 97%, at least 98%, or at least 99% identical to the sequence of the corresponding FR in the parent antibody compound. In the case of FRs having fewer than 100 amino acid residues, one, two, three, four, five, or more amino acid residues can be changed. This grafting may result in a reduction in binding affinity compared to that of the parent antibody. If this is the case, the FR can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. *Bioinformatics.* 2015 Feb. 1; 31(3):434-435 and U.S. Pat. Nos. 4,816,397, 5,225, 539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as described below. When an amino acid falls under the following category, the framework amino acid of the human germ-line sequence that is being used (the "acceptor FR") is replaced by a framework amino acid from a framework of the parent antibody compound (the "donor FR"):

(a) the amino acid in the human FR of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three-dimensional immunoglobulin model.

When each of the amino acids in the human FR of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating humanized antibodies exhibiting similar functional properties to the antibody compounds disclosed herein involves randomly mutating amino acids within the grafted CDRs without changing the framework and screening the resultant molecules for binding affinity and other functional properties that are as good as, or better than, those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific FRs in addition to introducing amino acid changes in the CDRs. This methodology is described in Wu et al. (1999) *J. Mol. Biol.* 294: 151-162.

Applying the teachings of the present disclosure, a person skilled in the art can use common techniques, e.g., site-directed mutagenesis, to substitute amino acids within the presently disclosed CDR and FR sequences and thereby generate further variable region amino acid sequences derived from the present sequences. Up to all naturally occurring amino acids can be introduced at a specific substitution site. The methods disclosed herein can then be used to screen these additional variable region amino acid sequences to identify sequences having the indicated in vivo functions. In this way, further sequences suitable for preparing humanized antibodies and antigen-binding portions thereof in accordance with the present disclosure can be identified. Preferably, amino acid substitution within the frameworks is restricted to one, two, three, four, or five positions within any one or more of the four light-chain and/or heavy-chain FRs disclosed herein. Preferably, amino acid substitution within the CDRs is restricted to one, two, three, four, or five positions within any one or more of the three light-chain and/or heavy-chain CDRs. Combinations of the various changes within these FRs and CDRs described above are also possible.

That the functional properties of the antibody compounds generated by introducing the amino acid modifications discussed above conform to those exhibited by the specific molecules disclosed herein can be confirmed by the methods in Examples disclosed herein.

As described above, to circumvent the problem of eliciting human anti-murine antibody (HAMA) response in patients, murine antibodies have been genetically manipulated to progressively replace their murine content with the amino acid residues present in their human counterparts by grafting their complementarity determining regions (CDRs) onto the variable light ($V_L$) and variable heavy ($V_H$) frameworks of human immunoglobulin molecules, while retaining those murine framework residues deemed essential for the integrity of the antigen-combining site. However, the xenogeneic CDRs of the humanized antibodies may evoke anti-idiotypic (anti-Id) response in patients.

To minimize the anti-Id response, a procedure to humanize xenogeneic antibodies by grafting onto the human frameworks only the CDR residues most crucial in the antibody-ligand interaction, called "SDR grafting", has been developed, wherein only the crucial specificity determining residues (SDRs) of CDRS are grafted onto the human frameworks. This procedure, described in Kashmiri et al. (2005) *Methods* 36(1):25-34, involves identification of SDRs through the help of a database of the three-dimensional structures of the antigen-antibody complexes of known structures, or by mutational analysis of the antibody-combining site. An alternative approach to humanization involving retention of more CDR residues is based on grafting of the 'abbreviated' CDRs, the stretches of CDR residues that include all the SDRs. Kashmiri et al. also discloses a procedure to assess the reactivity of humanized antibodies to sera from patients who had been administered the murine antibody.

Another strategy for constructing human antibody variants with improved immunogenic properties is disclosed in Hou et al. (2008) *J. Biochem.* 144(1):115-120. These authors developed a humanized antibody from 4C8, a murine anti-human CD34 monoclonal antibody, by CDR grafting using a molecular model of 4C8 built by computer-assisted homology modelling. Using this molecular model, the authors identified FR residues of potential importance in antigen binding. A humanized version of 4C8 was generated by transferring these key murine FR residues onto a human antibody framework that was selected based on homology to the murine antibody FR, together with the murine CDR residues. The resulting humanized antibody was shown to possess antigen-binding affinity and specificity similar to that of the original murine antibody, suggesting that it might be an alternative to murine anti-CD34 antibodies routinely used clinically.

Embodiments of the present disclosure encompass antibodies created to avoid recognition by the human immune system containing CDRs disclosed herein in any combinatorial form such that contemplated mAbs can contain the set of CDRs from a single murine mAb disclosed herein, or light and heavy-chains containing sets of CDRs comprising individual CDRs derived from two or three of the disclosed murine mAbs. Such mAbs can be created by standard techniques of molecular biology and screened for desired activities using assays described herein. In this way, the disclosure provides a "mix and match" approach to create novel mAbs comprising a mixture of CDRs from the disclosed murine mAbs to achieve new, or improved, therapeutic activities.

Monoclonal antibodies or antigen-binding fragments thereof encompassed by the present disclosure that "compete" with the molecules disclosed herein are those that bind human SIRPα at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human SIRPα extracellular domain can be bound to a solid support. Then, an antibody compound, or antigen binding fragment thereof, of the present disclosure and a monoclonal antibody or antigen-binding fragment thereof suspected of being able to compete with such disclosure antibody compound are added. One of the two molecules is labeled. If the labeled compound and the unlabeled compound bind to separate and discrete sites on SIRPα, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present disclosure, competing monoclonal antibodies or antigen-binding fragments thereof are those that decrease the binding of the present antibody compounds to SIRPα by about 50%, about 60%, about 70%, about 80%, about 85%, about 86%, about 87%, about 88%, about 89%, about 90%, about 91%, about 92%, about 93%, about 94%, about 95%, about 96%, about 97%, about 98%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Whether mAbs or antigen-binding fragments thereof that compete with antibody compounds of the present disclosure in such competition assays possess the same or similar functional properties of the present antibody compounds can be determined via these methods in conjunction with the methods described in Examples 2-7, below. In various embodiments, competing antibodies for use in the therapeutic methods encompassed herein possess biological activities as described herein in the range of from about 50% to about 100% or about 125%, or more, compared to that of the antibody compounds disclosed herein. In some embodiments, competing antibodies possess about 50%, about 60%, about 70%, about 80%, about 85%, about 90%, about 91%, about 92%, about 93%, about 94%, about 95%, about 96%, about 97%, about 98%, about 99%, or identical biological activity compared to that of the antibody compounds disclosed herein as determined by the methods disclosed in the Examples presented below.

The mAbs or antigen-binding fragments thereof or competing antibodies useful in the compositions and methods can be any of the isotypes described herein. Furthermore, any of these isotypes can comprise further amino acid modifications as follows.

The monoclonal antibody or antigen-binding fragment thereof, or competing antibody described herein can be of the human IgG1 isotype.

The human IgG1 constant region of the monoclonal antibody, antigen-binding fragment thereof, or competing antibody described herein can be modified to alter antibody half-life. Antibody half-life is regulated in large part by Fc-dependent interactions with the neonatal Fc receptor (Roopenian and Alikesh, 2007). The human IgG1 constant region of the monoclonal antibody, antigen-binding fragment thereof, or competing antibody can be modified to increase half-life include, but are not limited to amino acid modifications N434A, T307A/E380A/N434A (Petkova et al., 2006, Yeung et al., 2009); M252Y/S254T/T256E (Dall'Acqua et al., 2006); T250Q/M428L (Hinton et al., 2006); and M428L/N434S (Zalevsky et al., 2010).

As opposed to increasing half-life, there are some circumstances where decreased half-life would be desired, such as to reduce the possibility of adverse events associated with high Antibody-Dependent Cellular Cytotoxicity (ADCC) and Complement-Dependent Cytotoxicity (CDC) antibodies (Presta 2008). The human IgG1 constant region of the monoclonal antibody, antigen-binding fragment thereof, or competing antibody described herein can be modified to decrease half-life and/or decrease endogenous IgG include, but are not limited to, amino acid modifications I253A (Petkova et al., 2006); P257I/N434H, D376V/N434H (Datta-Mannan et al., 2007); and M252Y/S254T/T256E/ H433K/N434F (Vaccaro et al., 2005).

The human IgG1 constant region of the monoclonal antibody, antigen-binding fragment thereof, or competing antibody described herein can be modified to increase or decrease antibody effector functions. These antibody effector functions include, but are not limited to, Antibody-Dependent Cellular Cytotoxicity (ADCC), Complement-Dependent Cytotoxicity (CDC), Antibody-Dependent Cellular Phagocytosis (ADCP), C1q binding, and altered binding to Fc receptors.

The human IgG1 constant region of the monoclonal antibody, antigen-binding fragment thereof, or competing antibody described herein can be modified to increase antibody effector function include, but are not limited to amino acid modifications S298A/E333A/K334 (Shields et al., 2001); S239D/I332E and S239D/A330L/I332E (Lazar et al., 2006); F234L/R292P/Y300L, F234L/R292P/Y300L/ P393L, and F243L/R292P/Y300L/V305I/P396L (Stevenhagen et al., 2007); G236A, G236A/S239D/I332E, and G236A/S239D/A330L/I332E (Richards et al., 2008); K326A/E333A, K326A/E333S and K326W/E333S (Idusogie et al., 2001); S267E and S267E/L328F (Smith et al., 2012); H268F/S324T, S267E/H268F, S267E/S234T, and S267E/H268F/S324T (Moore et al., 2010); S298G/T299A (Sazinsky et al., 2008); E382V/M428I (Jung et al., 2010).

The human IgG1 constant region of the monoclonal antibody, antigen-binding fragment thereof, or competing antibody described herein can be modified to decrease antibody effector function include, but are not limited to amino acid modifications N297A and N297Q (Bolt et al., 1993, Walker et al., 1989); L234A/L235A (Xu et al., 2000); K214T/E233P/L234V/L235A/G236-deleted/A327G/ P331A/D356E/L358M (Ghevaert et al., 2008); C226S/ C229S/E233P/L234V/L235A (McEarchern et al., 2007); S267E/L328F (Chu et al., 2008).

The human IgG1 constant region of the monoclonal antibody, antigen-binding fragment thereof, or competing antibody described herein can be modified to decrease antibody effector function include, but are not limited to amino acid modifications V234A/G237A (Cole et al., 1999); E233D, G237D, P238D, H268Q, H268D, P271G, V309L, A330S, A330R, P331S, H268Q/A330S/V309L/P331S, H268D/A330S/V309L/P331S, H268Q/A330R/V309L/ P331S, H268D/A330R/V309L/P331S, E233D/A330R, E233D/A330S, E233D/P271G/A330R, E233D/P271G/ A330S, G237D/H268D/P271G, G237D/H268Q/P271G, G237D/P271G/A330R, G237D/P271G/A330S, E233D/ H268D/P271G/A330R, E233D/H268Q/P271G/A330R, E233D/H268D/P271G/A330S, E233D/H268Q/P271G/ A330S, G237D/H268D/P271G/A330R, G237D/H268Q/ P271G/A330R, G237D/H268D/P271G/A330S, G237D/ H268Q/P271G/A330S, E233D/G237D/H268D/P271G/ A330R, E233D/G237D/H268Q/P271G/A330R, E233D/ G237D/H268D/P271G/A330S, E233D/G237D/H268Q/ P271G/A330S, P238D/E233D/A330R, P238D/E233D/ A330S, P238D/E233D/P271G/A330R, P238D/E233D/ P271G/A330S, P238D/G237D/H268D/P271G, P238D/ G237D/H268Q/P271G, P238D/G237D/P271G/A330R, P238D/G237D/P271G/A330S, P238D/E233D/H268D/ P271G/A330R, P238D/E233D/H268Q/P271G/A330R, P238D/E233D/H268D/P271G/A330S, P238D/E233D/ H268Q/P271G/A330S, P238D/G237D/H268D/P271G/ A330R, P238D/G237D/H268Q/P271G/A330R, P238D/ G237D/H268D/P271G/A330S, P238D/G237D/H268Q/ P271G/A330S, P238D/E233D/G237D/H268D/P271G/ A330R, P238D/E233D/G237D/H268Q/P271G/A330R, P238D/E233D/G237D/H268D/P271G/A330S, P238D/ E233D/G237D/H268Q/P271G/A330S (An et al., 2009, Mimoto, 2013).

The monoclonal antibody or antigen-binding fragment thereof, or competing antibody described herein can be of the human IgG2 isotype.

The human IgG2 constant region of the monoclonal antibody, antigen-binding fragment thereof, or competing antibody described herein can be modified to increase or decrease antibody effector functions. These antibody effector functions include, but are not limited to, Antibody-Dependent Cellular Cytotoxicity (ADCC), Complement-Dependent Cytotoxicity (CDC), Antibody-Dependent Cellular Phagocytosis (ADCP), and C1q binding, and altered binding to Fc receptors.

The human IgG2 constant region of the monoclonal antibody, antigen-binding fragment thereof, or a competing antibody described herein, can be modified to increase antibody effector function include, but are not limited to, the amino acid modification K326A/E333S (Idusogie et al., 2001).

The human IgG2 constant region of the monoclonal antibody, antigen-binding fragment thereof, or competing antibody described herein can be modified to decrease antibody effector function include, but are not limited to amino acid modifications V234A/G237A (Cole et al., 1999); E233D, G237D, P238D, H268Q, H268D, P271G, V309L, A330S, A330R, P331S, H268Q/A330S/V309L/P331S, H268D/A330S/V309L/P331S, H268Q/A330R/V309L/ P331S, H268D/A330R/V309L/P331S, E233D/A330R, E233D/A330S, E233D/P271G/A330R, E233D/P271G/ A330S, G237D/H268D/P271G, G237D/H268Q/P271G, G237D/P271G/A330R, G237D/P271G/A330S, E233D/ H268D/P271G/A330R, E233D/H268Q/P271G/A330R, E233D/H268D/P271G/A330S, E233D/H268Q/P271G/ A330S, G237D/H268D/P271G/A330R, G237D/H268Q/ P271G/A330R, G237D/H268D/P271G/A330S, G237D/ H268Q/P271G/A330S, E233D/G237D/H268D/P271G/ A330R, E233D/G237D/H268Q/P271G/A330R, E233D/ G237D/H268D/P271G/A330S, E233D/G237D/H268Q/ P271G/A330S, P238D/E233D/A330R, P238D/E233D/ A330S, P238D/E233D/P271G/A330R, P238D/E233D/ P271G/A330S, P238D/G237D/H268D/P271G, P238D/ G237D/H268Q/P271G, P238D/G237D/P271G/A330R, P238D/G237D/P271G/A330S, P238D/E233D/H268D/ P271G/A330R, P238D/E233D/H268Q/P271G/A330R, P238D/E233D/H268D/P271G/A330S, P238D/E233D/ H268Q/P271G/A330S, P238D/G237D/H268D/P271G/ A330R, P238D/G237D/H268Q/P271G/A330R, P238D/ G237D/H268D/P271G/A330S, P238D/G237D/H268Q/ P271G/A330S, P238D/E233D/G237D/H268D/P271G/ A330R, P238D/E233D/G237D/H268Q/P271G/A330R, P238D/E233D/G237D/H268D/P271G/A330S, P238D/ E233D/G237D/H268Q/P271G/A330S (An et al., 2009, Mimoto, 2013).

The Fc region of a human IgG2 of the monoclonal antibody, antigen-binding fragment thereof, or competing antibody described herein can be modified to alter isoform and/or agonistic activity, include, but are not limited to amino acid modifications C127S ($C_{H1}$ domain), C232S, C233S, C232S/C233S, C236S, and C239S (White et al., 2015, Lightle et al., 2010).

The Fc region of a human IgG2 of the monoclonal antibody, antigen-binding fragment thereof, or competing antibody described herein can be modified to exhibit diminished FcγR binding capacity but have conserved FcRn binding. These IgG Fc mutants enable therapeutic targeting of soluble or cell surface antigens while minimizing Fc-associated engagement of immune effector function and complement mediated cytotoxicity. In one embodiment, the IgG2 Fc mutant comprises V234A, G237A, P238S according to the EU numbering system. In another embodiment, the IgG2 Fc mutant comprises V234A, G237A, H268Q, or H268A, V309L, A330S, P331S, according to the EU numbering system. In a particular aspect, the IgG2 Fc mutant comprises V234A, G237A, P238S, H268A, V309L, A330S, P331S, and, optionally, P233S according to the EU numbering system.

The monoclonal antibody or antigen-binding fragment thereof, or competing antibody described herein can be of the human IgG3 isotype.

The human IgG3 constant region of the monoclonal antibody, or antigen binding fragment thereof, wherein said human IgG3 constant region of the monoclonal antibody, or antigen-binding fragment thereof can be modified at one or more amino acid(s) to increase antibody half-life, Antibody-Dependent Cellular Cytotoxicity (ADCC), Complement-Dependent Cytotoxicity (CDC), or apoptosis activity.

The human IgG3 constant region of the monoclonal antibody, or antigen-binding fragment thereof, wherein said human IgG3 constant region of the monoclonal antibody, or antigen-binding fragment thereof can be modified at amino acid R435H to increase antibody half-life.

The monoclonal antibody or antigen-binding fragment thereof, or competing antibody described herein can be of the human IgG4 isotype.

The human IgG4 constant region of the monoclonal antibody, antigen-binding fragment thereof, or competing antibody described herein can be modified to decrease antibody effector functions. These antibody effector functions include, but are not limited to, Antibody-Dependent Cellular Cytotoxicity (ADCC) and Antibody-Dependent Cellular Phagocytosis (ADCP).

The human IgG4 constant region of the monoclonal antibody, antigen-binding fragment thereof, or competing antibody described herein can be modified to prevent Fab arm exchange and/or decrease antibody effector function include, but are not limited to, amino acid modifications F234A/L235A (Alegre et al., 1994); S228P, L235E and S228P/L235E (Reddy et al., 2000).

As used herein, the term "tumor" refers to all neoplastic cell growth and proliferation, whether malignant or benign, and all pre-cancerous and cancerous cells and tissues.

The terms "cancer", "cancerous", and "tumor" are not mutually exclusive as used herein. The terms "cancer" and "cancerous" refer to or describe the physiological condition in mammals that is typically characterized by aberrant cell growth/proliferation. Examples of cancers include, but are not limited to, carcinoma, lymphoma (i.e., Hodgkin's and non-Hodgkin's lymphoma), multiple myeloma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancer.

The term "susceptible cancer" as used herein refers to a cancer, cells of which express CD47, IRPα, or CD47 and SIRPα and are responsive to treatment with an antibody or antigen binding fragment thereof, or competing antibody or antigen binding fragment thereof, from the present disclosure that prevent interaction between CD47 and SIRPα.

The term "autoimmune disease" as used herein refers to when the body's immune system turns against itself and mistakenly attacks healthy cells.

The term "inflammatory disease" as used herein refers to a disease characterized by inflammation which is a fundamental pathologic process consisting of a dynamic complex of histologically apparent cytologic changes, cellular infiltration, and mediator release that occurs in the affected blood vessels and adjacent tissues in response to an injury or abnormal stimulation caused by a physical, chemical, or biologic agent, including the local reactions and resulting morphologic changes; the destruction or removal of the injurious material; and the responses that lead to repair and healing.

The term "autoinflammatory disease" as used herein refers to a disease that results when the innate immune system causes inflammation for unknown reasons.

As used herein, term "treating" or "treat" or "treatment" means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The term "treating" and the like refer to a therapeutic intervention that ameliorates a sign or symptom of a disease or pathological condition after it has begun to develop.

As used herein, term "effective amount" refers to the amount or dose of an antibody compound of the present disclosure which, upon single or multiple dose administration to a patient or organ, provides the desired treatment or prevention.

The precise effective amount for any particular subject will depend upon their size and health, the nature and extent of their condition, and the therapeutics or combination of therapeutics selected for administration. The effective amount for a given patient is determined by routine experimentation and is within the judgment of a clinician. Therapeutically effective amounts of the present antibody compounds can also comprise an amount in the range of from about 0.1 mg/kg to about 150 mg/kg, from about 0.1 mg/kg to about 100 mg/kg, from about 0.1 mg/kg to about 50 mg/kg, or from about 0.05 mg/kg to about 10 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; for example.

A therapeutically effective amount for any individual patient can be determined by the health care provider by monitoring the effect of the antibody compounds on tumor regression, circulating tumor cells, tumor stem cells or anti-tumor responses. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

In some embodiments, antibody compounds of the present disclosure can be used as medicaments in human and veterinary medicine, administered by a variety of routes including, but not limited to, oral, intravenous, intramuscular, intra-arterial, intramedullary, intraperitoneal, intrathecal, intraventricular, transdermal, transcutaneous, topical, subcutaneous, intratumoral, intranasal, enteral, sublingual, intravaginal, intravesicular or rectal routes. The compositions can also be administered directly into a lesion such as a tumor. Dosage treatment may be a single dose schedule or a multiple dose schedule. Hypo sprays may also be used to administer the pharmaceutical compositions. Typically, the therapeutic compositions can be prepared as injectables, either as liquid solutions or suspensions. Solid forms suitable for solution in, or suspension in, liquid vehicles prior to injection can also be prepared. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Such pharmaceutical compositions can be prepared by methods well known in the art. See, e.g., *Remington: The Science and Practice of Pharmacy*, 21$^{st}$ Edition (2005), Lippincott Williams & Wilkins, Philadelphia, Pa., and comprise one or more antibody compounds disclosed herein, and a pharmaceutically acceptable, for example, physiologically acceptable, carrier, diluent, or excipient.

Cancer Indications

Presently disclosed are anti-SIRPα mAbs and antigen binding fragments thereof effective as cancer therapeutics which can be administered to patients, preferably parenterally, with susceptible hematologic cancers and solid tumors including, but not limited to, leukemias, including systemic mastocytosis, acute lymphocytic (lymphoblastic) leukemia (ALL), T-cell—ALL, acute myeloid leukemia (AML), myelogenous leukemia, chronic lymphocytic leukemia (CLL), chronic myeloid leukemia (CIVIL), myeloproliferative disorder/neoplasm, monocytic cell leukemia, and plasma cell leukemia; multiple myeloma (MM); Waldenstrom's Macroglobulinemia; lymphomas, including histiocytic lymphoma and T-cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL; solid tumors, including ovarian cancer, breast cancer, endometrial cancer, colon cancer (colorectal cancer), rectal cancer, bladder cancer, urothelial cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, meduloblastoma, astrocytoma, glioma, meningioma, gastrinoma, neuroblastoma, myelodysplastic syndrome, and sarcomas including, but not limited to, osteosarcoma, Ewing's sarcoma, leiomyosarcoma, synovial sarcoma, alveolar soft part sarcoma, angiosarcoma, liposarcoma, fibrosarcoma, rhabdomyosarcoma, and chrondrosarcoma; and melanoma.

Treatment of Cancer

As is well known to those of ordinary skill in the art, combination therapies are often employed in cancer treatment as single-agent therapies or procedures may not be sufficient to treat or cure the disease or condition. Conventional cancer treatments often involve surgery, radiation treatment, a combination of cytotoxic drugs to achieve additive or synergistic effects, or combinations of any or all of these approaches. Especially useful chemotherapeutic and biologic therapy combinations employ drugs that work via different mechanisms of action, increasing cancer cell control or killing, increasing the ability of the immune system to control cancer cell growth, reducing the likelihood of drug resistance during therapy, and minimizing possible overlapping toxicities by permitting the use of reduced doses of individual drugs.

Classes of conventional anti-tumor and anti-neoplastic agents useful in the combination therapies encompassed by the present methods are disclosed in *Goodman & Gilman's The Pharmacological Basis of Therapeutics*, Twelfth Edition (2010) L. L. Brunton, B. A. Chabner, and B. C. Knollmann Eds., Section VIII, "Chemotherapy of Neoplastic Diseases", Chapters 60-63, pp. 1665-1770, McGraw-Hill, NY, include but are not limited to anthracyclines, platinums, taxols, topisomerase inhibitors, anti-metabolites, anti-tumor antibiotics, mitotic inhibitors, and alkylating agents.

In addition to the foregoing, the methods of the present disclosure are related to treatment of cancer indications and further comprises treating the patient via surgery, radiation, and/or administering to a patient in need thereof an effective amount of a chemical small molecule or biologic drug including, but not limited to, a peptide, polypeptide, protein, nucleic acid therapeutic, conventionally used or currently being developed, to treat tumorous conditions. This includes antibodies and antigen-binding fragments, other than those disclosed herein, cytokines, antisense oligonucleotides, siRNAs, and miRNAs.

The therapeutic methods disclosed and claimed herein include the use of the antibodies disclosed herein alone, and/or in combinations with one another, and/or with antigen-binding fragments thereof of the present disclosure that bind to SIRPα, and/or with competing antibodies exhibiting appropriate biological/therapeutic activity, as well, for example, all possible combinations of these antibody compounds to achieve the greatest treatment efficacy.

In addition, the present therapeutic methods also encompass the use of these antibodies, antigen-binding fragments thereof, competing antibodies, and combinations thereof in further in combination with: (1) one or more anti-tumor therapeutic treatments selected from surgery, radiation, anti-tumor, and anti-neoplastic agents or combinations of any of these, or (2) one or more of anti-tumor biological agents or (3) equivalents of any of the foregoing of (1) or (2) as would be apparent to one of ordinary skill in the art, in appropriate combination(s) to achieve the desired therapeutic treatment effect for the particular indication.

Antibodies and small molecule drugs that increase the immune response to cancer by modulating co-stimulatory or inhibitory interactions that influence the T-cell response to tumor antigens, including inhibitors of immune checkpoints and modulators of co-stimulatory molecules, are also of particular interest in the context of the combination therapeutic methods encompassed herein and include, but are not limited to, other anti-SIRPα antibodies. Administration of therapeutic agents that bind to the SIRPα protein, for example, antibodies or small molecules that bind to SIRPα and prevent interaction between CD47 and SIRPα, are administered to a patient, causing the clearance of cancer cells via phagocytosis. The therapeutic agent that binds to the SIRPα protein is combined with a therapeutic agent such as an antibody, a chemical small molecule or biologic drug which is directed against one or more additional cellular targets selected from CD47 (Cluster of Differentiation 47), CD70 (Cluster of Differentiation 70), CD200 (OX-2 membrane glycoprotein, Cluster of Differentiation 200), CD154 (Cluster of Differentiation 154, CD40L, CD40 ligand, Cluster of Differentiation 40 ligand), CD223 (Lymphocyte-activation gene 3, LAG3, Cluster of Differentiation 223), KIR (Killer-cell immunoglobulin-like receptors), GITR (TNFRSF18, glucocorticoid-induced TNFR-related protein, activation-inducible TNFR family receptor, AITR, Tumor necrosis factor receptor superfamily member 18), CD20 (Cluster of Differentiation 20), CD28 (Cluster of Differentiation 28), CD40 (Cluster of Differentiation 40, Bp50, CDW40, TNFRSF5, Tumor necrosis factor receptor superfamily member 5, p50), CD86 (B7-2, Cluster of Differentiation 86), CD160 (Cluster of Differentiation 160, BY55, NK1, NK28), CD258 (LIGHT, Cluster of Differentiation 258, Tumor necrosis factor ligand superfamily member 14, TNFSF14, herpesvirus entry mediator ligand (HVEM-L), CD270 (HVEM, Tumor necrosis factor receptor superfamily member 14, herpesvirus entry mediator, Cluster of Differentiation 270, LIGHTR, HVEA), CD275 (ICOSL, ICOS ligand, Inducible T-cell co-stimulator ligand, Cluster of Differentiation 275), CD276 (B7-H3, B7 homolog 3, Cluster of Differentiation 276), OX40L (OX40 Ligand), B7-H4 (B7 homolog 4, VTCN1, V-set domain-containing T-cell activation inhibitor 1), GITRL (Glucocorticoid-induced tumor necrosis factor receptor-ligand, glucocorticoid-induced TNFR-ligand), 4-1BBL (4-1BB ligand), CD3 (Cluster of Differentiation 3, T3D), CD25 (IL2Rα, Cluster of Differentiation 25, Interleukin-2 Receptor α chain, IL-2 Receptor α chain), CD48 (Cluster of Differentiation 48, B-lymphocyte activation marker, BLAST-1, signaling lymphocytic activation molecule 2, SLAMF2), CD66a (Ceacam-1, Carcinoembryonic antigen-related cell adhesion molecule 1, biliary glycoprotein, BGP, BGP1, BGPI, Cluster of Differentiation 66a), CD80 (B7-1, Cluster of Differentiation 80), CD94 (Cluster of Differentiation 94), NKG2A (Natural killer group 2A, killer cell lectin-like receptor subfamily D member 1, KLRD1), CD96 (Cluster of Differentiation 96, TActILE, T-cell activation increased late expression), CD112 (PVRL2, nectin, Poliovirus receptor-related 2, herpesvirus entry mediator B, HVEB, nectin-2, Cluster of Differentiation 112), CD115 (CSF1R, Colony stimulating factor 1 receptor, macrophage colony-stimulating factor receptor, M-CSFR, Cluster of Differentiation 115), CD205 (DEC-205, LY75, Lymphocyte antigen 75, Cluster of Differentiation 205), CD226 (DNAM1, Cluster of Differentiation 226, DNAX Accessory Molecule-1, PTA1, platelet and T-cell activation antigen 1), CD244 (Cluster of Differentiation 244, Natural killer cell receptor 2B4), CD262 (DRS, TrailR2, TRAIL-R2, Tumor necrosis factor receptor superfamily member 10b, TNFRSF10B, Cluster of Differentiation 262, KILLER, TRICK2, TRICKB, ZTNFR9, TRICK2A, TRICK2B), CD284 (Toll-like Receptor-4, TLR4, Cluster of Differentiation 284), CD288 (Toll-like Receptor-8, TLR8, Cluster of Differentiation 288), Leukemia Inhibitor Factor (LIF), TNFSF15 (Tumor necrosis factor superfamily member 15, Vascular endothelial growth inhibitor, VEGI, TL1A), TDO2 (Tryptophan 2,3-dioxygenase, TPH2, TRPO), IGF-1R (Type 1 Insulin-like Growth Factor), GD2 (Disialoganglioside 2), TMIGD2 (Transmembrane and immunoglobulin domain-containing protein 2), RGMB (RGM domain family, member B), VISTA (V-domain immunoglobulin-containing suppressor of T-cell activation, B7-H5, B7 homolog 5), BTNL2 (Butyrophilin-like protein 2), Btn (Butyrophilin family), TIGIT (T-cell Immunoreceptor with Ig and ITIM domains, Vstm3, WUCAM), Siglecs (Sialic acid binding Ig-like lectins), Neurophilin, VEGFR (Vascular endothelial growth factor receptor), ILT family (LIRs, immunoglobulin-like transcript family, leukocyte immunoglobulin-like receptors), NKG families (Natural killer group families, C-type lectin transmembrane receptors), MICA (MHC class I polypeptide-related sequence A), TGFβ (Transforming growth factor β), STING pathway (Stimulator of interferon gene pathway), Arginase (Arginine amidinase, canavanase, L-arginase, arginine transamidinase), EGFRvIII (Epidermal growth factor receptor variant III), and HHLA2 (B7-H7, B7y, HERV-H LTR-associating protein 2, B7 homolog 7), inhibitors of PD-1 (Programmed cell death protein 1, PD-1, CD279, Cluster of Differentiation 279), PD-L1 (B7-H1, B7 homolog 1, Programmed death-ligand 1, CD274, cluster of Differentiation 274), PD-L2 (B7-DC, Programmed cell death 1 ligand 2, PDCD1LG2, CD273, Cluster of Differentiation 273), CTLA-4 (Cytotoxic T-lymphocyte-associated protein 4, CD152, Cluster of Differentiation 152), BTLA (B- and T-lymphocyte attenuator, CD272, Cluster of Differentiation 272), Indoleamine 2,3-dioxygenase (IDO, IDO1), TIM3 (HAVCR2, Hepatitis A virus cellular receptor 2, T-cell immunoglobulin mucin-3, KIM-3, Kidney injury molecule 3, TIMD-3, T-cell immunoglobulin mucin-domain 3), A2A adenosine receptor (ADO receptor), CD39 (ectonucleoside triphosphate diphosphohydrolase-1, Cluster of Differentiation 39, ENTPD1), and CD73 (Ecto-5'-nucleotidase, 5'-nucleotidase, 5'-NT, Cluster of Differentiation 73), CD27 (Cluster of Differentiation 27), ICOS (CD278, Cluster of Differentiation 278, Inducible T-cell Co-stimulator), CD137 (4-1BB, Cluster of Differentiation 137, tumor necrosis factor receptor superfamily member 9, TNFRSF9), OX40 (CD134, Cluster of Differentiation 134), TNF SF25 (Tumor necrosis factor receptor superfamily member 25), IL-10 (Interleukin-10, human cytokine synthesis inhibitory factor, CSIF), and Galectins.

ERBITUX® (cetuximab, Bristol-Meyers Squibb) is an example of an approved recombinant, human/mouse chimeric monoclonal antibody that binds specifically to the extracellular domain of the human epidermal growth factor receptor (EGFR).

RITUXAN® (rituximab, Biogen IDEC/Genentech) is an example of an approved anti-CD20 antibody.

YERVOY® (ipilimumab; Bristol-Meyers Squibb) is an example of an approved anti-CTLA-4 antibody.

KEYTRUDA® (pembrolizumab; Merck) and OPDIVO® (nivolumab; Bristol-Meyers Squibb Company) are examples of approved anti-PD-1 antibodies.

TECENTRIQ™ (atezolizumab; Roche) is an example of an approved anti-PD-L1 antibody.

BAVENCIO™ (avelumab; Merck KGaA and Pfizer and Eli Lilly and Company) is an example of an approved anti-PD-L1 antibody.

IMFINZI™ (Durvalumab; Medimmune/AstraZeneca) is an example of an approved anti-PD-L1 antibody.

The Examples illustrate various embodiments of the present disclosure, but they should not be considered as limiting the disclosure to only these particularly disclosed embodiments.

EXAMPLES

Example 1

Amino Acid Sequences

| Light Chain CDRs | | | | | | | |
|---|---|---|---|---|---|---|---|
| LCDR1 | | LCDR2 | | LCDR3 | | | |
| SEQ ID NO: 1 | RASSGVNYMY | SEQ ID NO: 2 | YTSILAP | SEQ ID NO: 3 | QQFTSSPYT | | |
| SEQ ID NO: 4 | RASQSIGTSIH | SEQ ID NO: 5 | YGSESIS | SEQ ID NO: 6 | QQSNTWPLT | | |
| SEQ ID NO: 7 | SASSIIGSDFLH | SEQ ID NO: 8 | RTSILAS | SEQ ID NO: 9 | QQGSGLPLT | | |
| SEQ ID NO: 10 | KASQDINSHLS | SEQ ID NO: 11 | RANRLAD | SEQ ID NO: 12 | LQYDEFPYT | | |
| SEQ ID NO: 13 | SASSSVSYMY | SEQ ID NO: 14 | LTSNLAS | SEQ ID NO: 15 | QQWSGNPFT | | |
| SEQ ID NO: 16 | RASENIYSYLT | SEQ ID NO: 17 | NAKTLAE | SEQ ID NO: 18 | QHHYGSPRT | | |

| Light Chain CDRs | | | | | |
|---|---|---|---|---|---|
| LCDR1 | | LCDR2 | | LCDR3 | |
| SEQ ID NO: 19 | SASSSISSNFLH | SEQ ID NO: 20 | RTSILAS | SEQ ID NO: 21 | QQGSGLPLT |
| SEQ ID NO: 22 | SSVSY | SEQ ID NO: 23 | DTS | SEQ ID NO: 24 | QQWSSFPWT |
| SEQ ID NO: 25 | EDIYDR | SEQ ID NO: 26 | GTA | SEQ ID NO: 27 | QQYWTTPWT |
| SEQ ID NO: 28 | SSVNY | SEQ ID NO: 29 | YTS | SEQ ID NO: 30 | QQFTSSPFT |
| | | SEQ ID NO: 31 | RANRLAT | SEQ ID NO: 32 | QQYDEFPYT |

| Heavy Chain CDRs | | | | | |
|---|---|---|---|---|---|
| HCDR1 | | HCDR2 | | HCDR3 | |
| SEQ ID NO: 33 | KYWIE | SEQ ID NO: 34 | EILPGSVITNYNEKFKG | SEQ ID NO: 35 | WGLYDSDDGVDY |
| SEQ ID NO: 36 | GCTMS | SEQ ID NO: 37 | YISNGGDITYYPDTVKG | SEQ ID NO: 38 | LDGYYYAMDF |
| SEQ ID NO: 39 | SYVMH | SEQ ID NO: 40 | YINPYNDGPKYNEKFKG | SEQ ID NO: 41 | WDYFNSASGFAF |
| SEQ ID NO: 42 | DYFLN | SEQ ID NO: 43 | RINPYNGDSFINQNFRD | SEQ ID NO: 44 | GGYDGYFIAYFDY |
| SEQ ID NO: 45 | SYTMH | SEQ ID NO: 46 | YINPTIGYTEYNQKFKD | SEQ ID NO: 47 | LVITSVLGRAMDY |
| SEQ ID NO: 48 | DYGVN | SEQ ID NO: 49 | WVNTNTRESTYVEDFKG | SEQ ID NO: 50 | GAYDAYYYYGMDY |
| SEQ ID NO: 51 | TYVMH | SEQ ID NO: 52 | YINPNNDGPNYNEKFKG | SEQ ID NO: 53 | WDSYNSAAGFAY |
| SEQ ID NO: 54 | GFTLSTYT | SEQ ID NO: 55 | ITSGDTYT | SEQ ID NO: 56 | TRDRPLFH |
| SEQ ID NO: 57 | GYTFTDYE | SEQ ID NO: 58 | IHPGSGGT | SEQ ID NO: 59 | TRAVSGYYAMDY |
| SEQ ID NO: 60 | GYTFSNYL | SEQ ID NO: 61 | IYPGDNNT | SEQ ID NO: 62 | AGGTDYDGFAN |
| | | | | SEQ ID NO: 63 | ARAVSGYYAMDY |

| Murine Light Chain (V$_L$) Variable Domain Sequences and Human Light Chain (V$_L$) Variable Domain Sequences | |
|---|---|
| SEQ ID NO: 64 | ENVLTQSPAIMSASLGEKVTMSCRASSGVNYMYWYQQKSDASPKWYYTSILAPGVPARFSGSGSGNSYSLTISSMEGEDAATYYCQQFTSSPYTFGGGTKLEIK |
| SEQ ID NO: 65 | DILLTQSPAILSVSPGERVSFSCRASQSIGTSIHWYQQRTNGSPRLLIKYGSESISGIPSRFSGSGSGTDFTLSINSVESEDIADYYCQQSNTWPLTFGDGTKLELK |
| SEQ ID NO: 66 | EIVLTQSPTTMAASPGEKITIICSASSIIGSDFLHWYQQRPGFSPKFLIYRTSILASGVPTRFTGSGSGTSYSLTIGTMEAEDVATYYCQQGSGLPLTFGSGTKLEMK |
| SEQ ID NO: 67 | DIKLTQSQSSMYSSLGQRVTITCKASQDINSHLSWFQEKPGKSPKTLIYRANRLADGVPSRFSGSGSGQDYFLTISSLEYEDVGIYYCLQYDEFPYTFGGGTKLEIK |
| SEQ ID NO: 68 | QIVLTQSPALMSASPGEKVTMTCSASSSVSYMYWFQQKPRSSPKPWIYLTSNLASGVPARFSGSGSGTSYSLTISSMEAEDAATYYCQQWSGNPFTFGSGTKLEIK |
| SEQ ID NO: 69 | DIQMTQSPASLSASVGETVTITCRASENIYSYLTWYKQGKSPQLLVYNAKTLAEGVPSRFSGSGSGTQFSLKINSLQPEDFGSYYCQHHYGSPRTFGGGTKLEIK |
| SEQ ID NO: 70 | EIVLTQSPTTMAASPGEKITIICSASSSISSNFLHWYQQKPGFSPRFLIYRTSILASGVPTRFSGSGSGTSYSLTIDTMEAEDVATYYCQQGSGLPLTFGSGTKLEIK |
| SEQ ID NO: 71 | QIVLTQSPAIMSASPGEKVTMTCSASSSVSYMYWYQQKPGSSPRLLIYDTSNLASGVPVRFSGSGSGTSYSLTISRMEAEDAATYYCQQWSSFPWTFGGGTKLEIK |
| SEQ ID NO: 72 | DIQMTQSSSSFSGSLGDRLTINCKASEDIYDRVAWYQQKPGNAPRLLISGTASLETGVLSRFSGSGSGKDYTLSINGLQAEDVATYYCQQYWTTPWTFGGGTKLEIK |

| Murine Light Chain (V_L) Variable Domain Sequences and Human Light Chain (V_L) Variable Domain Sequences |
| --- |
| SEQ ID NO: 73   ENVLTQSPAIMSASLGEKVTMSCRASSSVNYMYWYQQKSDASPKLWIYYTSKLAPGVPARFSGSGSG<br>NSYSLTISSMEGEDAATYYCQQFTSSPFTFGSGTKLEIK |
| SEQ ID NO: 74   DIQMTQSPSSLSASVGDRVTITCKASQDINSHLSWYQQKPGKAPKLLIYRANRLATGVPSRFSGSGSGT<br>DFTFTISSLQPEDIATYYCLQYDEFPYTFGGGTKLEIK |
| SEQ ID NO: 75   DIQMTQSPSSLSASVGDRVTITCKASQDINSHLSWYQQKPGKAPKLLIYRANRLATGVPSRFSGSGSGT<br>DFTFTISSLEYEDIATYYCLQYDEFPYTFGGGTKLEIK |
| SEQ ID NO: 76   DIQMTQSPSSLSASVGDRVTITCKASQDINSHLSWYQQKPGKAPKLLIYRANRLATGVPSRFSGSGSGT<br>DFTFTISSLQPEDIATYYCQQYDEFPYTFGGGTKLEIK |
| SEQ ID NO: 77   DIKMTQSPSSMYASLGQRVTITCKASQDINSHLSWFQEKPGKSPKTLIYRANRLADGVPSRFSGSGSG<br>QDYFLTISSLEYEDVGIYYCLQYDEFPYTFGGGTKLEIK |
| SEQ ID NO: 78   DIQMTQSPSSLSASVGDRVTITCKASEDIYDRVAWYQQKPGKAPKLLIYGTASLETGVPSRFSGSGSGT<br>DFTFTISSLQPEDIATYYCQQYWTTPWTFGGGTKVEIK |
| SEQ ID NO: 79   DIQMTQSPSSLSASVGDRVTITCKASEDIYDRVAWYQQKPGKAPKLLIYGTASLETGVPSRFSGSGSGT<br>DFTLTISSLQPEDFATYYCQQYWTTPWTFGGGTKVEIK |
| SEQ ID NO: 80   DIQMTQSPSSLSASVGDRVTITCKASEDIYDRVAWYQQKPGKAPKLLIYGTASLETGVLSRFSGSGSG<br>TDFTLTISSLQAEDFATYYCQQYWTTPWTFGGGTKVEIK |

| Murine Heavy Chain (V_H) Variable Domain Sequences and Human Heavy Chain (V_H) Variable Domain Sequences |
| --- |
| SEQ ID NO: 81   QVQLQQSGAELMKPGASVKISCKATGYSFTKYWIEWVKQRPGHGLEWIGEILPGSVITNYNEKFKGK<br>ATFTADTSSNTVYMQLSSLTSEDSAVYYCTKWGLYDSDDGVDYWGQGTTLTVSS |
| SEQ ID NO: 82   EVKLVESGGGLVQPGGSLKLSCAASGFSFSGCTMSWIRQTPERRLEWVAYISNGGDITYYPDTVKGRF<br>TISRDNAKNSLYLQMSSLKSEDTAMYYCARLDGYYYAMDFWGQGTSVTSS |
| SEQ ID NO: 83   EVQLQQSGPEVVKPGASVKMSCKASGYTFTSYVMHWVKQKPGQGLEWIGYINPYNDGPKYNEKFKG<br>KATLTSDKSSSTAYMELSSLTSEDSAVYFCARWDYFNSASGFAFWGQGTLVTVSA |
| SEQ ID NO: 84   EVQLQQSGPDLVKPGASVKISCKASGYSFTDYFLNWVKQSHGKSLEWIGRINPYNGDSFINQNFRDKA<br>TLTVDKSSTTAHMDLLSLTSEDSAIYYCGRGGYDGYFIAYFDYWGQGSLVTVSA |
| SEQ ID NO: 85   QVQLQQSAAELARPGASVKMSCKASGYTFTSYTMHWVKQRPGQGLEWIGYINPTIGYTEYNQKFKD<br>KTTLTADKSSSTAYMQLSSLTSEDSAVYYCVRLVITSVLGRAMDYWGQGTSVTSS |
| SEQ ID NO: 86   QIQLVQSGPELKKPGETVKISCKASGYTFTDYGVNWVKQGPGKDLQWMGWVNTNTRESTYVEDFKG<br>RFAFSLETSASTAYLQINNLKNEDSSTYFCARGAYDAYYYYGMDYWGQGTSVTVSS |
| SEQ ID NO: 87   EVQLQQSGPELVKPGASVKMSCRASGYTFSTYVMHWIKHRPGQGLEWIGYINPNNDGPNYNEKFKG<br>KATLTSDISSSTAYMELSSLTSEDSAVYFCSRWDSYNSAAGFAYWGHGTLVTVSA |
| SEQ ID NO: 88   EVQLQESGGGLVKPGGSLKLSCAASGFTLSTYTMSWVRQTPEKRLEWVAIITSGDTYTYYPDSVKGRF<br>TISRDNAKNTLYLQMSSLKSEDTGMYYCTRDRPLFHWGQGTTLTVST |
| SEQ ID NO: 89   EVQLQESGAELVRPGASVKLSCKALGYTFTDYEIHWVKETPVYGLEWIGDIHPGSGGTANNQKFKGK<br>ATLTADKSSNTAYMELSSLTSEDSAVYYCTRAVSGYYAMDYWGQGTSVTVSS |
| SEQ ID NO: 90   EVQLQESGAELVRPGTSVKMSCKAAGYTFSNYLIGWIKQRPGHGLEWIGDIYPGDNNTNYNEKFRVK<br>ATLTADTSSNTAYMEILTSLTSEDSAIYYCAGGTDYDGFANWGQGTLVTVSA |
| SEQ ID NO: 91   QVQLVQSGAEVKKPGASVKVSCKASGYSFTDYFLNWVRQAPGQGLEWMGRINPYNGDSFINQNFRD<br>RVTMTRDTSTSTVYMELSSLRSEDTAVYYCARGGYDGYFIAYFDYWGAGTTVTVSS |
| SEQ ID NO: 92   QVQLVQSGAEVKKPGSSVKVSCKASGYSFTDYFLNWVRQAPGQGLEWMGRINPYNGDSFINQNFRD<br>RVTITADKSTSTAYMELSSLRSEDTAVYYCARGGYDGYFIAYFDYWGAGTTVTVSS |
| SEQ ID NO: 93   EVQLVQSGAEVKKPGESLKISCKGSGYSFTDYFLNWVRQMPGKGLEWMGRINPYNGDSFINQNFRDQ<br>VTISADKSISTAYLQWSSLKASDTAMYYCARGGYDGYFIAYFDYWGAGTTVTVSS |
| SEQ ID NO: 94   QVQLVQSGAEVKKPGASVKVSCKASGYSFTDYFLNWVRQAPGQGLEWMGRINPYNGDSFINQNFRD<br>RVTMTVDTSTSTVYMELSSLRSEDTAVYYCARGGYDGYFIAYFDYWGAGTTVTVSS |
| SEQ ID NO: 95   QVQLVQSGAEVKKPGASVKVSCKASGYTFTDYEIHWVRQAPGQGLEWMGDIHPGSGGTANNQKFK<br>GRVTMTRDTSTSTVYMELSSLRSEDTAVYYCARAVSGYYAMDYWGQGTLVTVSS |

| Murine Heavy Chain (V_H) Variable Domain Sequences and Human Heavy Chain (V_H) Variable Domain Sequences |
| --- |
| SEQ ID NO: 96   QVQLVQSGAEVKKPGSSVKVSCKASGYTFTDYEIHWVRQAPGQGLEWMGDIHPGSGGTANNQKFKG<br>RVTITADESTSTAYMELSSLRSEDTAVYYCARAVSGYYAMDYWGQGTLVTVSS |
| SEQ ID NO: 97   QVQLVQSGAEVKKPGASVKVSCKASGYTFTDYEIHWVRQAPGQGLEWMGDIHPGSGGTANNQKFK<br>GRVTMTADTSTSTVYMELSSLRSEDTAVYYCTRAVSGYYAMDYWGQGTLVTVSS |

| Murine Light Chain (LC) Sequences and Human Light Chain (LC) Sequences |
| --- |
| SEQ ID NO: 98   ENVLTQSPAMSASLGEKVTMSCRASSGVNYMYWYQQKSDASPKLLIYYTSILAPGVPARFSGSGSG<br>NSYSLTISSMEGEDAATYYCQQFTSSPYTFGGGTKLEIKRADAAPTVSIFPPSSEQLTSGGASVVCFLN<br>NFYPKDINVKWKIDGSERQNGVLNSWTDQDSKDSTYSMSSTLTLTKDEYERHNSYTCEATHKTSTS<br>PIVKSFNRNEC |
| SEQ ID NO: 99   DILLTQSPAILSVSPGERVSFSCRASQSIGTSIHWYQQRTNGSPRLLIKYGSESISGIPSRFSGSGSGTDFT<br>LSINSVESEDIADYYCQQSNTWPLTFGDGTKLELKRADAAPTVSIFPPSSEQLTSGGASVVCFLNNFYP<br>KDINVKWKIDGSERQNGVLNSWTDQDSKDSTYSMSSTLTLTKDEYERHNSYTCEATHKTSTSPIVKS<br>FNRNEC |
| SEQ ID NO: 100  EIVLTQSPTTMAASPGEKITIICSASSIIGSDFLHWYQQRPGFSPKFLIYRTSILASGVPTRFTGSGSGTSY<br>SLTIGTMEAEDVATYYCQQGSGLPLTFGSGTKLEMKRADAAPTVSIFPPSSEQLTSGGASVVCFLNNF<br>YPKDINVKWKIDGSERQNGVLNSWTDQDSKDSTYSMSSTLTLTKDEYERHNSYTCEATHKTSTSPIV<br>KSFNRNEC |
| SEQ ID NO: 101  DIQMTQSPSSLSASVGDRVTITCKASQDINSHLSWYQQKPGKAPKLLIYRANRLATGVPSRFSGSGSG<br>TDFTFTISSLQPEDIATYYCLQYDEFPYTFGGGTKLEIKRTVAAPSVFIFPPSDEQLKSGTASVVCLLNN<br>FYPREAKVQWKVDNALQSGNSQESVTEQDSKDSTYSLSSTLTLSKADYEKHKVYACEVTHQGLSSP<br>VTKSFNRGEC |
| SEQ ID NO: 102  DIQMTQSPSSLSASVGDRVTITCKASQDINSHLSWYQQKPGKAPKLLIYRANRLATGVPSRFSGSGSG<br>TDFTFTISSLEYEDIATYYCLQYDEFPYTFGGGTKLEIKRTVAAPSVFIFPPSDEQLKSGTASVVCLLNN<br>FYPREAKVQWKVDNALQSGNSQESVTEQDSKDSTYSLSSTLTLSKADYEKHKVYACEVTHQGLSSP<br>VTKSFNRGEC |
| SEQ ID NO: 103  DIQMTQSPSSLSASVGDRVTITCKASQDINSHLSWYQQKPGKAPKLLIYRANRLATGVPSRFSGSGSG<br>TDFTFTISSLQPEDIATYYCQQYDEFPYTFGGGTKLEIKRTVAAPSVFIFPPSDEQLKSGTASVVCLLN<br>NFYPREAKVQWKVDNALQSGNSQESVTEQDSKDSTYSLSSTLTLSKADYEKHKVYACEVTHQGLSS<br>PVTKSFNRGEC |
| SEQ ID NO: 104  DIKMTQSPSSMYASLGQRVTITCKASQDINSHLSWFQEKPGKSPKTLIYRANRLADGVPSRFSGSGSG<br>QDYFLTISSLEYEDVGIYYCLQYDEFPYTFGGGTKLEIKRTVAAPSVFIFPPSDEQLKSGTASVVCLLN<br>NFYPREAKVQWKVDNALQSGNSQESVTEQDSKDSTYSLSSTLTLSKADYEKHKVYACEVTHQGLSS<br>PVTKSFNRGEC |
| SEQ ID NO: 105  DIQMTQSPSSLSASVGDRVTITCKASEDIYDRVAWYQQKPGKAPKLLIYGTASLETGVPSRFSGSGSG<br>TDFTFTISSLQPEDIATYYCQQYWTTPWTFGGGTKVEIKRTVAAPSVFIFPPSDEQLKSGTASVVCLLN<br>NFYPREAKVQWKVDNALQSGNSQESVTEQDSKDSTYSLSSTLTLSKADYEKHKVYACEVTHQGLSS<br>PVTKSFNRGEC |
| SEQ ID NO: 106  DIQMTQSPSSLSASVGDRVTITCKASEDIYDRVAWYQQKPGKAPKLLIYGTASLETGVPSRFSGSGSG<br>TDFTLTISSLQPEDFATYYCQQYWTTPWTFGGGTKVEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGL<br>SSPVTKSFNRGEC |
| SEQ ID NO: 107  DIQMTQSPSSLSASVGDRVTITCKASEDIYDRVAWYQQKPGKAPKLLIYGTASLETGVLSRFSGSGSG<br>TDFTLTISSLQAEDFATYYCQQYWTTPWTFGGGTKVEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGL<br>SSPVTKSFNRGEC |
| SEQ ID NO: 108  DIQMTQSSSSFSGSLGDRLTINCKASEDIYDRVAWYQQKPGNAPRLLISGTASLETGVLSRFSGSGSG<br>KDYTLSINGLQAEDVATYYCQQYWTTPWTFGGGTKLEIKRTVAAPSVFIFPPSDEQLKSGTASVVCL<br>LNNFYPREAKVQWKVDNALQSGNSQESVTEQDSKDSTYSLSSTLTLSKADYEKHKVYACEVTHQG<br>LSSPVTKSFNRGEC |

| Murine Heavy Chain (HC) Sequences and Human Heavy Chain (HC) Sequences |
| --- |
| SEQ ID NO: 109   QVQLQQSGAELMKPGASVKISCKATGYSFTKYWIEWVKQRPGHGLEWIGEILPGSVITNYNEKFKGK<br>ATFTADTSSNTVYMQLSSLTSEDSAVYYCTKWGLYDSDDGVDYWGQTTLTVSSAKTTPPSVYPLA<br>PGSAAQTNSMVTLGCLVKGYFPEPVTVTWNSGSLSSGVHTFPAVLQSDLYTLSSSVTVPSSTWPSETV<br>TCNVAHPASSTKVDKKIVPRDCGCKPCICTVPEVSSVFIFPPKPKDVLTITLTPKVTCVVVDISKDDPEV<br>QFSWFVDDVEVHTAQTQPREEQFNSTERSVSELPIMHQDWLNGKEEKCRVNSAAFPAPIEKTISKTKG |

| Murine Heavy Chain (HC) Sequences and Human Heavy Chain (HC) Sequences |
| --- |
| | RPKAPQVYTIPPPKEQMAKDKVSLTCMITDFFPEDITVEWQWNGQPAENYKNTQPIMDTDGSYFVYS<br>KLNVQKSNWEAGNTFTCSVLHEGLHNHHTEKSLSHSPGK |
| SEQ ID<br>NO: 110 | EVKLVESGGGLVQPGGSLKLSCAASGFSFSGCTMSWIRQTPERRLEWVAYISNGGDITYYPDTVKGRF<br>TISRDNAKNSLYLQMSSLKSEDTAMYYCARLDGYYYAMDFWGQGTSVTVSSAKTTPPSVYPLAPGS<br>AAQTNSMVTLGCLVKGYFPEPVTVTWNSGSLSSGVHTFPAVLQSDLYTLSSSVTVPSSTWPSETVTCN<br>VAHPASSTKVDKKIVPRDCGCKPCICTVPEVSSVFIFPPKPKDVLTITLTPKVTCVVVDISKDDPEVQFS<br>WFVDDVEVHTAQTQPREEQFNSTERSVSELPIMHQDWLNGKEEKCRVNSAAFPAPIEKTISKTKGRPK<br>APQVYTIPPPKEQMAKDKVSLTCMITDFFPEDITVEWQWNGQPAENYKNTQPIMDTDGSYFVYSKLN<br>VQKSNWEAGNTFTCSVLHEGLHNHHTEKSLSHSPGK |
| SEQ ID<br>NO: 111 | EVQLQQSGPEVVKPGASVKMSCKASGYTFTSYVMHWVKQPGQGLEWIGYINPYNDGPKYNEKEK<br>GKATLTSDKSSSTAYMELSSLTSEDSAVYFCARWDYFNSASGFAFWGQGTLVTVSAAKTTPPSVYPL<br>APGSAAQTNSMVTLGCLVKGYFPEPVTVTWNSGSLSSGVHTFPAVLQSDLYTLSSSVTVPSSTWPSET<br>VTCNVAHPASSTKVDKKIVPRDCGCKPCICTVPEVSSVFIFPPKPKDVLTITLTPKVTCVVVDISKDDPE<br>VQFSWFVDDVEVHTAQTQPREEQFNSTFRSVSELPIMHQDWLNGKEFKCRVNSAAFPAPIEKTISKTK<br>GRPKAPQVYTIPPPKEQMAKDKVSLTCMITDFFPEDITVEWQWNGQPAENYKNTQPIMDTDGSYFVY<br>SKLNVQKSNWEAGNTFTCSVLHEGLHNHHTEKSLSHSPGK |
| SEQ ID<br>NO: 112 | QVQLVQSGAEVKKPGASVKVSCKASGYSFTDYFLNWVRQAPGQGLEWMGRINPYNGDSFINQNFRD<br>RVTMTRDTSTSTVYMELSSLRSEDTAVYYCARGGYDGYFIAYFDYWGAGTTVTVSSASTKGPSVFPL<br>APCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLEPPKPKDTLMISRTPEVTCVVVDVSQ<br>EDPEVQFNWYVDGVEVHNAKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| SEQ ID<br>NO: 113 | QVQLVQSGAEVKKPGSSVKVSCKASGYSFTDYFLNWVRQAPGQGLEWMGRINPYNGDSFINQNFRD<br>RVTITADKSTSTAYMELSSLRSEDTAVYYCARGGYDGYFIAYFDYWGAGTTVTVSSASTKGPSVFPL<br>APCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLEPPKPKDTLMISRTPEVTCVVVDVSQ<br>EDPEVQFNWYVDGVEVHNAKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| SEQ ID<br>NO: 114 | EVQLVQSGAEVKKPGESLKISCKGSGYSFTDYFLNWVRQMPGKGLEWMGRINPYNGDSFINQNFRD<br>QVTISADKSISTAYLQWSSLKASDTAMYYCARGGYDGYFIAYFDYWGAGTTVTVSSASTKGPSVFPL<br>APCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLEPPKPKDTLMISRTPEVTCVVVDVSQ<br>EDPEVQFNWYVDGVEVHNAKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| SEQ ID<br>NO: 115 | QVQLVQSGAEVKKPGASVKVSCKASGYSFTDYFLNWVRQAPGQGLEWMGRINPYNGDSFINQNFRD<br>RVTMTVDTSTSTVYMELSSLRSEDTAVYYCARGGYDGYFIAYFDYWGAGTTVTVSSASTKGPSVFPL<br>APCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLEPPKPKDTLMISRTPEVTCVVVDVSQ<br>EDPEVQFNWYVDGVEVHNAKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| SEQ ID<br>NO: 116 | EVQLQQSGPDLVKPGASVKISCKASGYSFTDYFLNWVKQSHGKSLEWIGRINPYNGDSFINQNFRDK<br>ATLTVDKSSTTAHMDLLSLTSEDSAIYYCGRGGYDGYFIAYFDKYGAGTTVTVSSASTKGPSVFPLA<br>PCSRSTSESTAALGCLVKDYFPEPVTVSWNSGALTSGVHTFPAVLQSSGLYSLSSVVTVPSSSLGTKTY<br>TCNVDHKPSNTKVDKRVESKYGPPCPPCPAPEFLGGPSVFLEPPKPKDTLMISRTPEVTCVVVDVSQE<br>DPEVQFNWYVDGVEVHNAKTKPREEQFNSTYRVVSVLTVLHQDWLNGKEYKCKVSNKGLPSSIEKT<br>ISKAKGQPREPQVYTLPPSQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLGK |
| SEQ ID<br>NO: 117 | QVQLVQSGAEVKKPGASVKVSCKASGYTFTDYEIHWVRQAPGQGLEWMGDIHPGSGGTANNQKFK<br>GRVTMTRDTSTSTVYMELSSLRSEDTAVYYCARAVSGYYAMDYWGQGTLVTVSSASTKGPSVFPLA<br>PCSRSTSESTAALGCLVKDYFPEPVTVSWNSGALTSGVHTFPAVLQSSGLYSLSSVVTVPSSSLGTKTY<br>TCNVDHKPSNTKVDKRVESKYGPPCPPCPAPEFLGGPSVFLEPPKPKDTLMISRTPEVTCVVVDVSQE<br>DPEVQFNWYVDGVEVHNAKTKPREEQFNSTYRVVSVLTVLHQDWLNGKEYKCKVSNKGLPSSIEKT<br>ISKAKGQPREPQVYTLPPSQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLGK |
| SEQ ID<br>NO: 118 | QVQLVQSGAEVKKPGSSVKVSCKASGYTFTDYEIHWVRQAPGQGLEWMGDIHPGSGGTANNQKFK<br>GRVTITADESTSTAYMELSSLRSEDTAVYYCARAVSGYYAMDYWGQGTLVTVSSASTKGPSVFPLAP<br>CSRSTSESTAALGCLVKDYFPEPVTVSWNSGALTSGVHTFPAVLQSSGLYSLSSVVTVPSSSLGTKTYT<br>CNVDHKPSNTKVDKRVESKYGPPCPPCPAPEFLGGPSVFLEPPKPKDTLMISRTPEVTCVVVDVSQED<br>PEVQFNWYVDGVEVHNAKTKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLGK |
| SEQ ID<br>NO: 119 | QVQLVQSGAEVKKPGASVKVSCKASGYTFTDYEIHWVRQAPGQGLEWMGDIHPGSGGTANNQKFK<br>GRVTMTADTSTSTVYMELSSLRSEDTAVYYCTRAVSGYYAMDYWGQGTLVTVSSASTKGPSVFPLA |

| Murine Heavy Chain (HC) Sequences and Human Heavy Chain (HC) Sequences | |
|---|---|
| | PCSRSTSESTAALGCLVKDYFPEPVTVSWNSGALTSGVHTFPAVLQSSGLYSLSSVVTVPSSSLGTKTY<br>TCNVDHKPSNTKVDKRVESKYGPPCPPCPAPEFLGGPSVFLFPPKPKDTLMISRTPEVTCVVVDVSQE<br>DPEVQFNWYVDGVEVHNAKTKPREEQFNSTYRVVSVLTVLHQDWLNGKEYKCKVSNKGLPSSIEKT<br>ISKAKGQPREPQVYTLPPSQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLGK |
| SEQ ID<br>NO: 120 | EVQLQESGAELVRPGASVKLSCKALGYTFTDYEIHWVKETPVYGLEWIGDIHPGSGGTANNQKFKGK<br>ATLTADKSSNTAYMELSSLTSEDSAVYYCTRAVSGYYAMDYWGQGTSVTVSSASTKGPSVFPLAPCS<br>RSTSESTAALGCLVKDYFPEPVTVSWNSGALTSGVHTFPAVLQSSGLYSLSSVVTVPSSSLGTKTYTC<br>NVDHKPSNTKVDKRVESKYGPPCPPCPAPEFLGGPSVFLFPPKPKDTLMISRTPEVTCVVVDVSQEDP<br>EVQFNWYVDGVEVHNAKTKPREEQFNSTYRVVSVLTVLHQDWLNGKEYKCKVSNKGLPSSIEKTIS<br>KAKGQPREPQVYTLPPSQEEMTKNQVSLTCLVKGFYPSDIAVEWESNGQPENNYKTTPPVLDSDGSF<br>FLYSRLTVDKSRWQEGNVFSCSVMHEALHNHYTQKSLSLSLGK |

| SIRPα and SIRPγ Sequences | | |
|---|---|---|
| SEQ ID<br>NO: 121 | SIRPα | EEELQVIQPDKSVSVAAGESAILHCTVTSLIPVGPIQWFRGAGPARELIYNQKEGHFPRVTTVS<br>ESTKRENMDFSISISNITPADAGTYYCVKFRKGSPDTEFKSGAGTELSVRAKPSAPVVSGPAAR<br>ATPQHTVSFTCESHGFSPRDITLKWFKNGNELSDFQTNVDPVGESVSYSIHSTAKVVLTREDV<br>HSQVICEVAHVTLQGDPLRGTANLSETIRVPPTLEVTQQPVRAENQVNVTCQVRKFYPQRLQ<br>LTWLENGNVSRTETASTVTENKDGTYNWMSWLLVNVSAHRDDVKLTCQVEHDGQPAVSKS<br>HDLKVSAHPKEQGSNTAAENTGSNERNIYIVVGVVCTLLVALLMAALYLVRIRQKKAQGSTS<br>STRLHEPEKNAREITQDTNDITYADLNLPKGKKPAPQAAEPNNHTEYASIQTSPQPASEDTLT<br>YADLDMVHLNRTPKQPAPKPEPSFSEYASVQVPRK |
| SEQ ID<br>NO: 122 | SIRPγ | EEELQMIQPEKLLLVTGKTATLHCTVTSLLPVGPVLWFRGVGPGRELIYNQKEGHFPRVTT<br>VSDLTKRNNMDFSIRISSITPADVGTYYCVKFRKGSPENVEFKSGPGTEMALGAKPSAPVVLG<br>PAARTTPEHTVSFTCESHGFSPRDITLKWFKNGNELSDFQTNVDPTGQSVAYSIRSTARVVLG<br>PWDVRSQVICEVAHVTLQGDPLRGTANLSEAIRVPPTLEVTQQPMRVGNQVNVTCQVRKFY<br>PQSLQLTWSENGNVCQRETASTLTENKDGTYNWTSWFLVNISDQRDDVVLTCQVKHDGQL<br>AVSKRLALEVTVHQKDQSSDATPGPASSLTALLLIAVLLGPIYVPWKQKT |

| Human IgG Fc Sequences | |
|---|---|
| Human Fc IgG1<br>SEQ ID NO: 123 | ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| Human Fc IgG1-N297Q<br>SEQ ID NO: 124 | ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYQSTYRVVSV<br>LTVLHQDWLNGKEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRWQQGNVFSCSVM<br>HEALHNHYTQKSLSLSPGK |
| Human Fc-IgG2<br>SEQ ID NO: 125 | ASTKGPSVFPLAPCSRSTSESTAALGCLVKDYFPEPVTVSWNSGALTSGVHTFPAVLQSSGLY<br>SLSSVVTVPSSNFGTQTYTCNVDHKPSNTKVDKTVERKCCVECPPCPAPPVAGPSVFLFPPKP<br>KDTLMISRTPEVTCVVVDVSHEDPEVQFNWYVDGVEVHNAKTKPREEQFNSTFRVVSVLTV<br>VHQDWLNGKEYKCKVSNKGLPAPIEKTISKTKGQPREPQVYTLPPSREEMTKNQVSLTCLVK<br>GFYPSDIAVEWESNGQPENNYKTTPPMLDSDGSFFLYSKLTVDKSRWQQGNVFSCSVMHEA<br>LHNHYTQKSLSLSPGK |
| Human Fc-IgG3<br>SEQ ID NO: 126 | ASTKGPSVFPLAPCSRSTSGGTAALGCLVKDYFPEPVTVSWNSGALTSGVHTFPAVLQSSGLY<br>SLSSVVTVPSSSLGTQTYTCNVNHKPSNTKVDKRVELKTPLGDTTHTCPRCPEPKSCDTPPPCP<br>RCPEPKSCDTPPPCPRCPEPKSCDTPPPCPRCPAPELLGGPSVFLFPPKPKDTLMISRTPEVTCV<br>VVDVSHEDPEVQFKWYVDGVEVHNAKTKPREEQYNSTFRVVSVLTVLHQDWLNGKEYKC<br>KVSNKALPAPIEKTISKTKGQPREPQVYTLPPSREEMTKNQVSLTCLVKGFYPSDIAVEWESS<br>GQPENNYNTTPPMLDSDGSFFLYSKLTVDKSRWQQGNIFSCSVMHEALHNRFTQKSLSLSPG<br>K |
| Human Fc-IgG4<br>SEQ ID NO: 127 | ASTKGPSVFPLAPCSRSTSESTAALGCLVKDYFPEPVTVSWNSGALTSGVHTFPAVLQSSGLY<br>SLSSVVTVPSSSLGTKTYTCNVDHKPSNTKVDKRVESKYGPPCPSCPAPEFLGGPSVFLFPPKP<br>KDTLMISRTPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEGNVFSCSVMHEAL<br>HNHYTQKSLSLSLG |
| Human Fc-IgG4 S228P<br>SEQ ID NO: 128 | ASTKGPSVFPLAPCSRSTSESTAALGCLVKDYFPEPVTVSWNSGALTSGVHTFPAVLQSSGLY<br>SLSSVVTVPSSSLGTKTYTCNVDHKPSNTKVDKRVESKYGPPCPPCPAPEFLGGPSVFLFPPKP<br>KDTLMISRTPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQVSLTCLVK |

| | SIRPα and SIRPγ Sequences |
|---|---|
| | GFYPSDIAVEWESNGQPENNYKTTPPVLDSDGSFFLYSRLTVDKSRWQEGNVFSCSVMHEAL<br>HNHYTQKSLSLSLG |
| Human Fc-IgG4 PE<br>SEQ ID NO: 129 | ASTKGPSVFPLAPCSRSTSESTAALGCLVKDYFPEPVTVSWNSGALTSGVHTFPAVLQSSGLY<br>SLSSVVTVPSSSLGTKTYTCNVDHKPSNTKVDKRVESKYGPPCPPCPAPEFEGGPSVFLFPPKP<br>KDTLMISRTPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEGNVFSCSVMHEAL<br>HNHYTQKSLSLSLGK |
| Human Fc-IgG4 PE'<br>SEQ ID NO: 130 | ASTKGPSVFPLAPCSRSTSESTAALGCLVKDYFPEPVTVSWNSGALTSGVHTFPAVLQSSGLY<br>SLSSVVTVPSSSLGTKTYTCNVDHKPSNTKVDKRVESKYGPPCPPCPAPEFEGGPSVFLFPPKP<br>KDTLMISRTPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEGNVFSCSVMHEAL<br>HNHYTQKSLSLSLG |
| Human kappa LC<br>SEQ ID NO: 131 | RTVAAPSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC |

Example 2

Binding of SIRP Monoclonal Antibodies to SIRPα

The binding of anti-SIRP monoclonal antibodies (mAbs) of the present disclosure to SIRP alpha (SIRPα) was determined by solid phase ELISA using an Fc tagged human SIRP alpha. Binding by soluble anti-SIRP antibodies was measured in vitro.

Fc tagged human SIRPα (ACRO #SIG-H5251, genotype variant 1) is adsorbed to high-binding microtiter plates at a concentration of 1 µg/ml diluted in phosphate buffered saline (PBS) overnight at 4° C. The coating solution is removed, the wells are washed and then blocked with 75% casein in PBS containing 0.5% Tween 20 (PBST) for 60 minutes at room temperature while shaking. Blocking solution is removed, the wells are washed and incubated for 60 minutes at room temperature while shaking with either murine or human anti-SIRP mAbs diluted in PBST at a starting concentration of 30 µg/ml and reducing the concentration in 3-fold serial dilutions. Wells are washed three times with PBST and incubated for 60 minutes at room temperature while shaking with an HRP-labeled donkey anti-mouse or anti-human secondary antibody (Jackson ImmunoResearch Laboratories) diluted 1:10,000 in PBST. The wells are washed and then incubated with peroxidase substrate and the absorbance at 450 nm measured. The apparent affinities were calculated using a non-linear fit model (GraphPad Prism).

Figure 1V:
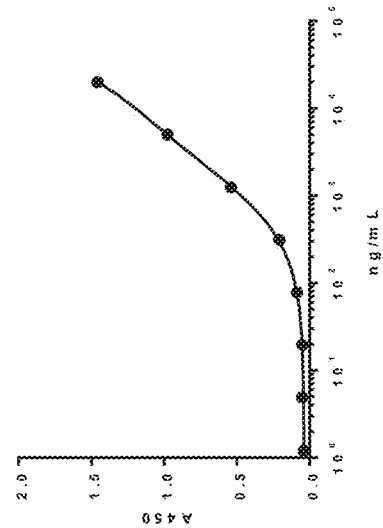

As shown in Table 1, all soluble anti-SIRP mAbs bound to human SIRPα with apparent affinities in the picomolar to nanomolar range. FIG. 1A-FIG. 1V demonstrate representative binding curves for antibodies of the present disclosure.

TABLE 1

Binding of anti-SIRP Antibodies to human SIRPα.

| | Human SIRPα binding $K_d$ (pM) |
|---|---|
| SIRP1 | 39 |
| SIRP2 | 182 |
| SIRP3 | 289 |
| SIRP4 | 161 |
| SIRP5 | 65 |
| SIRP6 | 131 |
| SIRP7 | 197 |
| SIRP8 | 57 |
| SIRP9 | 583 |
| SIRP10 | >10,000 |
| SIRP11 | 194 |
| SIRP12 | 165 |
| SIRP13 | 1,565 |
| SIRP14 | 565 |
| SIRP15 | 608 |
| SIRP16 | >40,000 |
| SIRP17 | 326 |
| SIRP18 | 364 |
| SIRP19 | >19,000 |
| SIRP20 | 157 |
| SIRP21 | 274 |
| SIRP22 | >11,000 |
| SIRP23 | 164 |

Example 3

Binding of Mouse Anti-SIRP mAbs to THP-1 Cells Expressing SIRPα

Binding activity of hybridoma-derived mouse SIRP antibodies SIRP1, SIRP2, and SIRP3 to THP-1 cells which express SIRPα, but not SIRPγ, was determined by flow cytometry.

THP-1 cells were incubated for 60 min at 37° C. with increasing concentrations of the mAbs diluted in PBS, pH 7.2. Cells were then washed with PBS and incubated for an additional hour with Alexa Fluor-647 labeled donkey anti-mouse antibody (Jackson ImmunoResearch Laboratories) in PBS. Cells were washed and binding analyzed using a C6 Accuri Flow Cytometer (Becton Dickinson).

Figure 2:
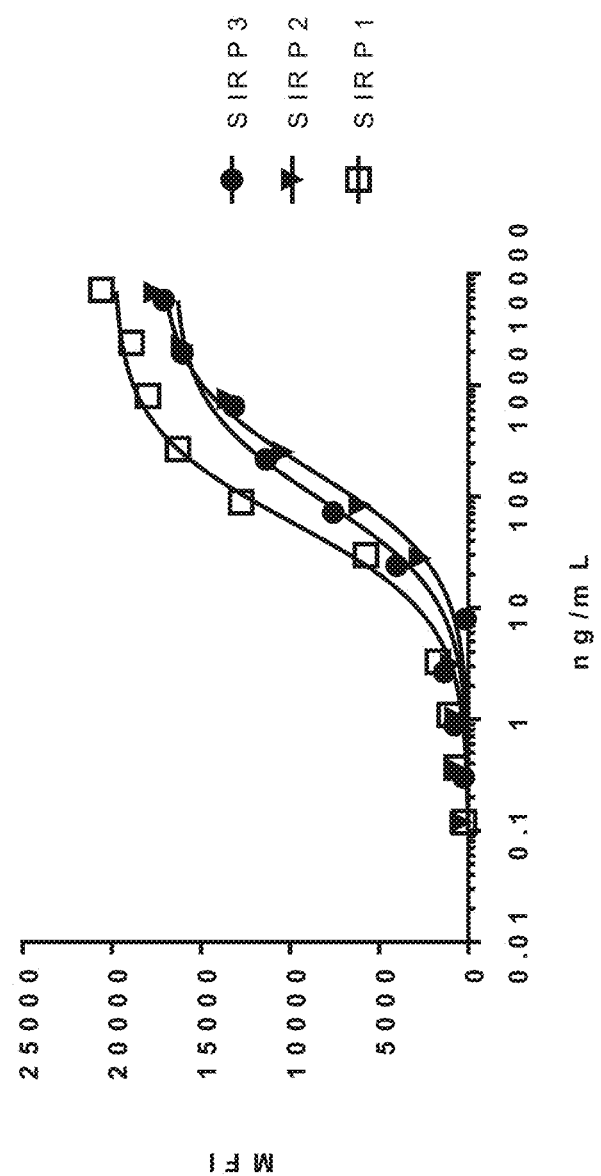
FIG. 2. Binding of Hybridoma Derived mAbs (SIRP1, SIRP2, and SIRP3) to THP1 cells Expressing SIRPα. Binding of SIRP1, SIRP2, and SIRP3 to THP-1 monocytic cell line was determined. Cells were incubated with increasing concentrations of antibody for 1 hr. Cells were washed and then incubated with Alexaflour 647-labelled secondary antibody for 1 hr. Cells were washed and antibody binding measured using flow cytometry.

As shown in FIG. 2, all the antibodies bound to SIRPα expressing THP-1 cells in a concentration-dependent manner.

Example 4

Binding of SIRP mAbs to SIRPγ

The binding of anti-SIRP antibodies of the present disclosure to SIRP gamma (SIRPγ) was determined by ELISA using an Fc tagged human SIRPγ. Binding by soluble anti-SIRP antibodies was measured in vitro.

Fc tagged human SIRPγ (ACRO #SIG-H5253) is adsorbed to high-binding microtiter plates at a concentration of 1 µg/ml in phosphate buffered saline (PBS) overnight at 4° C. The coating solution is removed, the wells are washed and then blocked with 75% casein in PBS containing 0.5% Tween 20 (PBST) for 60 minutes at room temperature while shaking. Blocking solution is removed, the wells are washed and incubated for 60 minutes at room temperature while shaking with anti-SIRP mAbs diluted in PBST at a starting concentration of 30 µg/ml and reducing the concentration in 3-fold serial dilutions. Wells are washed three times with PBST and incubated for 60 minutes at room temperature while shaking with an HRP labeled donkey anti-mouse or anti-human secondary antibody (Jackson ImmonResearch Laboratories) diluted 1:10,000 in PBST. The wells are washed and then incubated with peroxidase substrate and the absorbance at 450 nm determined. The apparent affinities were calculated using a non-linear fit model (GraphPad Prism).

Figure 3S:
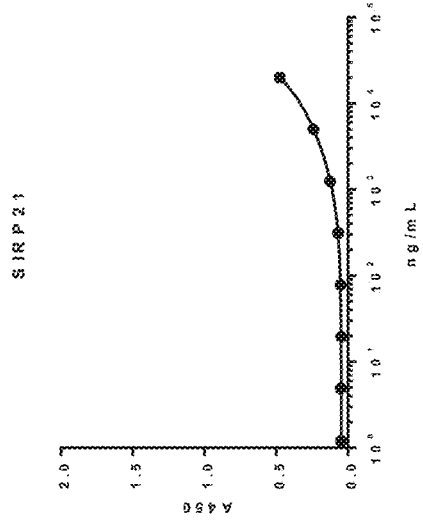
FIG. 3A-FIG. 3V. Binding of anti-SIRP antibodies to human SIRP gamma. Binding of anti-SIRP antibodies to recombinant human SIRP gamma (SIRPγ) was determined by solid-phase ELISA. High-binding ELISA plates were coated with recombinant human SIRP gamma and increasing concentrations of anti-SIRP antibodies were added for 1 hour. Wells were washed and then incubated with HRP-labeled secondary antibody for 1 hour followed by addition of peroxidase substrate and the absorbance at 450 nm was measured.
Figure 3T:
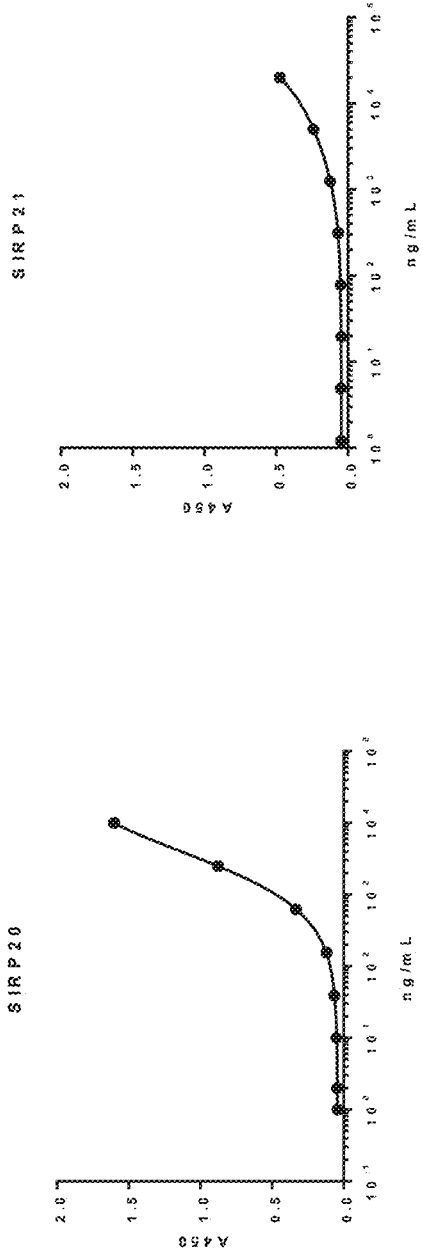
Figure 3U:
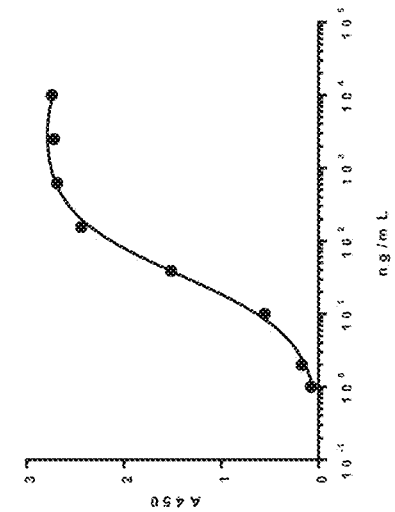
Figure 3V:
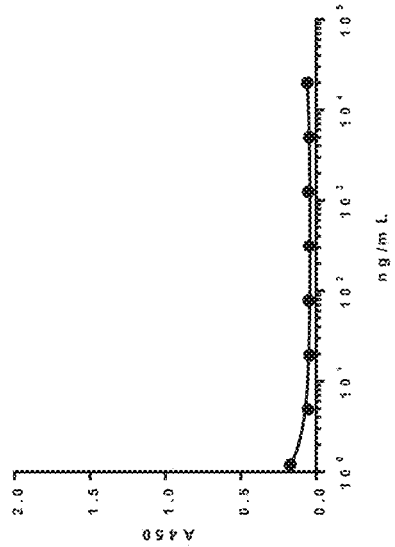

As shown in Table 2, the soluble anti-SIRP mAbs SIRP2, SIRP3, SIRP4, SIRP5, SIRP6, SIRP7, SIRP9, SIRP10, SIRP11, SIRP12, SIRP16, SIRP17, SIRP18, SIRP20, SIRP21 and SIRP23 bound to human SIRP gamma with apparent affinities in the picomolar or nanomolar range. Additionally, the anti-SIRP mAb SIRP1, SIRP8, SIRP13, SIRP14, SIRP15, SIRP19, and SIRP22 did not appreciably bind human SIRP gamma at mAb concentrations up to 30 µg/ml. FIG. 3A-FIG. 3V demonstrate representative binding curves derived from antibodies of the present disclosure.

TABLE 2

Binding of anti-SIRP Antibodies to Human SIRPγ.

| | Human SIRPγ binding Kd (pM) |
|---|---|
| SIRP1 | *NB |
| SIRP2 | 734 |
| SIRP3 | 170 |
| SIRP4 | 274 |
| SIRP5 | 126 |
| SIRP6 | 183 |
| SIRP7 | 99 |
| SIRP8 | *NB |
| SIRP9 | 510 |
| SIRP10 | >10,000 |
| SIRP11 | 7,223 |
| SIRP12 | >12,000 |
| SIRP13 | *NB |
| SIRP14 | *NB |
| SIRP15 | >14,000 |
| SIRP16 | *NB |
| SIRP17 | >15,000 |
| SIRP18 | >34,000 |
| SIRP19 | *NB |
| SIRP20 | >29,000 |
| SIRP21 | >21,000 |
| SIRP22 | *NB |
| SIRP23 | 225 |

*NB—no binding detected at mAb concentration up to 30 µg/ml

Example 5

Binding of Mouse mAbs to Jurkat T Cells Expressing SIRPγ

Binding activity of mouse hybridoma-derived SIRP mAbs to Jurkat cells which express SIRPγ, but not SIRPα, was determined by flow cytometry.

Jurkat cells were incubated for 60 min at 37° C., 5% $CO_2$ with increasing concentrations of the anti-SIRP mAbs diluted in phosphate buffered saline (PBS), pH 7.2. Cells were then washed with PBS and incubated for an additional hour with Alexa Fluor-647 labeled donkey anti-mouse antibody (Jackson ImmunoResearch Laboratories) in PBS. Cells were washed and binding analyzed using a C6 Accuri Flow Cytometer (Becton Dickinson). Alternatively, the cells were incubated for 1 h at 37° C. with the saturating concentration of 10 µg/ml of SIRP mAbs in binding buffer containing 1 mM EDTA (Sigma Aldrich), 1% FBS (Biowest) in PBS (Corning). The cells were then washed and stained for 45 min under the same conditions with donkey anti-mouse IgG fluorescein isothiocyanate (FITC)-linked secondary antibody (Jackson ImmunoResearch Laboratories). The cells were then washed and analyzed by flow cytometry (Attune, Life Technologies).

Figure 4B:
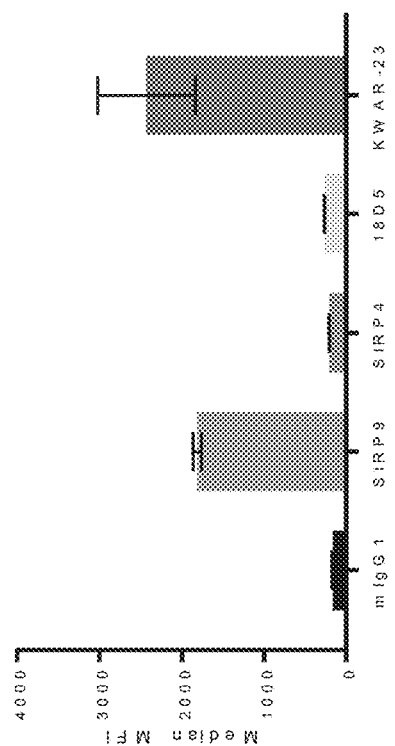
FIG. 4A-FIG. 4B. Binding of SIRP mAbs to Jurkat T cells Expressing SIRPγ. Binding of SIRP1, SIRP2, SIRP3, SIRP4 and SIRP9 to Jurkat T-ALL cells was determined. Cells were incubated with increasing concentrations of antibody FIG. 4A; or 10 µg/ml of the anti-SIRP antibodies for 1 hr.
Figure 4A:
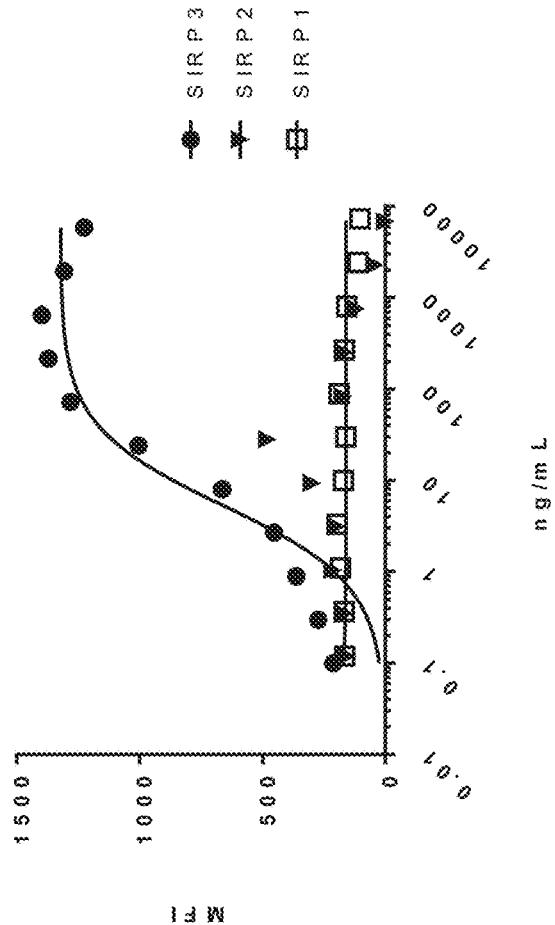
Figure 5A:
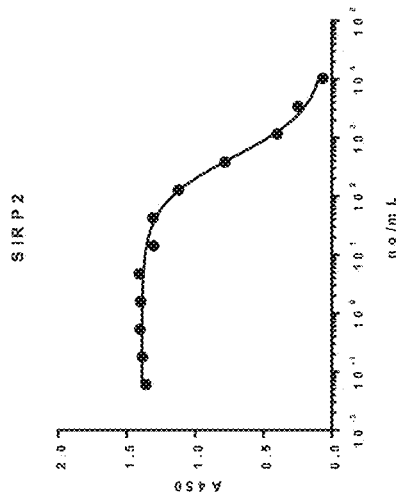
Figure 5B:
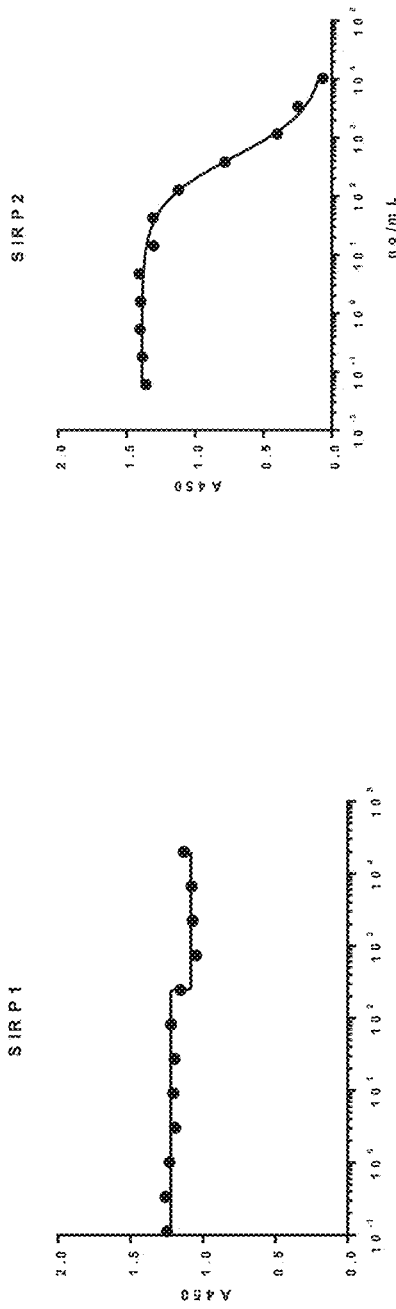
Figure 5C:
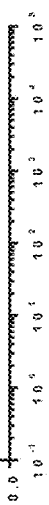
Figure 5D:
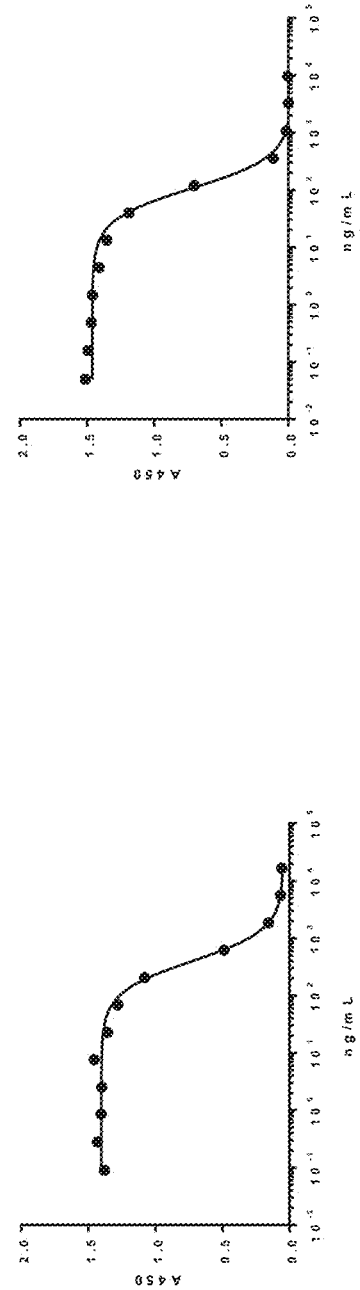
Figure 6A:
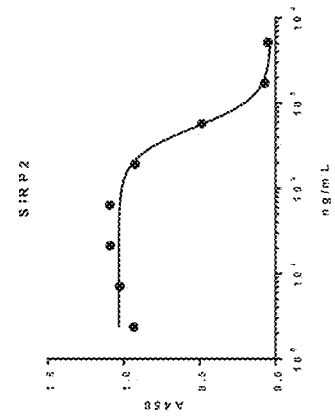
FIG. 6A-FIG. 6H. Blocking of human CD47/SIRPγ binding by anti-SIRP antibodies. The ability of anti-SIRP antibodies to block the interaction between CD47 and recombinant human SIRPγ was determined by solid-phase ELISA. High-binding ELISA plates were coated with recombinant human SIRPγ and increasing concentrations of anti-SIRP antibodies were added for 1 hour. Wells were washed and then incubated with an Fc tagged human CD47 for 1 hours. Wells were washed and then incubated with an HRP-labeled secondary antibody for 1 hour followed by addition of peroxidase substrate and the absorbance at 450 nm was measured.
Figure 6B:
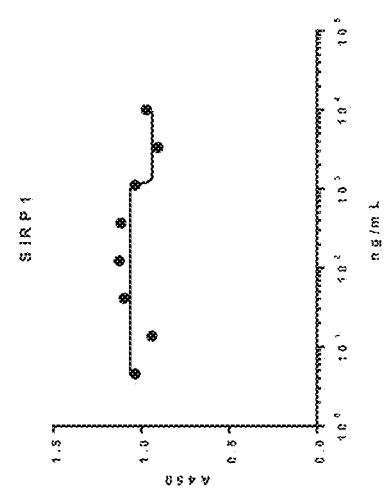
Figure 6C:
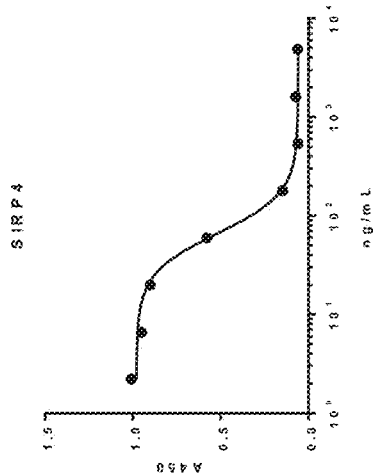
Figure 6D:
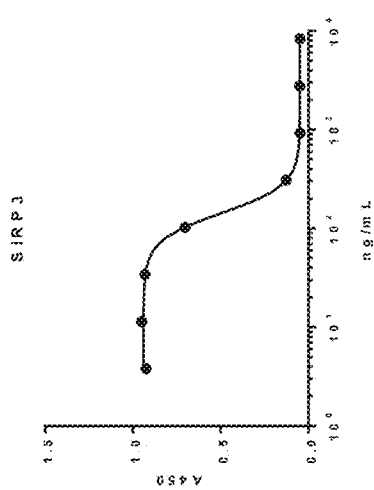
Figure 6E:
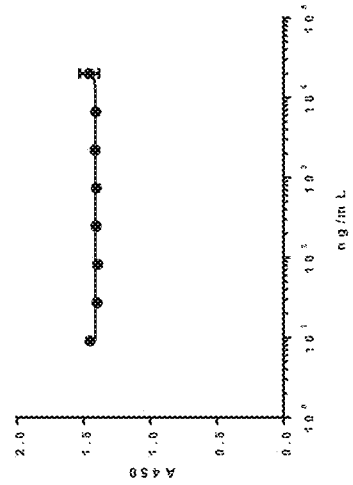
Figure 6F:
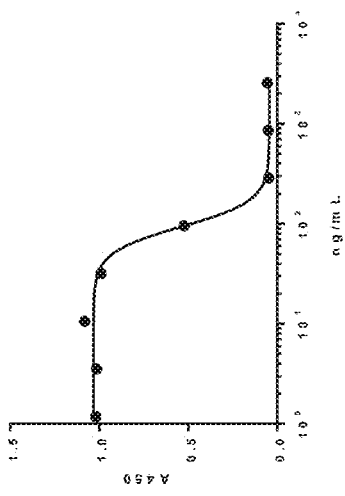
Figure 6G:
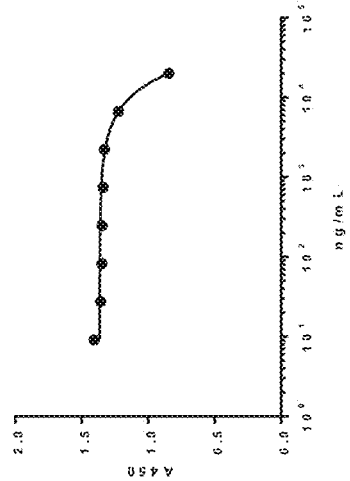
Figure 6H:
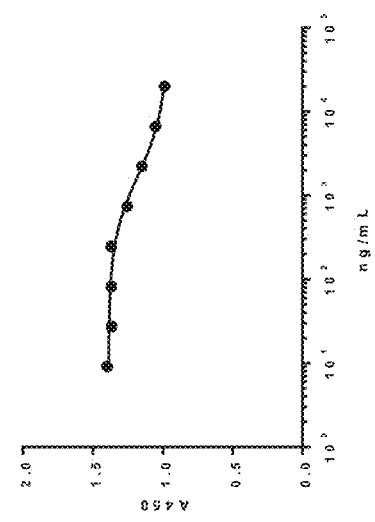

As shown in FIG. 4A, SIRP3 bound to SIRPγ expressing Jurkat cells whereas SIRP2 or SIRP1 exhibited no binding. In addition, as shown in FIG. 4B, SIRP9 bound to Jurkat cells at a concentration of 10 µg/ml, comparable to KWAR-23 which has previously been shown to bind to SIRPγ whereas SIRP4 exhibited no binding to SIRPγ on the Jurkat cells.

Example 6

Anti-SIRP mAbs Block CD47/SIRPα Binding

To assess the ability of anti-SIRP antibodies of the present disclosure to block the binding of CD47 to SIRPα in vitro the following method was employed using ELISA plates coated with Histidine (HIS) tagged human SIRPα.

HIS tagged human SIRPα (ACRO #SIG-H5225) is adsorbed to high-binding microtiter plates at a concentration of 1 µg/ml diluted in PBS overnight at 4° C. The coating solution is removed, the wells are washed and then blocked with 75% casein in PBS containing 0.5% Tween 20 (PBST) for 60 minutes at room temperature while shaking. Blocking solution is removed, the wells are washed and incubated for 60 minutes at room temperature while shaking with anti-SIRP mAbs diluted in PBST at a starting concentration of 30 µg/ml and reducing the concentration by 3-fold serial dilutions. Wells are washed three times with PBST and incubated for 60 minutes at room temperature while shaking with an FC tagged human CD47 (ACRO #CD7-H5256) at a concentration of 250 ng/ml in PBST. Wells are washed three times with PBST and incubated for 60 minutes at room temperature while shaking with an HRP labeled donkey anti-mouse or anti-human secondary antibody (Jackson ImmunoResearch Laboratories) diluted 1:20,000 in PBST. The wells are washed and then incubated with peroxidase substrate and the absorbance at 450 nm determined. The $IC_{50}$ was calculated using a non-linear fit model (GraphPad Prism).

As shown in Table 3, the soluble anti-SIRP mAbs SIRP2, SIRP3, SIRP4, and SIRP7 block the binding of human SIRPα to human CD47 with $IC_{50}$ values in the nanomolar range. In addition, the soluble anti-SIRP mAbs SIRP1, SIRP5, SIRP6, SIRP8, and SIRP10 were unable to block the binding of human SIRPα to human CD47 at mAb concentrations of up to 30 FIG. 5A-FIG. 5G demonstrates representative inhibition curves derived from antibodies of the present disclosure.

TABLE 3

Blocking of CD47/SIRPα Binding by anti-SIRP Antibodies.

| | SIRPα Blocking ($IC_{50}$ nM) |
|---|---|
| SIRP1 | *NB |
| SIRP2 | 3 |
| SIRP3 | 2.7 |
| SIRP4 | 0.71 |
| SIRP5 | *NB |
| SIRP6 | *NB |
| SIRP7 | 1.1 |
| SIRP8 | *NB |
| SIRP10 | *NB |

*NB—no blocking detected at mAb concentration of up to 30 μg/ml

Example 7

Anti-SIRP Monoclonal Antibodies Block CD47/SIRPγ Binding

To assess the effect of anti-SIRP mAbs of the present disclosure on binding of CD47 to SIRPγ in vitro the following method was employed using ELISA plates coated with HIS tagged human CD47.

HIS tagged human CD47 (ACRO #CD7-H5227) is adsorbed to high-binding microtiter plates at a concentration of 2 μg/ml diluted in PBS overnight at 4° C. The coating solution is removed, the wells are washed and then blocked with 75% casein in PBS containing 0.5% Tween 20 (PBST) for 60 minutes at room temperature while shaking. Blocking solution is removed, the wells are washed and incubated for 60 minutes at room temperature while shaking with anti-SIRP mAbs diluted in PBST at a starting concentration of 30 μg/ml and reducing the concentration in 3 fold serial dilutions and 0.5 μg/ml of human SIRPγ (ACRO# SIG-H5253). Wells are washed three times with PBST and incubated for 60 minutes at room temperature while shaking with an HRP labeled donkey anti-mouse or anti-human secondary antibody (Jackson ImmunoResearch Laboratories) diluted 1:20,000 in PBST. The wells are washed and then incubated with peroxidase substrate and the absorbance at 450 nm determined. The $IC_{50}$ was calculated using a non-linear fit model (GraphPad Prism).

As shown in Table 4, the soluble anti-SIRP mAbs SIRP2, SIRP3, SIRP4, SIRP5, SIRP6, and SIRP7 block the binding of human SIRPγ to human CD47 with $IC_{50}$ values in the nanomolar range. In addition, the soluble anti-SIRP mAbs SIRP1, SIRP8, SIRP9, and SIRP10 were unable to block the binding of human SIRPγ to human CD47 at mAb concentrations up to 30 μg/ml. FIG. 6A-FIG. 6H demonstrates representative inhibition curves derived from antibodies of the present disclosure.

TABLE 4

Blocking of CD47/SIRPγ Binding by anti-SIRP Antibodies.

| | SIRPγ Blocking ($IC_{50}$ nM) |
|---|---|
| SIRP1 | *NB |
| SIRP2 | 3.5 |
| SIRP3 | 0.96 |
| SIRP4 | 0.44 |
| SIRP5 | 0.163 |
| SIRP6 | 0.86 |
| SIRP7 | 0.63 |
| SIRP8 | *NB |
| SIRP9 | *NB |
| SIRP10 | *NB |

*NB—no blocking detected at mAb concentration up to 30 μg/ml

Example 8

Anti-SIRP mAbs Induce Phagocytosis

To assess the effect of anti-SIRP mAbs on phagocytosis of tumor cells by macrophages in vitro the following method was employed using flow cytometry.

Human monocyte-derived macrophages were derived from leukapheresis of healthy human peripheral blood and incubated in AIM-V media (Life Technologies) supplemented with 50 ng/ml M-CSF (Biolegend) for seven days. For the in vitro phagocytosis assay, macrophages were re-plated at a concentration of $3 \times 10^4$ cells per well in 100 μl of AIM-V media supplemented with 50 ng/ml M-CSF in a 96-well plate and allowed to adhere for 24 hours. Once the effector macrophages adhered to the culture dish, the targeted human cancer cells (Jurkat) were labeled with 1 μM 5(6)-Carboxyfluorescein diacetate N-succinimidyl ester (CFSE; Sigma Aldrich) and added to the macrophage cultures at a concentration of $8 \times 10^4$ cells in 100 μl of AIM-V media without supplements. Anti-SIRP mAbs were added at various concentrations, FIG. 7A, or 10 μg/ml of the antibodies, FIG. 7B, immediately upon mixture of target and effector cells and allowed to incubate at 37° C. for 3 hours. After 3 hours, all non-phagocytosed cells were removed, and the remaining cells washed three times with PBS. Cells were then incubated in Accutase (Stemcell Technologies) to detach macrophages, collected into microcentrifuge tubes, and incubated in 100 ng of allophycocyanin (APC) labeled CD14 antibodies (BD biosciences) for 30 minutes, washed once, and analyzed by flow cytometry (Attune, Life Technologies) for the percentage of $CD14^+$ cells that were also $CFSE^+$, indicating complete phagocytosis.

Figure 7B:
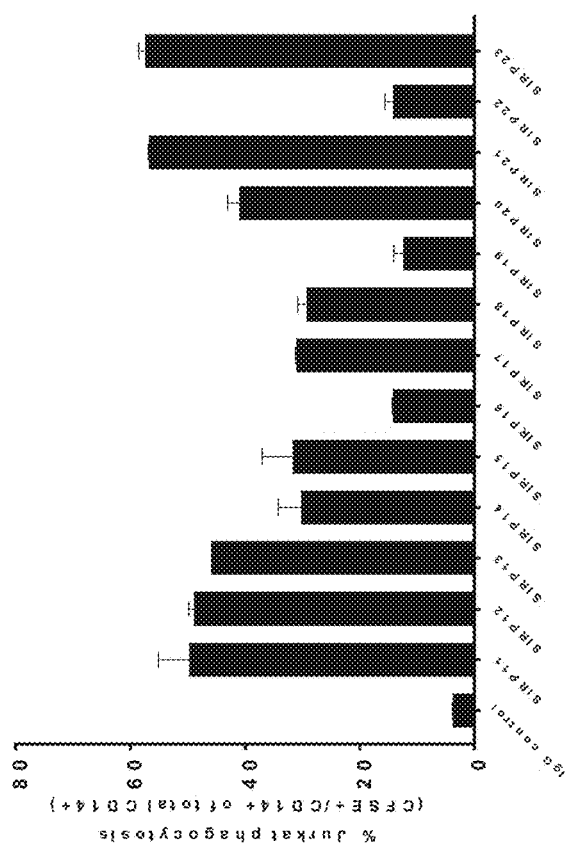
FIG. 7A-FIG. 7B. Anti-SIRP antibodies enhance phagocytosis. Human macrophages were plated at a concentration of $3\times10^4$ cells per well in a 96 well plate and allowed to adhere for 24 hours. $8\times10^4$ CFSE (1 µM) labeled human Jurkat T cells and increasing concentrations of anti-SIRP antibodies.
Figure 7A:
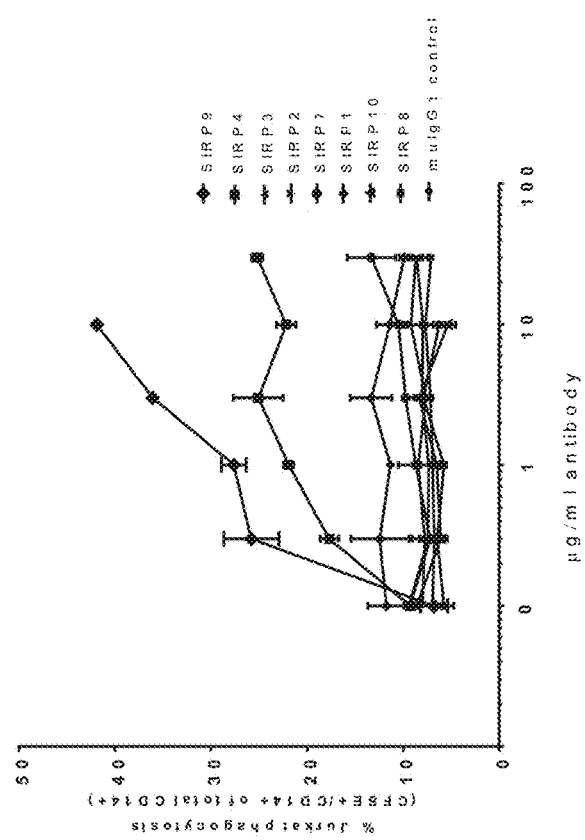
Figure 8C:
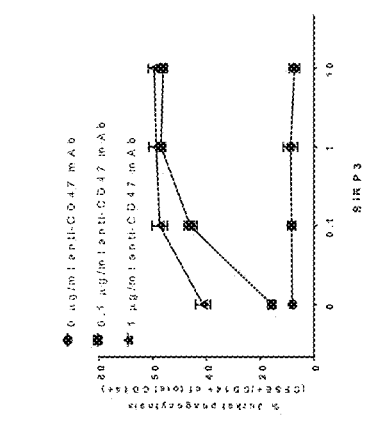
FIG. 8A-FIG. 8J. Anti-SIRP antibodies enhance phagocytosis in combination with anti-CD47 antibodies. Human macrophages were plated at a concentration of $3\times10^4$ cells per well in a 96 well plate and allowed to adhere for 24 hours. $8\times10^4$ CFSE (1 µM) labeled human Jurkat T cells and increasing concentrations of anti-SIRP antibodies alone, anti-CD47 antibody alone, or a combination of anti-SIRP antibodies and anti-CD47 antibody were added to the macrophage cultures and incubated at 37° C. for 3 hours. Non-phagocytosed Jurkat cells were removed and macrophage cultures were washed. Macrophages were trypsinized and stained for CD14. Flow cytometry was used to determine the percentage of $CD14^+$/$CFSE^+$ cells in the total $CD14^+$ population.
Figure 8F:
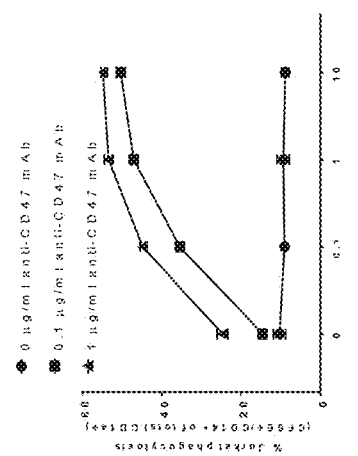
Figure 8B:
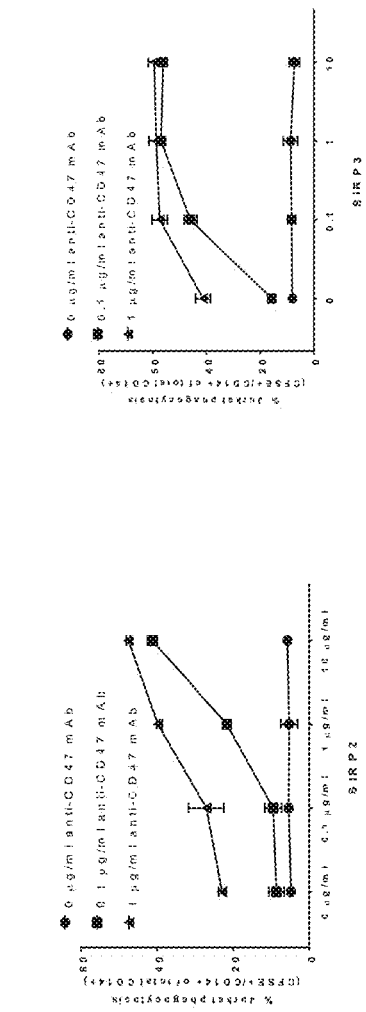
Figure 8E:
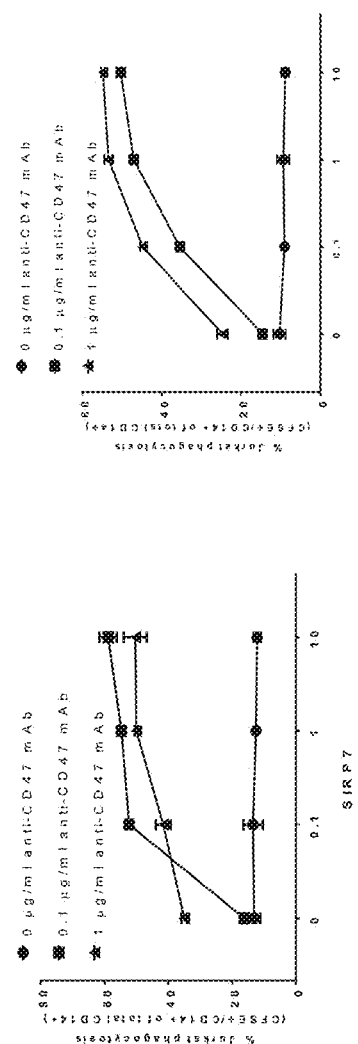
Figure 8A:
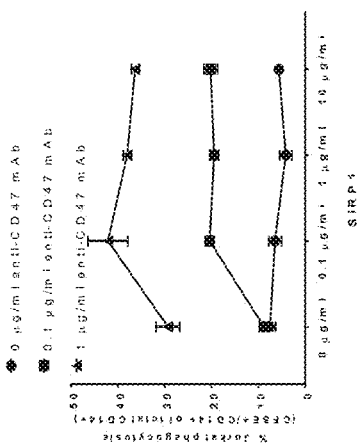
Figure 8D:
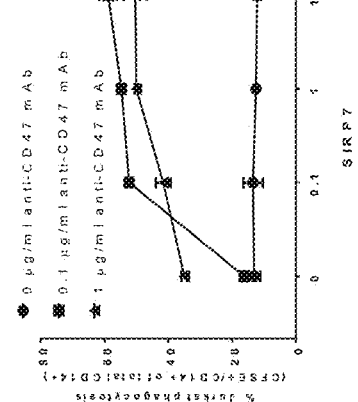
Figure 8G:
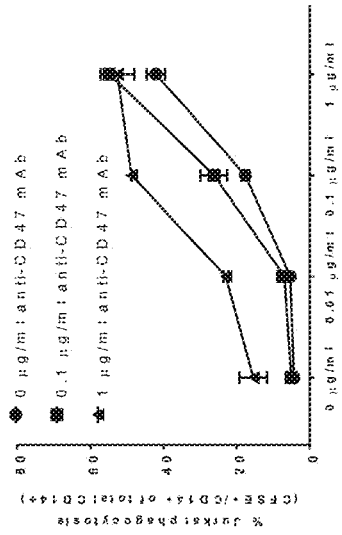
Figure 8I:
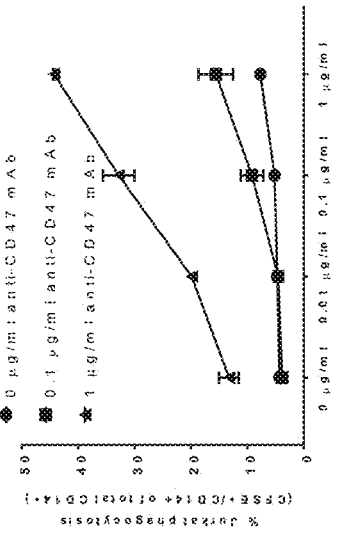
Figure 8H:
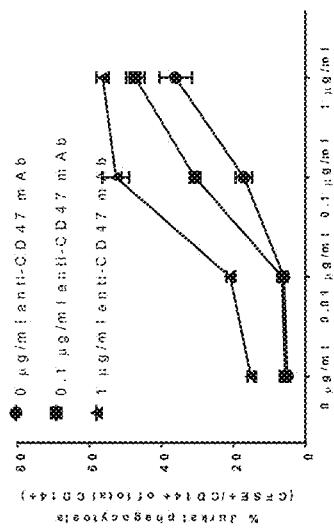
Figure 8J:
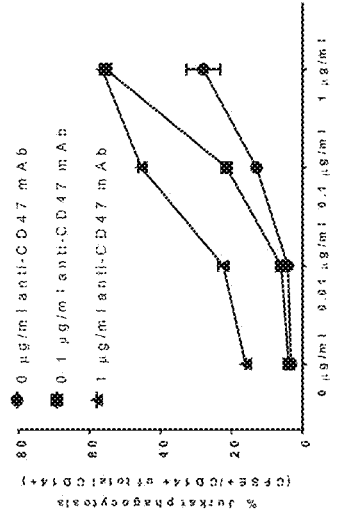
Figure 9B:
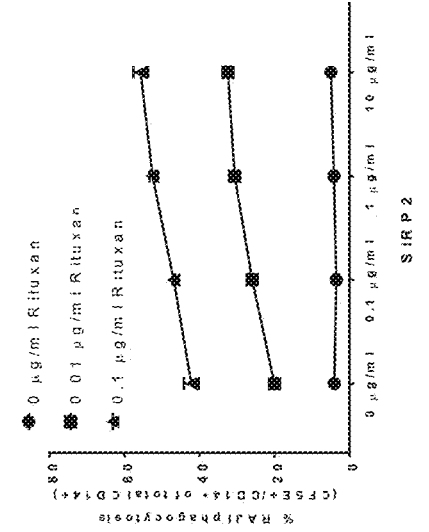
FIG. 9A-FIG. 9D. Anti-SIRP antibodies enhance phagocytosis in combination with anti-CD20 antibodies. Human macrophages were plated at a concentration of $3\times10^4$ cells per well in a 96 well plate and allowed to adhere for 24 hours. $8\times10^4$ CFSE (1 µM) labeled human RAJI lymphoma cells and increasing concentrations of anti-SIRP antibodies alone, the anti-CD20 antibody Rituxan alone, or a combination of anti-SIRP antibodies and Rituxan were added to the macrophage cultures and incubated at 37° C. for 3 hours. Non-phagocytosed RAJI cells were removed and macrophage cultures were washed. Macrophages were trypsinized and stained for CD14. Flow cytometry was used to determine the percentage of $CD14^+$/$CFSE^+$ cells in the total $CD14^+$ population.
Figure 9D:
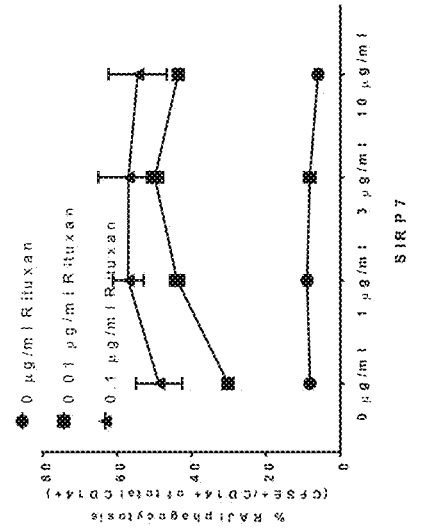
Figure 9A:
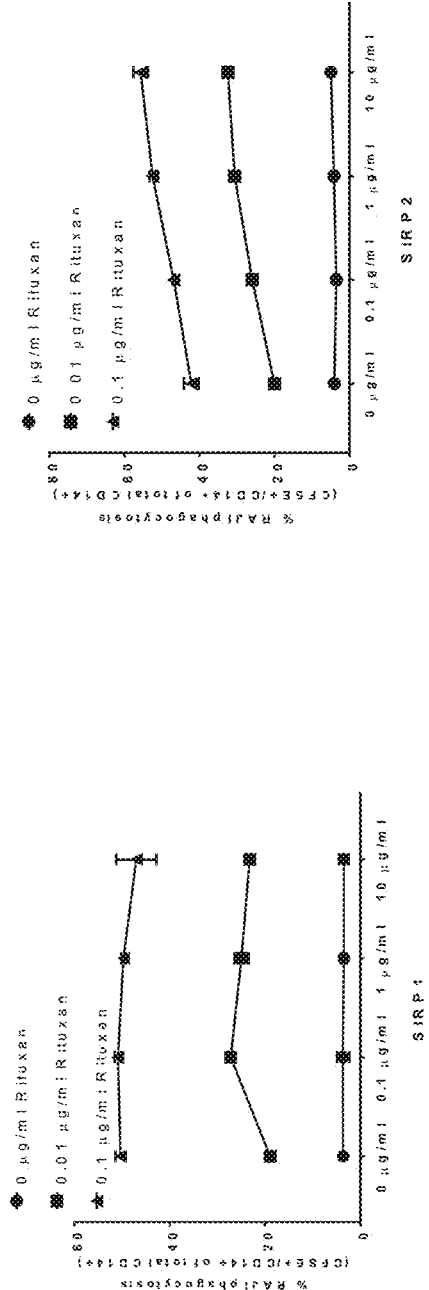
Figure 9C:
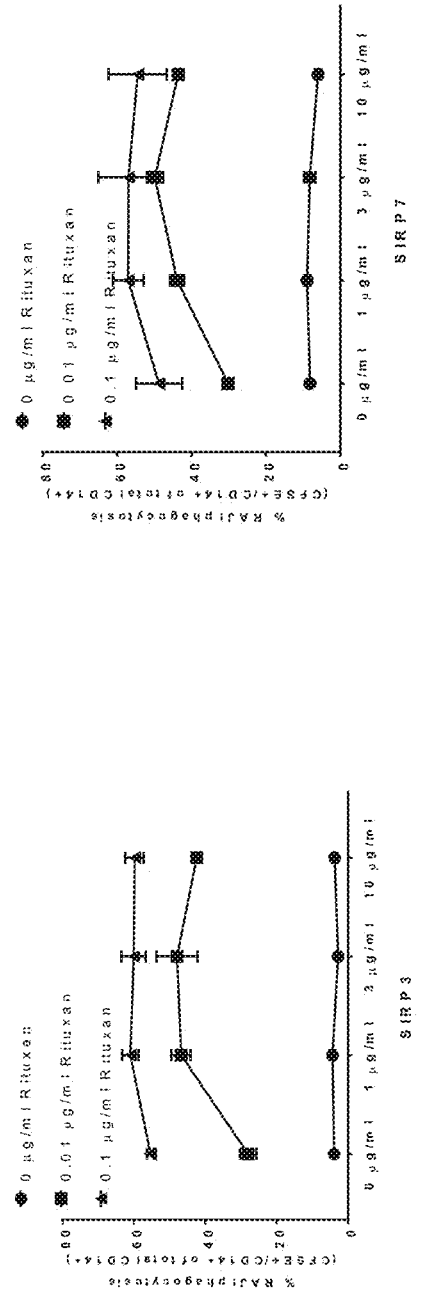

As shown in FIG. 7A and FIG. 7B, the soluble anti-SIRP mAbs SIRP4, SIRP9, SIRP11, SIRP12, SIRP13, SIRP14, SIRP15, SIRP16, SIRP17, SIRP18, SIRP19, SIRP20, SIRP21, SIRP22 and SIRP23 induced phagocytosis of Jurkat cells by human macrophages as compared to a murine IgG1 control antibody (Biolegend). In contrast, soluble anti-SIRP mAbs SIRP1, SIRP2, SIRP3, SIRP7, SIRP8 and SIRP10 did not induce the phagocytosis of Jurkat cells by human macrophages.

Example 9

Anti-SIRP mAbs Induce Phagocytosis when Combined with an Anti-CD47 Antibody

To assess the effect of anti-SIRP mAbs and anti-CD47 mAbs in combination on inducing phagocytosis of tumor cells by macrophages in vitro the following method was employed using flow cytometry.

Human monocyte-derived macrophages were derived from leukapheresis of healthy human peripheral blood and incubated in AIM-V media (Life Technologies) supplemented with 50 ng/ml M-CSF (Biolegend) for seven days. For the in vitro phagocytosis assay, macrophages were re-plated at a concentration of $3\times10^4$ cells per well in 100 µl of AIM-V media supplemented with 50 ng/ml M-CSF in a 96-well plate and allowed to adhere for 24 hours. Once the effector macrophages adhered to the culture dish, the targeted human cancer cells (Jurkat) were labeled with 1 µM 5(6)-Carboxyfluorescein diacetate N-succinimidyl ester (CFSE; Sigma Aldrich) and added to the macrophage cultures at a concentration of $8\times10^4$ cells in 100 µl of AIM-V media without supplements. Anti-SIRP mAbs alone, an anti-CD47 mAb (known to induce phagocytosis) alone, or anti-SIRP and anti-CD47 mAbs together were added at various concentrations immediately upon mixture of target and effector cells and allowed to incubate at 37° C. for 3 hours. After 3 hours, all non-phagocytosed cells were removed, and the remaining cells washed three times with PBS. Cells were then incubated in Accutase (Stemcell Technologies) to detach macrophages, collected into microcentrifuge tubes, and incubated in 100 ng of allophycocyanin (APC) labeled CD14 antibodies (BD biosciences) for 30 minutes, washed once, and analyzed by flow cytometry (Attune, Life Technologies) for the percentage of $CD14^+$ cells that were also $CFSE^+$ indicating complete phagocytosis.

As shown in FIG. 8A-FIG. 8J, all soluble anti-SIRP mAbs SIRP1, SIRP2, SIRP3, SIRP4, SIRP5, SIRP7, SIRP12, SIRP20, SIRP21 and SIRP22 increase phagocytosis of Jurkat cells by human macrophages to a greater degree when combined with anti-CD47 mAbs compared to either agent alone.

Example 10

Anti-SIRP mAbs Induce Phagocytosis in Combination with Rituxan

To assess the effect of anti-SIRP mAbs and anti-CD20 mAbs in combination on inducing phagocytosis of tumor cells by macrophages in vitro the following method was employed using flow cytometry.

Human monocyte-derived macrophages were derived from leukapheresis of healthy human peripheral blood and incubated in AIM-V media (Life Technologies) supplemented with 50 ng/ml M-CSF (Biolegend) for seven days. For the in vitro phagocytosis assay, macrophages were re-plated at a concentration of $3\times10^4$ cells per well in 100 µl of AIM-V media supplemented with 50 ng/ml M-CSF in a 96-well plate and allowed to adhere for 24 hours. Once the effector macrophages adhered to the culture dish, the targeted human cancer cells (RAJI) were labeled with 1 µM 5(6)-Carboxyfluorescein diacetate N-succinimidyl ester (CFSE; Sigma Aldrich) and added to the macrophage cultures at a concentration of $8\times10^4$ cells in 100 µl of AIM-V media without supplements. Anti-SIRP mAbs alone, an anti-CD20 mAb (Rituxan, Roche) alone, or anti-SIRP and anti-CD20 mAbs together were added at various concentrations immediately upon mixture of target and effector cells and allowed to incubate at 37° C. for 3 hours. After 3 hours, all non-phagocytosed cells were removed, and the remaining cells washed three times with PBS. Cells were then incubated in Accutase (Stemcell Technologies) to detach macrophages, collected into microcentrifuge tubes, and incubated in 100 ng of allophycocyanin (APC) labeled CD14 antibodies (BD biosciences) for 30 minutes, washed once, and analyzed by flow cytometry (Attune, Life Technologies) for the percentage of $CD14^+$ cells that were also $CFSE^+$ indicating complete phagocytosis.

As shown in FIG. 9A-FIG. 9D, all soluble anti-SIRP mAbs SIRP1, SIRP2, SIRP3, and SIRP7 increased phagocytosis of RAJI cells by human macrophages to a greater degree when combined with anti-CD20 mAbs compared to either agent alone.

Example 11

Anti-SIRP mAbs Induce Phagocytosis in Combination with Erbitux and Avelumab

To assess the effect of anti-SIRP mAbs and anti-EGFR mAbs or anti-PD-L1 mAbs in combination on inducing phagocytosis of tumor cells by macrophages in vitro the following method was employed using flow cytometry.

Human monocyte-derived macrophages were derived from leukapheresis of healthy human peripheral blood and incubated in AIM-V media (Life Technologies) supplemented with 50 ng/ml M-CSF (Biolegend) for seven days. For the in vitro phagocytosis assay, macrophages were re-plated at a concentration of $3\times10^4$ cells per well in 100 µl of AIM-V media supplemented with 50 ng/ml M-CSF in a 96-well plate and allowed to adhere for 24 hours. Once the effector macrophages adhered to the culture dish, the targeted human cancer cells (FaDu or ES-2) were labeled with 1 µM 5(6)-Carboxyfluorescein diacetate N-succinimidyl ester (CF SE; Sigma Aldrich) and added to the macrophage cultures at a concentration of $8\times10^4$ cells in 100 µl of AIM-V media without supplements. Anti-SIRP mAbs alone, an anti-EGFR mAb (Erbitux, Bristol-Myers Squibb) alone, an anti-PD-L1 mAb (Avelumab, Pfizer), or anti-SIRP and anti-EGFR mAbs together were added at various concentrations immediately upon mixture of target and effector cells and allowed to incubate at 37° C. for 3 hours. After 3 hours, all non-phagocytosed cells were removed, and the remaining cells washed three times with PBS. Cells were then incubated in Accutase (Stemcell Technologies) to detach macrophages, collected into microcentrifuge tubes, and incubated in 100 ng of allophycocyanin (APC) labeled CD14 antibodies (BD biosciences) for 30 minutes, washed once, and analyzed by flow cytometry (Attune, Life Technologies) for the percentage of $CD14^+$ cells that were also $CFSE^+$ indicating complete phagocytosis.

Figure 10A:
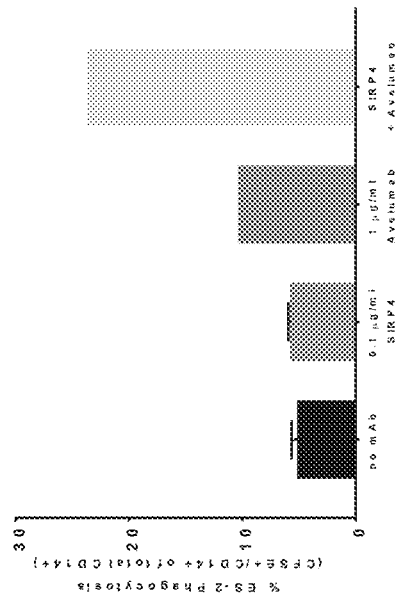
FIG. 10A-FIG. 10B. Anti-SIRP antibodies enhance phagocytosis in combination with anti-EGFR and anti-PD-L1 antibodies. Human macrophages were plated at a concentration of $3\times10^4$ cells per well in a 96 well plate and allowed to adhere for 24 hours. $8\times10^4$ CFSE (1 µM) labeled human FaDu HNSCC and increasing concentrations of anti-SIRP antibodies alone, the anti-EGFR antibody Erbitux alone, or anti-SIRP antibodies in combination with Erbitux or in combination with Avelumab were added to the macrophage cultures and incubated at 37° C. for 3 hours. Non-phagocytosed FaDu cells were removed and macrophage cultures were washed. Macrophages were trypsinized and stained for CD14. Flow cytometry was used to determine the percentage of CD14$^+$/CFSE$^+$ cells in the total CD14$^+$ population.
Figure 10B:
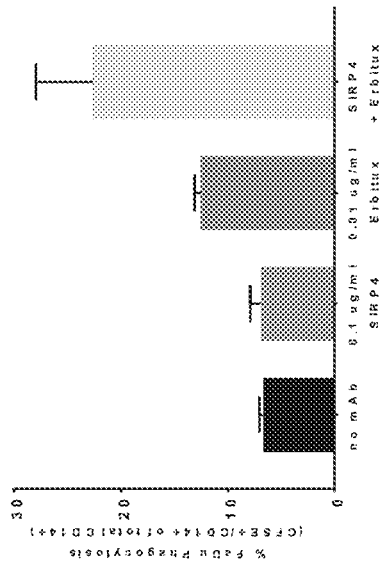

As shown in FIG. 10A, soluble anti-SIRP mAb SIRP4 increased phagocytosis of FaDu cells by human macrophages to a greater degree when combined with anti-EGFR mAbs compared to either agent alone. As shown in FIG. 10B, soluble anti-SIRP mAb SIRP4 increased phagocytosis of ES-2 cells by human macrophages to a greater degree when combined with anti-PD-L1 mAbs compared to either agent alone.

Example 12

Anti-SIRP mAbs Bind to Human Macrophages and Dendritic Cells

To assess the binding of anti-SIRP mAbs to cells expressing SIRPα such as human macrophages and dendritic cells the following method was employed using flow cytometry.

Human CD14+ monocytes, isolated from peripheral blood mononuclear cells (Astarte Biologics) were differentiated in vitro for seven days into macrophages or dendritic cells. For macrophage differentiation, monocytes were incubated in AIM-V media (Life Technologies) supplemented with 50 ng/ml M-CSF (Biolegend) for seven days. For dendritic cell differentiation, monocytes were incubated in AIM-V media (Life Technologies) in the presence of 10% human AB serum (Valley Biomedical), 200 ng/ml GM-CSF (Biolegend) and 50 ng/ml IL-4 (Biolegend). The cells were incubated for 1 h at 37° C., 5% $CO_2$ with serial dilutions of SIRP mAbs in binding buffer containing 1 mM EDTA (Sigma Aldrich) and 1% FBS (Biowest) in PBS (Corning). The cells were then washed and stained for 45 min under the same conditions with donkey anti-mouse IgG fluorescein isothiocyanate (FITC)-linked secondary antibody (Jackson ImmunoResearch Laboratories). The cells were subsequently stained with anti-CD14 or anti-CD11c conjugated to Alexa Fluor 647 fluorophore (Life Technologies and Biolegend, respectively) for 30 min on ice, washed and analyzed by flow cytometry (Attune, Life Technologies). Binding was assessed as the median FITC fluorescence intensity of CD14+ or CD11c+ cells, subtracted from cells stained with the secondary antibody only.

Figure 11:
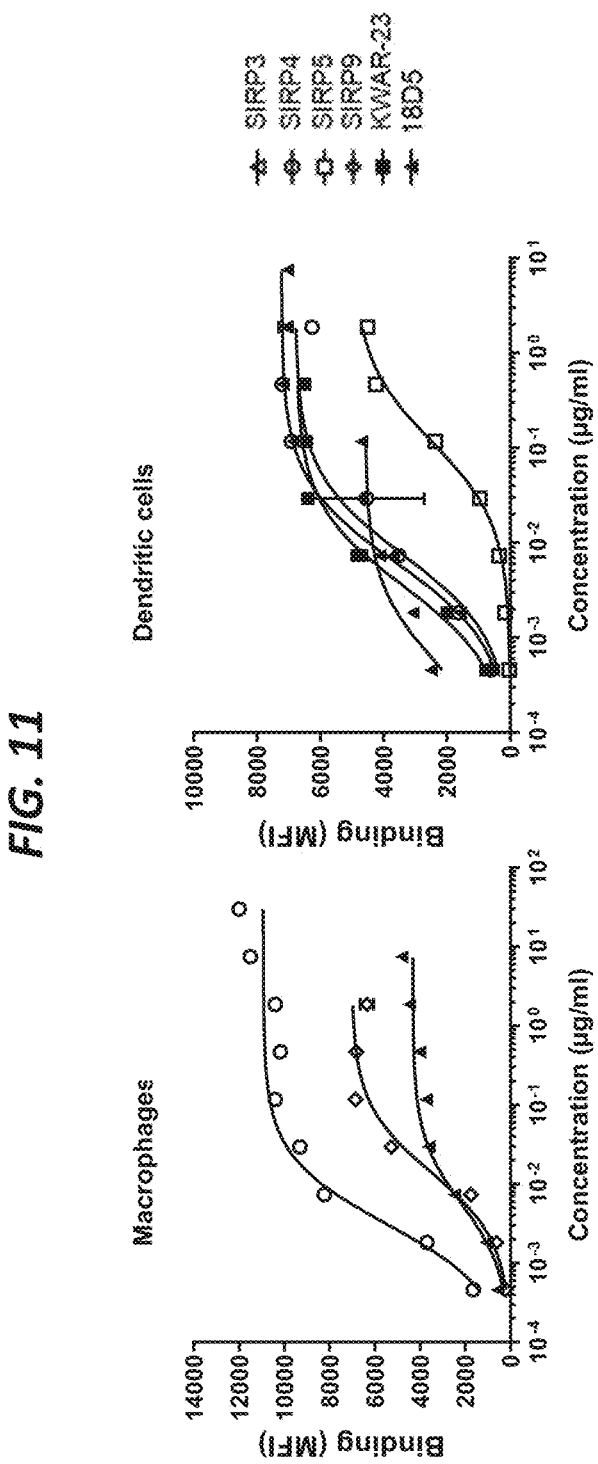
FIG. 11. Anti-SIRP antibodies bind to SIRPα on macrophages and dendritic cells. Binding of anti-SIRP antibodies to human macrophages or dendritic cells was determined. Human monocyte-derived macrophages were incubated with increasing concentrations of anti-SIRP antibodies for 1 hr. The cells were washed and then incubated with AF647-labelled secondary antibody for 45 min, washed and antibody binding measured using flow cytometry.

As shown in Table 5, the soluble anti-SIRP mAbs SIRP3, SIRP4, SIRP5 and SIRP9, as well as OSE-18D5 and KWAR-23, bound to cell-expressed SIRPα on dendritic cells and/or macrophages with apparent affinities in the picomolar range. FIG. 11 demonstrates representative binding curves derived from the antibodies of the present disclosure.

TABLE 5

Binding of anti-SIRP mAbs to Human Cells Expressing SIRPα.

|  | Human macrophage binding $K_d$ (pM) | Human dendritic cell binding $K_d$ (pM) |
| --- | --- | --- |
| SIRP3 | ND* | 3.47 |
| SIRP4 | 20.7 | 50 |
| SIRP5 | ND* | 770 |
| SIRP9 | 93.7 | ND* |
| 18D5 | 37.3 | 41.2 |
| KWAR-23 | ND* | 23.4 |

*Not Determined

Example 13

Anti-SIRP mAbs Exhibit Variable Binding to Human CD3+ T Cells

To assess the binding of anti-SIRP mAbs on human CD3 T cells the following method was employed using flow cytometry.

Human CD3 T cells, isolated from peripheral blood mononuclear cells (Astarte Biologics) were incubated in 96-well V-bottom plates at 2.5 \ 10$^5$ cells/well for 1 h at 37° C., 5% $CO_2$ with serial dilutions of SIRP mAbs in binding buffer containing 1 mM EDTA (Sigma Aldrich), 1% FBS (Biowest) in PBS (Corning). The cells were then washed and stained for 45 min under the same conditions with donkey anti-mouse IgG fluorescein isothiocyanate (FITC)-linked secondary antibody (Jackson ImmunoResearch Laboratories). The cells were subsequently stained with anti-CD3 conjugated to 3-carboxy-6,8-difluoro-7-hydroxycoumarin (Pacific Blue) fluorophore (BioLegend) for 30 min on ice, washed and analyzed by flow cytometry (Attune, Life Technologies). Binding was assessed as the median FITC fluorescence intensity of CD3+ cells, subtracted from CD3+ cells stained with the secondary antibody only. All SIRP antibodies were generated in-house except for LSB2.20 (BioLegend). For activated T cells, prior to the binding assay CD3 T cells were activated for 72 h in a 96-well flat-bottom plate coated with 10 μg/ml anti-CD3 (clone UCHT1; BioLegend), at 1×10$^5$ cells/well in the presence of 0.5 μg/ml anti-CD28 (clone CD28.2; BioLegend).

Figures 12A, 12B, 12C:
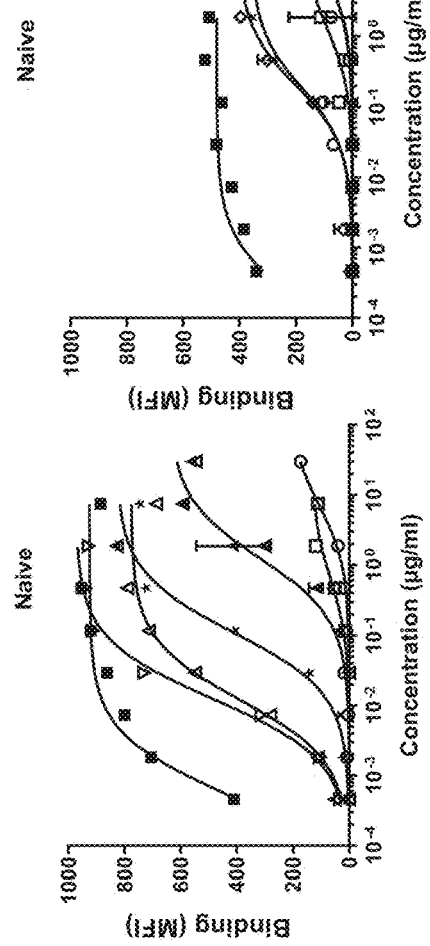
FIG. 12A-FIG. 12C. Anti-SIRP antibodies bind to SIRPγ on naïve and activated T cells. Binding of anti-SIRP antibodies to naïve T cells (FIG. 12A and FIG. 12B) or activated T cells (FIG. 12C) following 3-day activation on anti-CD3 coated plates was determined by flow cytometry. T cells were incubated with increasing concentrations of anti-SIRP antibodies for 1 h, cells were washed and FITC-labelled anti-mouse secondary antibody was added for 1 hr. Cells were washed and antibody binding measured using flow cytometry.

As shown in Table 6, the soluble SIRP3, SIRP7, SIRP9, KWAR-23, and the SIRPγ-specific antibody LSB2.20 bind T cells with affinities in the picomolar range. The affinities of anti-SIRP mAbs SIRP4, SIRP5 and OSE-18D5 are much lower and are in the nanomolar range. FIG. 12A, FIG. 12B, and FIG. 12C demonstrate representative binding curves derived from antibodies of the present disclosure.

TABLE 6

Binding of anti-SIRP Antibodies to Human T Cells Expressing SIRPγ.

|  | Human T cell binding $K_d$ (pM) Naive | Human T cell binding $K_d$ (pM) Naive | Human T cell binding $K_d$ (pM) Activated |
| --- | --- | --- | --- |
| SIRP3 | 80.7 | ND | ND |
| SIRP4 | NC* | NC* | NC* |
| SIRP5 | NC* | NC* | NC* |
| SIRP7 | 83.9 | ND | ND |
| SIRP9 | ND | 1410 | 263 |
| 18D5 | 8410 | NC* | NC* |
| KWAR-23 | 4.04 | 1.59 | 6.22 |
| LSB2.20 | 750 | 1260 | 950 |

*NC Not calculated; mean fluorescence intensities were comparable to the mIgG1 background level
**Not determined.

Example 14

Anti-SIRP mAbs do not Block Soluble CD47/Cellular SIRPγ Binding

To assess the effect of anti-SIRP antibodies of the present disclosure on blocking the binding of soluble CD47 to cells expressing SIRPγ, the following method was employed using soluble human IgG1 Fc tagged human CD47.

Human T-ALL cells (Jurkat) were incubated at 2.5×10$^5$ cells/well for 1 h at 37° C., $CO_2$ with 10 μg/ml of anti-SIRP mAbs in binding buffer containing 1 mM EDTA (Sigma Aldrich), 1% FBS (Biowest) in PBS (Corning). Following this, soluble human IgG1 Fc tagged human CD47 (ACRO #CD7-H5256) was added for a final concentration of 50 μg/ml and the cells incubated as previously for another 1 h. The cells were then washed extensively and stained for 45 min under the same conditions with donkey anti-human antibody conjugated to Alexa Fluor 647 (Jackson ImmunoResearch). The samples were analyzed by flow cytometry (Attune, Life Technologies). For analysis, background human IgG1 Fc staining in the absence of soluble Fc tagged CD47 was subtracted from median Alexa Fluor 647 fluorescence intensity. Blocking was assessed as the reduction in background-corrected median fluorescence intensity of Alexa Fluor 647 in the presence of SIRP mAbs compared to murine IgG1 (Biolegend, MOPC-21) control.

As shown in Table 7, the soluble anti-SIRP mAbs SIRP4, SIRP9, and OSE 18D5 do not block the binding of cell expressed SIRPγ to soluble human CD47. KWAR-23 does block the binding of Jurkat cell expressed SIRPγ to soluble human CD47.

TABLE 7

Blocking of CD47/SIRPγ Binding by anti-SIRP Antibodies.

| | Blocking of soluble CD47 binding to SIRPγ on Jurkat |
|---|---|
| SIRP4 | Non-blocking |
| SIRP9 | Non-blocking |
| OSE 18D5 | Non-blocking |
| KWAR-23 | Blocking |

Example 15

Anti-SIRP mAbs Block Soluble CD47/Cellular SIRPα Binding

To assess the effect of anti-SIRP antibodies of the present disclosure on binding of soluble CD47 to cells expressing SIRPα, the following method was employed using human macrophages and soluble human IgG1 Fc tagged human CD47.

Human CD14+ monocytes, isolated from peripheral blood mononuclear cells (Astarte Biologics) were differentiated in vitro for seven days in AIM-V media (Life Technologies) supplemented with 50 ng/ml M-CSF (Biolegend). Macrophage Fc receptors were then blocked with human Fc receptor blocking solution (Biolegend) for 20 min at room temperature. The cells were then washed and incubated for 1 h at 37° C., 5% $CO_2$ with 10 μg/ml of anti-SIRP mAbs in binding buffer containing 1 mM EDTA (Sigma Aldrich), 1% FBS (Biowest) in PBS (Corning). Following this, soluble human IgG1 Fc tagged human CD47 (ACRO #CD7-H5256) was added for a final concentration of 20 μg/ml and the cells incubated as previously for another 1 h. The cells were then washed extensively and stained for 45 min under the same conditions with donkey anti-human antibody conjugated to Alexa Fluor 647 (Jackson ImmunoResearch). The samples were analyzed by flow cytometry (Attune, Life Technologies). For analysis, background human IgG1 Fc staining in the absence of soluble Fc tagged CD47 was subtracted from median Alexa Fluor 647 fluorescence intensity. Blocking was assessed as the reduction in background-corrected median fluorescence intensity of Alexa Fluor 647 in the presence of SIRP mAbs compared to murine IgG1 (Biolegend, MOPC-21) control. Four different monocyte donors were used in these assays with a minimum of three donors per antibody tested.

Figure 13:
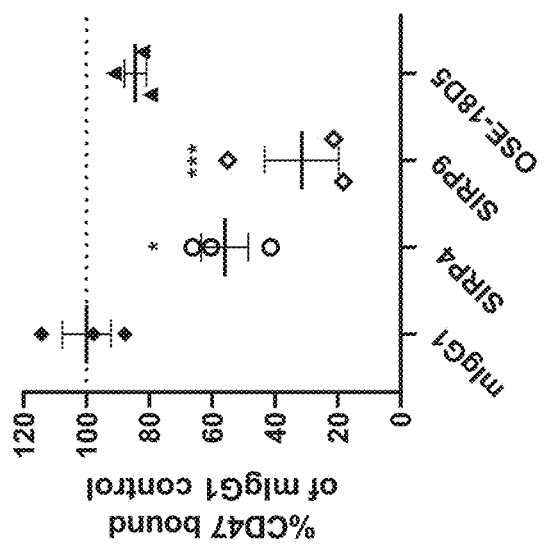
FIG. 13. Blocking of human CD47/SIRPα binding by anti-SIRP antibodies on macrophages. The ability of anti-SIRP antibodies to block the interaction between recombinant human CD47 and macrophage expressed SIRPα was determined by flow cytometry. The Fc receptors on macrophages were blocked prior to incubation with 10 μg/ml of the anti-SIRP antibodies. Binding of soluble Fc tagged human CD47 (20 μg/ml) was measured using AF647-tagged anti-human secondary antibody.

As shown in FIG. 13, the soluble anti-SIRP mAbs SIRP4 and SIRP9 block the binding of cell expressed SIRPα on macrophages to soluble human CD47. The OSE 18D5 mAb does not block the binding of cell expressed SIRPα to soluble human CD47.

Example 16

Anti-SIRP mAbs do not Inhibit T Cell Proliferation

To assess the effect of anti-SIRP mAbs on allogeneic dendritic cell-induced T cell proliferation in vitro the following method was employed using flow cytometry.

Human monocyte-derived dendritic cells were generated by incubating CD14+ monocytes (Astarte Biologics) in AIM-V medium (Life Technologies) supplemented with 10% human AB serum (Valley Biomedical), 200 ng/ml GM-CSF (Biolegend) and 50 ng/ml IL-4 (Biolegend) for six days, with addition of fresh, cytokine replete medium on Day 2. For the allogeneic dendritic cell and T cell co-culture assay, immature dendritic cells were re-plated onto a 96-well plate at a concentration of $1 \times 10^5$ cells per well. CellTrace™ Violet (Life Technologies) fluorescent cell proliferation dye-labelled allogeneic healthy donor derived CD3+ T cells from four different donors (Astarte Biologics) were added to the culture at a 1:5 DC: T cell ratio. Anti-SIRP mAbs were added immediately at the saturating concentration of 10 μg/ml immediately and the cells incubated at 37° C., 5% $CO_2$ for 6-7 days in a total volume of 200 μl. Cells were then detached by scraping the wells with pipette tips and washed in fluorescence-activated cell sorting buffer (1% FBS, Biowest, in PBS). Cells were then incubated with PerCP-Cy5.5 fluorescent dye labelled CD3 antibody (Biolegend) for 30 minutes on ice, washed once, and analyzed by flow cytometry (Attune, Life Technologies). T cell proliferation was measured by the dilution of the CellTrace™ Violet dye within the CD3+ cell population.

Figure 14B:
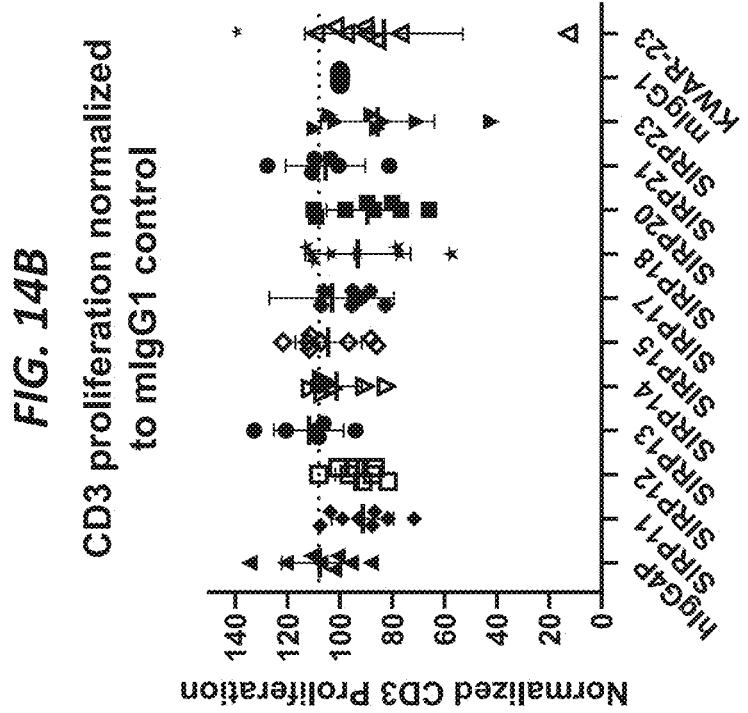
FIG. 14A-FIG. 14B. Anti-SIRP antibodies do not inhibit T cell proliferation upon allogeneic dendritic cell stimulation. Effect of anti-SIRP antibodies on proliferation of T cells was determined by activating CellTrace Violet labelled human CD3 T cells with allogeneic human monocyte-derived dendritic cells at a 1:5 T cell:DC ratio in the presence of 10 μg/ml anti-SIRP antibodies. Flow cytometry was used to determine the percentage of proliferated CD3 T cells following 6-7-day co-culture. The dotted line represents proliferation of hIgG4P control.
Figure 14A:
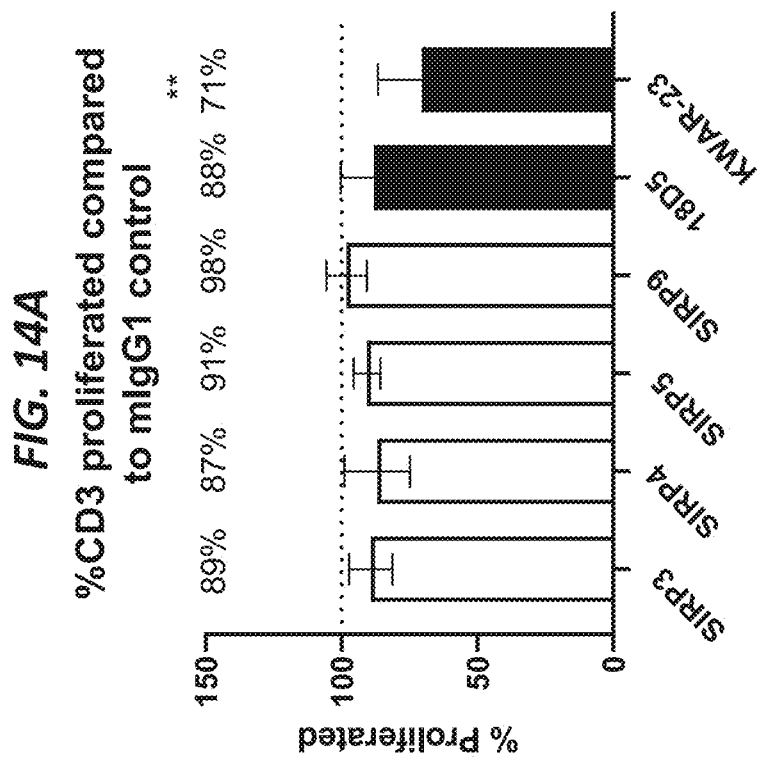

As shown in FIG. 14A and FIG. 14B, the anti-SIRP mAbs SIRP3, SIRP4, SIRP5, SIRP9, SIRP11, SIRP12, SIRP13, SIRP14, SIRP15, SIRP17, SIRP18, SIRP20, SIRP21, SIRP23 and OSE-18D5 had no significant effect on T cell proliferation compared to control antibody (Biolegend). In contrast, KWAR-23, which blocks both SIRPα and SIRPγ binding to CD47, inhibited T cell proliferation.

Example 17

Anti-SIRP mAbs do not Inhibit Antigen-Specific T Cell Recall Response

To assess the effect of anti-SIRP mAbs on antigen recall response in T cells in vitro the following method was employed using flow cytometry.

Human peripheral blood mononuclear cells from a cytomegalovirus seropositive donor (Astarte Biologics) were labelled with CellTrace™ Violet (Life Technologies) fluorescent cell proliferation dye and seeded at 200,000 cells/well in a 96-well plate. The cells were then incubated with different concentrations of cytomegalovirus antigen (Astarte Biologics) in AIM-V medium (Life Technologies) supplemented with 10% human AB serum (Valley Biomedical), which induces an antigen dependent stimulation of T cell proliferation. Anti-SIRP mAbs as well as an anti-CD47 mAb, clone B6H12, (Biolegend) were added immediately at the saturating concentration of 10 μg/ml immediately and the cells incubated at 37° C., 5% $CO_2$ for five days. T cell proliferation was measured by the dilution of the CellTrace™ Violet dye within the CD4+ cell population.

Figure 15:
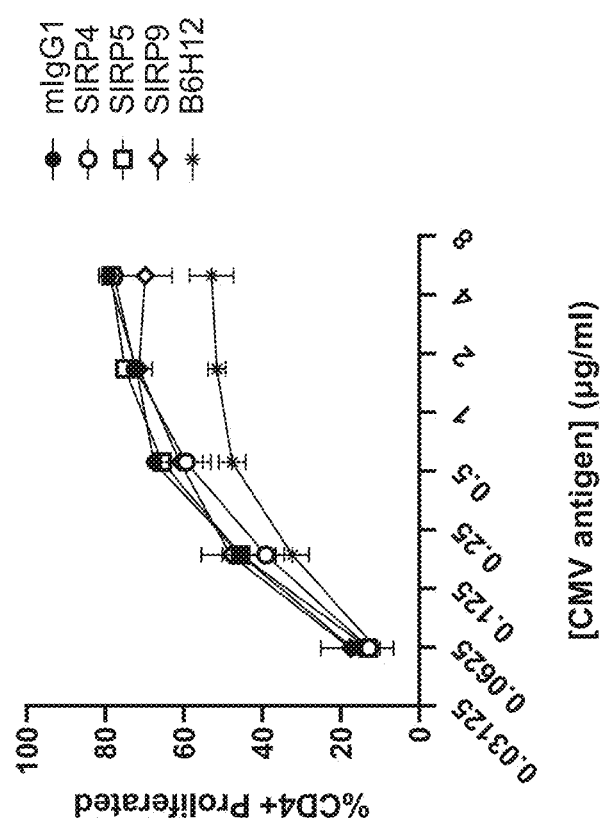
FIG. 15. Anti-SIRP antibodies do not inhibit antigen recall response. Effect of anti-SIRP antibodies on T cell antigen recall responses was assessed using PBMC from human cytomegalovirus seropositive donor. CellTrace Violet dye-labelled PBMC were incubated with 10 μg/ml of anti-SIRP antibodies in the presence of increasing concentratons of CMV antigen for 5 days. T cell proliferation was determined by the dilution of the CellTrace Violet dye within the CD4+ T cell population using flow cytometry.

As shown in FIG. 15, the soluble anti-SIRP mAbs SIRP4, SIRP5 and SIRP9 did not inhibit the ability of T cells to elicit a CMV antigen recall response. In contrast, the anti-CD47 antibody clone B6H12, which is known to inhibit T cell responses, reduced T cell proliferation compared to murine IgG1 control antibody (Biolegend).

Example 18

| Antibody | LCDR1 (SEQ ID NO:) | LCDR2 (SEQ ID NO:) | LCDR3 (SEQ ID NO:) | HCDR1 (SEQ ID NO:) | HCDR2 (SEQ ID NO:) | HCDR3 (SEQ ID NO:) |
|---|---|---|---|---|---|---|
| SIRP1 | 1 | 2 | 3 | 33 | 34 | 35 |
| SIRP2 | 4 | 5 | 6 | 36 | 37 | 38 |
| SIRP3 | 7 | 8 | 9 | 39 | 40 | 41 |
| SIRP4 | 10 | 11 | 12 | 42 | 43 | 44 |
| SIRP5 | 13 | 14 | 15 | 45 | 46 | 47 |
| SIRP6 | 16 | 17 | 18 | 48 | 49 | 50 |
| SIRP7 | 19 | 20 | 21 | 51 | 52 | 53 |
| SIRP8 | 22 | 23 | 24 | 54 | 55 | 56 |
| SIRP9 | 25 | 26 | 27 | 57 | 58 | 59 |
| SIRP10 | 28 | 29 | 30 | 60 | 61 | 62 |
| SIRP11 | 10 | 31 | 12 | 42 | 43 | 44 |
| SIRP12 | 10 | 31 | 12 | 42 | 43 | 44 |
| SIRP13 | 10 | 31 | 32 | 42 | 43 | 44 |
| SIRP14 | 10 | 31 | 12 | 42 | 43 | 44 |
| SIRP15 | 10 | 31 | 12 | 42 | 43 | 44 |
| SIRP16 | 10 | 31 | 32 | 42 | 43 | 44 |
| SIRP17 | 10 | 31 | 12 | 42 | 43 | 44 |
| SIRP18 | 10 | 31 | 12 | 42 | 43 | 44 |
| SIRP19 | 10 | 31 | 32 | 42 | 43 | 44 |
| SIRP20 | 10 | 31 | 12 | 42 | 43 | 44 |
| SIRP21 | 10 | 31 | 12 | 42 | 43 | 44 |
| SIRP22 | 10 | 31 | 32 | 42 | 43 | 44 |
| SIRP23 | 10 | 11 | 12 | 42 | 43 | 44 |
| SIRP24 | 25 | 26 | 27 | 57 | 58 | 63 |
| SIRP25 | 25 | 26 | 27 | 57 | 58 | 63 |
| SIRP26 | 25 | 26 | 27 | 57 | 58 | 63 |
| SIRP27 | 25 | 26 | 27 | 57 | 58 | 63 |
| SIRP28 | 25 | 26 | 27 | 57 | 58 | 63 |
| SIRP29 | 25 | 26 | 27 | 57 | 58 | 63 |
| SIRP30 | 25 | 26 | 27 | 57 | 58 | 59 |
| SIRP31 | 25 | 26 | 27 | 57 | 58 | 59 |
| SIRP32 | 25 | 26 | 27 | 57 | 58 | 59 |
| SIRP33 | 25 | 26 | 27 | 57 | 58 | 63 |

| | $V_L$ (SEQ ID NO:) | $V_H$ (SEQ ID NO:) | LC (SEQ ID NO:) | HC (SEQ ID NO:) |
|---|---|---|---|---|
| SIRP1 | 64 | 81 | 98 | 109 |
| SIRP2 | 65 | 82 | 99 | 110 |
| SIRP3 | 66 | 83 | 100 | 111 |
| SIRP4 | 67 | 84 | | |
| SIRP5 | 68 | 85 | | |
| SIRP6 | 69 | 86 | | |
| SIRP7 | 70 | 87 | | |
| SIRP8 | 71 | 88 | | |
| SIRP9 | 72 | 89 | | |
| SIRP10 | 73 | 90 | | |
| SIRP11 | 74 | 91 | 101 | 112 |
| SIRP12 | 75 | 91 | 102 | 112 |
| SIRP13 | 76 | 91 | 103 | 112 |
| SIRP14 | 74 | 92 | 101 | 113 |
| SIRP15 | 75 | 92 | 102 | 113 |
| SIRP16 | 76 | 92 | 103 | 113 |
| SIRP17 | 74 | 93 | 101 | 114 |
| SIRP18 | 75 | 93 | 102 | 114 |
| SIRP19 | 76 | 93 | 103 | 114 |
| SIRP20 | 74 | 94 | 101 | 115 |
| SIRP21 | 75 | 94 | 102 | 115 |
| SIRP22 | 76 | 94 | 103 | 115 |
| SIRP23 | 77 | 84 | 104 | 116 |
| SIRP24 | 78 | 95 | 105 | 117 |
| SIRP25 | 79 | 95 | 106 | 117 |
| SIRP26 | 80 | 95 | 107 | 117 |
| SIRP27 | 78 | 96 | 105 | 118 |
| SIRP28 | 79 | 96 | 106 | 118 |
| SIRP29 | 80 | 96 | 107 | 118 |
| SIRP30 | 78 | 97 | 105 | 119 |
| SIRP31 | 79 | 97 | 106 | 119 |
| SIRP32 | 80 | 97 | 107 | 119 |
| SIRP33 | 72 | 89 | 108 | 120 |

We claim:

1. A monoclonal antibody or antigen binding fragment thereof which specifically binds human SIRPα, wherein the monoclonal antibody or antigen binding fragment comprises three light-chain complementarity determining regions (LCDR1, LCDR2, LCDR3) chosen from:
   i. SEQ ID NO:1, SEQ ID NO:2, SEQ ID NO:3;
   ii. SEQ ID NO:4, SEQ ID NO:5, SEQ ID NO:6;
   iii. SEQ ID NO:7, SEQ ID NO:8, SEQ ID NO:9;
   iv. SEQ ID NO:10, SEQ ID NO:11, SEQ ID NO:12;
   v. SEQ ID NO:13, SEQ ID NO:14, SEQ ID NO:15;
   vi. SEQ ID NO:16, SEQ ID NO:17, SEQ ID NO:18;
   vii. SEQ ID NO:19, SEQ ID NO:20, SEQ ID NO:21;
   viii. SEQ ID NO:22, SEQ ID NO:23, SEQ ID NO:24;
   ix. SEQ ID NO:25, SEQ ID NO:26, SEQ ID NO:27;
   x. SEQ ID NO:28, SEQ ID NO:29, SEQ ID NO:30;
   xi. SEQ ID NO:10, SEQ ID NO:31, SEQ ID NO:12;
   xii. SEQ ID NO:10, SEQ ID NO:31, SEQ ID NO:32;
   xiii. SEQ ID NO:25, SEQ ID NO:26, SEQ ID NO:27; and
   and three heavy-chain complementarity determining regions (HCDR1, HCDR2, HCDR3) chosen from:
   i. SEQ ID NO:33, SEQ ID NO:34, and SEQ ID NO:35;
   ii. SEQ ID NO:36, SEQ ID NO:37, and SEQ ID NO:38;
   iii. SEQ ID NO:39, SEQ ID NO:40, and SEQ ID NO:41;
   iv. SEQ ID NO:42, SEQ ID NO:43, and SEQ ID NO:44;
   v. SEQ ID NO:45, SEQ ID NO:46, and SEQ ID NO:47;
   vi. SEQ ID NO:48, SEQ ID NO:49, and SEQ ID NO:50;
   vii. SEQ ID NO:51, SEQ ID NO:52, and SEQ ID NO:53;
   viii. SEQ ID NO:54, SEQ ID NO:55, and SEQ ID NO:56;
   ix. SEQ ID NO:57, SEQ ID NO:58, and SEQ ID NO:59;
   x. SEQ ID NO:60, SEQ ID NO:61, and SEQ ID NO:62; and
   xi. SEQ ID NO:57, SEQ ID NO:58, and SEQ ID NO:63.

2. The monoclonal antibody or antigen binding fragment thereof of claim 1, wherein the monoclonal antibody or antigen binding fragment thereof is a chimeric or humanized antibody.

3. The monoclonal antibody or antigen binding fragment thereof of claim 1, comprising a heavy chain variable domain ($V_H$) and light chain variable domain ($V_L$) selected from:

i. a heavy chain variable domain comprising the amino acid sequence of SEQ ID NO:81 and a light chain variable domain comprising the amino acid sequence SEQ ID NO:64;
ii. a heavy chain variable domain comprising the amino acid sequence of SEQ ID NO:82 and a light chain variable domain comprising the amino acid sequence SEQ ID NO:65;
iii. a heavy chain variable domain comprising the amino acid sequence of SEQ ID NO:83 and a light chain variable domain comprising the amino acid sequence SEQ ID NO:66;
iv. a heavy chain variable domain comprising the amino acid sequence of SEQ ID NO:84 and a light chain variable domain comprising the amino acid sequence SEQ ID NO:67;
v. a heavy chain variable domain comprising the amino acid sequence of SEQ ID NO:85 and a light chain variable domain comprising the amino acid sequence SEQ ID NO:68;
vi. a heavy chain variable domain comprising the amino acid sequence of SEQ ID NO:86 and a light chain variable domain comprising the amino acid sequence SEQ ID NO:69;
vii. a heavy chain variable domain comprising the amino acid sequence of SEQ ID NO:87 and a light chain variable domain comprising the amino acid sequence SEQ ID NO:70;
viii. a heavy chain variable domain comprising the amino acid sequence of SEQ ID NO:88 and a light chain variable domain comprising the amino acid sequence SEQ ID NO:71;
ix. a heavy chain variable domain comprising the amino acid sequence of SEQ ID NO:89 and a light chain variable domain comprising the amino acid sequence SEQ ID NO:72;
x. a heavy chain variable domain comprising the amino acid sequence of SEQ ID NO:90 and a light chain variable domain comprising the amino acid sequence SEQ ID NO:73;

xi. a heavy chain variable domain comprising the amino acid sequence of SEQ ID NO:91 and a light chain variable domain comprising the amino acid sequence SEQ ID NO:74;
xii. a heavy chain variable domain comprising the amino acid sequence of SEQ ID NO:91 and a light chain variable domain comprising the amino acid sequence SEQ ID NO:75;
xiii. a heavy chain variable domain comprising the amino acid sequence of SEQ ID NO:91 and a light chain variable domain comprising the amino acid sequence SEQ ID NO:76;
xiv. a heavy chain variable domain comprising the amino acid sequence of SEQ ID NO:92 and a light chain variable domain comprising the amino acid sequence SEQ ID NO:74;
xv. a heavy chain variable domain comprising the amino acid sequence of SEQ ID NO:92 and a light chain variable domain comprising the amino acid sequence SEQ ID NO:75;
xvi. a heavy chain variable domain comprising the amino acid sequence of SEQ ID NO:92 and a light chain variable domain comprising the amino acid sequence SEQ ID NO:76;
xvii. a heavy chain variable domain comprising the amino acid sequence of SEQ ID NO:93 and a light chain variable domain comprising the amino acid sequence SEQ ID NO:74;
xviii. a heavy chain variable domain comprising the amino acid sequence of SEQ ID NO:93 and a light chain variable domain comprising the amino acid sequence SEQ ID NO:75;
xix. a heavy chain variable domain comprising the amino acid sequence of SEQ ID NO:93 and a light chain variable domain comprising the amino acid sequence SEQ ID NO:76;
xx. a heavy chain variable domain comprising the amino acid sequence of SEQ ID NO:94 and a light chain variable domain comprising the amino acid sequence SEQ ID NO:74;
xxi. a heavy chain variable domain comprising the amino acid sequence of SEQ ID NO:94 and a light chain variable domain comprising the amino acid sequence SEQ ID NO:75;
xxii. a heavy chain variable domain comprising the amino acid sequence of SEQ ID NO:94 and a light chain variable domain comprising the amino acid sequence SEQ ID NO:76;
xxiii. a heavy chain variable domain comprising the amino acid sequence of SEQ ID NO:84 and a light chain variable domain comprising the amino acid sequence SEQ ID NO:77;
xxiv. a heavy chain variable domain comprising the amino acid sequence of SEQ ID NO:95 and a light chain variable domain comprising the amino acid sequence SEQ ID NO:78;
xxv. a heavy chain variable domain comprising the amino acid sequence of SEQ ID NO:95 and a light chain variable domain comprising the amino acid sequence SEQ ID NO:79;
xxvi. a heavy chain variable domain comprising the amino acid sequence of SEQ ID NO:95 and a light chain variable domain comprising the amino acid sequence SEQ ID NO:80;
xxvii. a heavy chain variable domain comprising the amino acid sequence of SEQ ID NO:96 and a light chain variable domain comprising the amino acid sequence SEQ ID NO:78;
xxviii. a heavy chain variable domain comprising the amino acid sequence of SEQ ID NO:96 and a light chain variable domain comprising the amino acid sequence SEQ ID NO:79;
xxix. a heavy chain variable domain comprising the amino acid sequence of SEQ ID NO:96 and a light chain variable domain comprising the amino acid sequence SEQ ID NO:80;
xxx. a heavy chain variable domain comprising the amino acid sequence of SEQ ID NO:97 and a light chain variable domain comprising the amino acid sequence SEQ ID NO:78;
xxxi. a heavy chain variable domain comprising the amino acid sequence of SEQ ID NO:97 and a light chain variable domain comprising the amino acid sequence SEQ ID NO:79;
xxxii. a heavy chain variable domain comprising the amino acid sequence of SEQ ID NO:97 and a light chain variable domain comprising the amino acid sequence SEQ ID NO:80; and
xxxiii. a heavy chain variable domain comprising the amino acid sequence of SEQ ID NO:89 and a light chain variable domain comprising the amino acid sequence SEQ ID NO:72.

4. The monoclonal antibody or antigen binding fragment thereof of claim 3, comprising one heavy chain and one light chain selected from:
i. a heavy chain comprising the amino acid sequence of SEQ ID NO:109 and a light chain comprising the amino acid sequence SEQ ID NO:98;
ii. a heavy chain comprising the amino acid sequence of SEQ ID NO:110 and a light chain comprising the amino acid sequence SEQ ID NO:99;
iii. a heavy chain comprising the amino acid sequence of SEQ ID NO:111 and a light chain comprising the amino acid sequence SEQ ID NO:100;
iv. a heavy chain comprising the amino acid sequence of SEQ ID NO:112 and a light chain comprising the amino acid sequence SEQ ID NO:101;
v. a heavy chain comprising the amino acid sequence of SEQ ID NO:112 and a light chain comprising the amino acid sequence SEQ ID NO:102;
vi. a heavy chain comprising the amino acid sequence of SEQ ID NO:112 and a light chain comprising the amino acid sequence SEQ ID NO:103;
vii. a heavy chain comprising the amino acid sequence of SEQ ID NO:113 and a light chain comprising the amino acid sequence SEQ ID NO:101;
viii. a heavy chain comprising the amino acid sequence of SEQ ID NO:113 and a light chain comprising the amino acid sequence SEQ ID NO:102;
ix. a heavy chain comprising the amino acid sequence of SEQ ID NO:113 and a light chain comprising the amino acid sequence SEQ ID NO:103;
x. a heavy chain comprising the amino acid sequence of SEQ ID NO:114 and a light chain comprising the amino acid sequence SEQ ID NO:101;
xi. a heavy chain comprising the amino acid sequence of SEQ ID NO:114 and a light chain comprising the amino acid sequence SEQ ID NO:102;
xii. a heavy chain comprising the amino acid sequence of SEQ ID NO:114 and a light chain comprising the amino acid sequence SEQ ID NO:103;

xiii. a heavy chain comprising the amino acid sequence of SEQ ID NO:115 and a light chain comprising the amino acid sequence SEQ ID NO:101;

xiv. a heavy chain comprising the amino acid sequence of SEQ ID NO:115 and a light chain comprising the amino acid sequence SEQ ID NO:102;

xv. a heavy chain comprising the amino acid sequence of SEQ ID NO:115 and a light chain comprising the amino acid sequence SEQ ID NO:103;

xvi. a heavy chain comprising the amino acid sequence of SEQ ID NO:116 and a light chain comprising the amino acid sequence SEQ ID NO:104;

xvii. a heavy chain comprising the amino acid sequence of SEQ ID NO:117 and a light chain comprising the amino acid sequence SEQ ID NO:105;

xviii. a heavy chain comprising the amino acid sequence of SEQ ID NO:117 and a light chain comprising the amino acid sequence SEQ ID NO:106;

xix. a heavy chain comprising the amino acid sequence of SEQ ID NO:117 and a light chain comprising the amino acid sequence SEQ ID NO:107;

xx. a heavy chain comprising the amino acid sequence of SEQ ID NO:118 and a light chain comprising the amino acid sequence SEQ ID NO:105;

xxi. a heavy chain comprising the amino acid sequence of SEQ ID NO:118 and a light chain comprising the amino acid sequence SEQ ID NO:106;

xxii. a heavy chain comprising the amino acid sequence of SEQ ID NO:118 and a light chain comprising the amino acid sequence SEQ ID NO:107;

xxiii. a heavy chain comprising the amino acid sequence of SEQ ID NO:119 and a light chain comprising the amino acid sequence SEQ ID NO:105;

xxiv. a heavy chain comprising the amino acid sequence of SEQ ID NO:119 and a light chain comprising the amino acid sequence SEQ ID NO:106;

xxv. a heavy chain comprising the amino acid sequence of SEQ ID NO:119 and a light chain comprising the amino acid sequence SEQ ID NO:107; and xxvi. a heavy chain comprising the amino acid sequence of SEQ ID NO:120 and a light chain comprising the amino acid sequence SEQ ID NO:108.

5. The monoclonal antibody or antigen binding fragment thereof of claim 3, wherein the monoclonal antibody or antigen-binding fragment thereof comprises an IgG isotype selected from IgG1, IgG1-N297Q, IgG2, IgG4, IgG4 S228P, IgG4 PE and variants thereof.

6. The monoclonal antibody or antigen binding fragment thereof of claim 1, which selectively binds human SIRPα.

7. The monoclonal antibody or antigen binding fragment thereof of claim 1, which binds human SIRPα and human SIRPγ.

8. The monoclonal antibody or antigen binding fragment thereof of claim 1, which exhibits anti-tumor activity.

9. The monoclonal antibody or antigen binding fragment thereof of claim 1, which increases phagocytosis of human tumor cells.

10. A pharmaceutical composition comprising a monoclonal antibody or antigen binding fragment thereof of claim 1, and a pharmaceutically or physiologically acceptable carrier, diluent, or excipient.

11. A method of treating cancer in a subject in need thereof, the method comprising administering to the subject a monoclonal antibody or antigen binding fragment thereof of claim 1, in an amount effective to treat cancer.

12. The method of claim 11, wherein the monoclonal antibody or antigen binding fragment thereof is administered in combination with a chemotherapeutic agent or therapeutic antibody.

13. The method of claim 12, wherein the therapeutic antibody is directed against a cellular target selected from CD47 (Cluster of Differentiation 47), CD70 (Cluster of Differentiation 70), CD200 (OX-2 membrane glycoprotein, Cluster of Differentiation 200), CD154 (Cluster of Differentiation 154, CD40L, CD40 ligand, Cluster of Differentiation 40 ligand), CD223 (Lymphocyte-activation gene 3, LAG3, Cluster of Differentiation 223), KIR (Killer-cell immunoglobulin-like receptors), GITR (TNFRSF18, glucocorticoid-induced TNFR-related protein, activation-inducible TNFR family receptor, AITR, Tumor necrosis factor receptor superfamily member 18), CD20 (Cluster of Differentiation), CD28 (Cluster of Differentiation 28), CD40 (Cluster of Differentiation 40, Bp50, CDW40, TNFRSF5, Tumor necrosis factor receptor superfamily member 5, p50), CD86 (B7-2, Cluster of Differentiation 86), CD160 (Cluster of Differentiation 160, BY55, NK1, NK28), CD258 (LIGHT, Cluster of Differentiation 258, Tumor necrosis factor ligand superfamily member 14, TNFSF14, herpesvirus entry mediator ligand (HVEM-L), CD270 (HVEM, Tumor necrosis factor receptor superfamily member 14, herpesvirus entry mediator, Cluster of Differentiation 270, LIGHTR, HVEA), CD275 (ICOSL, ICOS ligand, Inducible T-cell co-stimulator ligand, Cluster of Differentiation 275), CD276 (B7-H3, B7 homolog 3, Cluster of Differentiation 276), OX40L (OX40 Ligand), B7-H4 (B7 homolog 4, VTCN1, V-set domain-containing T-cell activation inhibitor 1), GITRL (Glucocorticoid-induced tumor necrosis factor receptor-ligand, glucocorticoid-induced TNFR-ligand), 4-1BBL (4-1BB ligand), CD3 (Cluster of Differentiation 3, T3D), CD25 (IL2Rα, Cluster of Differentiation 25, Interleukin-2 Receptor α chain, IL-2 Receptor α chain), CD48 (Cluster of Differentiation 48, B-lymphocyte activation marker, BLAST-1, signaling lymphocytic activation molecule 2, SLAMF2), CD66a (Ceacam-1, Carcinoembryonic antigen-related cell adhesion molecule 1, biliary glycoprotein, BGP, BGP1, BGPI, Cluster of Differentiation 66a), CD80 (B7-1, Cluster of Differentiation 80), CD94 (Cluster of Differentiation 94), NKG2A (Natural killer group 2A, killer cell lectin-like receptor subfamily D member 1, KLRD1), CD96 (Cluster of Differentiation 96, TActILE, T-cell activation increased late expression), CD112 (PVRL2, nectin, Poliovirus receptor-related 2, herpesvirus entry mediator B, HVEB, nectin-2, Cluster of Differentiation 112), CD115 (CSF1R, Colony stimulating factor 1 receptor, macrophage colony-stimulating factor receptor, M-CSFR, Cluster of Differentiation 115), CD205 (DEC-205, LY75, Lymphocyte antigen 75, Cluster of Differentiation 205), CD226 (DNAM1, Cluster of Differentiation 226, DNAX Accessory Molecule-1, PTA1, platelet and T-cell activation antigen 1), CD244 (Cluster of Differentiation 244, Natural killer cell receptor 2B4), CD262 (DRS, TrailR2, TRAIL-R2, Tumor necrosis factor receptor superfamily member 10b, TNFRSF10B, Cluster of Differentiation 262, KILLER, TRICK2, TRICKB, ZTNFR9, TRICK2A, TRICK2B), CD284 (Toll-like Receptor-4, TLR4, Cluster of Differentiation 284), CD288 (Toll-like Receptor-8, TLR8, Cluster of Differentiation 288), Leukemia Inhibitor Factor (LIF), TNFSF15 (Tumor necrosis factor superfamily member 15, Vascular endothelial growth inhibitor, VEGI, TL1A), TDO2 (Tryptophan 2,3-dioxygenase, TPH2, TRPO), IGF-1R (Type 1 Insulin-like Growth Factor), GD2 (Disialoganglioside 2), TMIGD2 (Transmembrane and immunoglobulin domain-containing protein 2), RGMB (RGM domain family, member B), VISTA (V-domain immunoglobulin-containing suppressor of T-cell activation, B7-H5, B7 homolog 5), BTNL2 (Butyrophilin-like protein 2), Btn (Butyrophilin family), TIGIT (T-cell Immunoreceptor with Ig and ITIM domains, Vstm3, WUCAM), Siglecs (Sialic acid binding Ig-like lectins), Neurophilin, VEGFR (Vascular endothelial growth factor receptor), ILT family (LIRs, immunoglobulin-like transcript family, leukocyte immunoglobulin-like receptors), NKG families (Natural killer group families, C-type lectin transmembrane receptors), MICA (MHC class I polypeptide-related sequence A), TGFβ (Transforming growth factor β), STING pathway (Stimulator of interferon gene pathway), Arginase (Arginine amidinase, canavanase, L-arginase, arginine transamidinase), EGFRvIII (Epidermal growth factor receptor variant III), HHLA2 (B7-H7, B7y, HERV-H LTR-associating protein 2, B7 homolog 7), inhibitors of PD-1 (Programmed cell death protein 1, PD-1, CD279, Cluster of Differentiation 279), PD-L1 (B7-H1, B7 homolog 1, Programmed death-ligand 1, CD274, cluster of Differentiation 274), PD-L2 (B7-DC, Programmed cell death 1 ligand 2, PDCD1LG2, CD273, Cluster of Differentiation 273), CTLA-4 (Cytotoxic T-lymphocyte-associated protein 4, CD152, Cluster of Differentiation 152), BTLA (B- and T-lymphocyte attenuator, CD272, Cluster of Differentiation 272), Indoleamine 2,3-dioxygenase (IDO, IDO1), TIM3 (HAVCR2, Hepatitis A virus cellular receptor 2, T-cell immunoglobulin mucin-3, KIM-3, Kidney injury molecule 3, TIMD-3, T-cell immunoglobulin mucin-domain 3), A2A adenosine receptor (ADO receptor), CD39 (ectonucleoside triphosphate diphosphohydrolase-1, Cluster of Differentiation 39, ENTPD1), CD73 (Ecto-5'-nucleotidase, 5'-nucleotidase, 5'-NT, Cluster of Differentiation 73), CD27 (Cluster of Differentiation 27), ICOS (CD278, Cluster of Differentiation 278, Inducible T-cell Co-stimulator), CD137 (4-1BB, Cluster of Differentiation 137, tumor necrosis factor receptor superfamily member 9, TNFRSF9), OX40 (CD134, Cluster of Differentiation 134), TNFSF25 (Tumor necrosis factor receptor superfamily member 25), IL-10 (Interleukin-10, human cytokine synthesis inhibitory factor, CSIF), and Galectins.

14. The method of claim 11, wherein the monoclonal antibody or antigen binding fragment thereof is administered in combination with an opsonizing antibody which targets an antigen on a tumor cell.

15. The method of claim 14, wherein the opsonizing antibody is selected from rituximab (anti-CD20), trastuzumab (anti-HER2), alemtuzumab (anti-CD52), cetuximab (anti-EGFR), panitumumab (anti-EGFR), ofatumumab (anti-CD20), denosumab (anti-RANKL), pertuzumab (anti-HER2), panitumumab (anti-EGFR), pertuzumab (anti-HER2), elotuzumab (anti-SLAMF7), atezolizumab (anti-PD-L1), avelumab (anti-PD-L1), durvalumab (anti-PD-L1), necitumumab (anti-EGFR), daratumumab (anti-CD38), obinutuzumab (anti-CD20), blinatumomab (anti-CD19/CD3), and dinutuximab (anti-GD2).

16. The method of claim 14, wherein the target antigen on a tumor cell is selected from CD20, EGFR, PD-1, and PD-L1.

17. The method of claim 11, wherein said cancer is selected from leukemia, a lymphoma, multiple myeloma, ovarian cancer, breast cancer, endometrial cancer, colon cancer, rectal cancer, bladder cancer, urothelial cancer, lung cancer, bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck, testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and a sarcoma;
wherein the lung cancer is selected from non-small cell lung cancer, adenocarcinoma of the lung, and squamous cell carcinoma of the lung.

18. The method of claim 17, wherein said leukemia is selected from systemic mastocytosis, acute lymphocytic (lymphoblastic) leukemia (ALL), T-cell ALL, acute myeloid leukemia (AML), chronic lymphocytic leukemia (CLL), chronic myeloid leukemia (CML), myeloproliferative disorder/neoplasm, myelodysplastic syndrome, monocytic cell leukemia, and plasma cell leukemia.

19. The method of claim 17, wherein said lymphoma is selected from histiocytic lymphoma, T-cell lymphoma, and B cell lymphoma.

20. The method of claim 17, wherein said sarcoma is selected from osteosarcoma, Ewing's sarcoma, leiomyosarcoma, synovial sarcoma, alveolar soft part sarcoma, angiosarcoma, liposarcoma, fibrosarcoma, rhabdomyosarcoma, and chrondrosarcoma.

21. The method of claim 17, wherein said lymphoma is selected from low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia.

* * * * *

SEQUENCE LISTING

<160> NUMBER OF SEQ ID NOS: 131

<210> SEQ ID NO 1
<211> LENGTH: 10
<212> TYPE: PRT
<213> ORGANISM: Artificial Sequence
<220> FEATURE:
<223> OTHER INFORMATION: LCDR1

<400> SEQUENCE: 1

Arg Ala Ser Ser Gly Val Asn Tyr Met Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: LCDR2

<400> SEQUENCE: 2

Tyr Thr Ser Ile Leu Ala Pro
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3

<400> SEQUENCE: 3

Gln Gln Phe Thr Ser Ser Pro Tyr Thr
1               5

<210> SEQ ID NO 4
<211> LENGTH: 11
<212> TYPE: PRT
<213> ORGANISM: Artificial Sequence
<220> FEATURE:
<223> OTHER INFORMATION: LCDR1

<400> SEQUENCE: 4

Arg Ala Ser Gln Ser Ile Gly Thr Ser Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Tyr Gly Ser Glu Ser Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln Gln Ser Asn Thr Trp Pro Leu Thr
1               5

```
<210> SEQ ID NO 7
<211> LENGTH: 12
<212> TYPE: PRT
<213> ORGANISM: Artificial Sequence
<220> FEATURE:
<223> OTHER INFORMATION: LCDR1

<400> SEQUENCE: 7

Ser Ala Ser Ser Ile Ile Gly Ser Asp Phe Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: LCDR2

<400> SEQUENCE: 8

Arg Thr Ser Ile Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: LCDR3

<400> SEQUENCE: 9

Gln Gln Gly Ser Gly Leu Pro Leu Thr
1               5

<210> SEQ ID NO 10
<211> LENGTH: 11
<212> TYPE: PRT
<213> ORGANISM: Artificial Sequence
<220> FEATURE:
<223> OTHER INFORMATION: LCDR1

<400> SEQUENCE: 10

Lys Ala Ser Gln Asp Ile Asn Ser His Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2

<400> SEQUENCE: 11

Arg Ala Asn Arg Leu Ala Asp
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3

<400> SEQUENCE: 12

Leu Gln Tyr Asp Glu Phe Pro Tyr Thr
1               5
```

```
<210> SEQ ID NO 13
<211> LENGTH: 10
<212> TYPE: PRT
<213> ORGANISM: Artificial Sequence
<220> FEATURE:
<223> OTHER INFORMATION: LCDR1

<400> SEQUENCE: 13

Ser Ala Ser Ser Ser Val Ser Tyr Met Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: LCDR2

<400> SEQUENCE: 14

Leu Thr Ser Asn Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: LCDR3

<400> SEQUENCE: 15

Gln Gln Trp Ser Gly Asn Pro Phe Thr
1               5

<210> SEQ ID NO 16
<211> LENGTH: 11
<212> TYPE: PRT
<213> ORGANISM: Artificial Sequence
<220> FEATURE:
<223> OTHER INFORMATION: LCDR1

<400> SEQUENCE: 16

Arg Ala Ser Glu Asn Ile Tyr Ser Tyr Leu Thr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: LCDR2

<400> SEQUENCE: 17

Asn Ala Lys Thr Leu Ala Glu
1               5

<210> SEQ ID NO 18
<211> LENGTH: 9
<212> TYPE: PRT
<213> ORGANISM: Artificial Sequence
<220> FEATURE:
<223> OTHER INFORMATION: LCDR3

<400> SEQUENCE: 18

Gln His His Tyr Gly Ser Pro Arg Thr
1               5
```

```
<210> SEQ ID NO 19
<211> LENGTH: 12
<212> TYPE: PRT
<213> ORGANISM: Artificial Sequence
<220> FEATURE:
<223> OTHER INFORMATION: LCDR1

<400> SEQUENCE: 19

Ser Ala Ser Ser Ser Ile Ser Ser Asn Phe Leu His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: LCDR2

<400> SEQUENCE: 20

Arg Thr Ser Ile Leu Ala Ser
1               5

<210> SEQ ID NO 21
<211> LENGTH: 9
<212> TYPE: PRT
<213> ORGANISM: Artificial Sequence
<220> FEATURE:
<223> OTHER INFORMATION: LCDR3

<400> SEQUENCE: 21

Gln Gln Gly Ser Gly Leu Pro Leu Thr
1               5

<210> SEQ ID NO 22
<211> LENGTH: 5
<212> TYPE: PRT
<213> ORGANISM: Artificial Sequence
<220> FEATURE:
<223> OTHER INFORMATION: LCDR1

<400> SEQUENCE: 22

Ser Ser Val Ser Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: LCDR2

<400> SEQUENCE: 23

Asp Thr Ser
1

<210> SEQ ID NO 24
<211> LENGTH: 9
<212> TYPE: PRT
<213> ORGANISM: Artificial Sequence
<220> FEATURE:
<223> OTHER INFORMATION: LCDR3

<400> SEQUENCE: 24

Gln Gln Trp Ser Ser Phe Pro Trp Thr
1               5

<210> SEQ ID NO 25
```

```
<211> LENGTH: 6
<212> TYPE: PRT
<213> ORGANISM: Artificial Sequence
<220> FEATURE:
<223> OTHER INFORMATION: LCDR1

<400> SEQUENCE: 25

Glu Asp Ile Tyr Asp Arg
1               5

<210> SEQ ID NO 26
<211> LENGTH: 3
<212> TYPE: PRT
<213> ORGANISM: Artificial Sequence
<220> FEATURE:
<223> OTHER INFORMATION: LCDR2

<400> SEQUENCE: 26

Gly Thr Ala
1

<210> SEQ ID NO 27
<211> LENGTH: 9
<212> TYPE: PRT
<213> ORGANISM: Artificial Sequence
<220> FEATURE:
<223> OTHER INFORMATION: LCDR3

<400> SEQUENCE: 27

Gln Gln Tyr Trp Thr Thr Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: LCDR1

<400> SEQUENCE: 28

Ser Ser Val Asn Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: LCDR2

<400> SEQUENCE: 29

Tyr Thr Ser
1

<210> SEQ ID NO 30
<211> LENGTH: 9
<212> TYPE: PRT
<213> ORGANISM: Artificial Sequence
<220> FEATURE:
<223> OTHER INFORMATION: LCDR3

<400> SEQUENCE: 30

Gln Gln Phe Thr Ser Ser Pro Phe Thr
1               5

<210> SEQ ID NO 31
<211> LENGTH: 7
```

```
<212> TYPE: PRT
<213> ORGANISM: Artificial Sequence
<220> FEATURE:
<223> OTHER INFORMATION: LCDR2

<400> SEQUENCE: 31

Arg Ala Asn Arg Leu Ala Thr
1               5

<210> SEQ ID NO 32
<211> LENGTH: 9
<212> TYPE: PRT
<213> ORGANISM: Artificial Sequence
<220> FEATURE:
<223> OTHER INFORMATION: LCDR3

<400> SEQUENCE: 32

Gln Gln Tyr Asp Glu Phe Pro Tyr Thr
1               5

<210> SEQ ID NO 33
<211> LENGTH: 5
<212> TYPE: PRT
<213> ORGANISM: Artificial Sequence
<220> FEATURE:
<223> OTHER INFORMATION: HCDR1

<400> SEQUENCE: 33

Lys Tyr Trp Ile Glu
1               5

<210> SEQ ID NO 34
<211> LENGTH: 17
<212> TYPE: PRT
<213> ORGANISM: Artificial Sequence
<220> FEATURE:
<223> OTHER INFORMATION: HCDR2

<400> SEQUENCE: 34

Glu Ile Leu Pro Gly Ser Val Ile Thr Asn Tyr Asn Glu Lys Phe Lys
1               5                   10                  15

Gly

<210> SEQ ID NO 35
<211> LENGTH: 12
<212> TYPE: PRT
<213> ORGANISM: Artificial Sequence
<220> FEATURE:
<223> OTHER INFORMATION: HCDR3

<400> SEQUENCE: 35

Trp Gly Leu Tyr Asp Ser Asp Asp Gly Val Asp Tyr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: HCDR1

<400> SEQUENCE: 36

Gly Cys Thr Met Ser
1               5

<210> SEQ ID NO 37
```

```
<211> LENGTH: 17
<212> TYPE: PRT
<213> ORGANISM: Artificial Sequence
<220> FEATURE:
<223> OTHER INFORMATION: HCDR2

<400> SEQUENCE: 37

Tyr Ile Ser Asn Gly Gly Asp Ile Thr Tyr Tyr Pro Asp Thr Val Lys
1               5                   10                  15
Gly

<210> SEQ ID NO 38
<211> LENGTH: 10
<212> TYPE: PRT
<213> ORGANISM: Artificial Sequence
<220> FEATURE:
<223> OTHER INFORMATION: HCDR3

<400> SEQUENCE: 38

Leu Asp Gly Tyr Tyr Tyr Ala Met Asp Phe
1               5                   10

<210> SEQ ID NO 39
<211> LENGTH: 5
<212> TYPE: PRT
<213> ORGANISM: Artificial Sequence
<220> FEATURE:
<223> OTHER INFORMATION: HCDR1

<400> SEQUENCE: 39

Ser Tyr Val Met His
1               5

<210> SEQ ID NO 40
<211> LENGTH: 17
<212> TYPE: PRT
<213> ORGANISM: Artificial Sequence
<220> FEATURE:
<223> OTHER INFORMATION: HCDR2

<400> SEQUENCE: 40

Tyr Ile Asn Pro Tyr Asn Asp Gly Pro Lys Tyr Asn Glu Lys Phe Lys
1               5                   10                  15
Gly

<210> SEQ ID NO 41
<211> LENGTH: 12
<212> TYPE: PRT
<213> ORGANISM: Artificial Sequence
<220> FEATURE:
<223> OTHER INFORMATION: HCDR3

<400> SEQUENCE: 41

Trp Asp Tyr Phe Asn Ser Ala Ser Gly Phe Ala Phe
1               5                   10

<210> SEQ ID NO 42
<211> LENGTH: 5
<212> TYPE: PRT
<213> ORGANISM: Artificial Sequence
<220> FEATURE:
<223> OTHER INFORMATION: HCDR1

<400> SEQUENCE: 42

Asp Tyr Phe Leu Asn
1               5
```

```
<210> SEQ ID NO 43
<211> LENGTH: 17
<212> TYPE: PRT
<213> ORGANISM: Artificial Sequence
<220> FEATURE:
<223> OTHER INFORMATION: HCDR2

<400> SEQUENCE: 43

Arg Ile Asn Pro Tyr Asn Gly Asp Ser Phe Ile Asn Gln Asn Phe Arg
1               5                   10                  15

Asp

<210> SEQ ID NO 44
<211> LENGTH: 13
<212> TYPE: PRT
<213> ORGANISM: Artificial Sequence
<220> FEATURE:
<223> OTHER INFORMATION: HCDR3

<400> SEQUENCE: 44

Gly Gly Tyr Asp Gly Tyr Phe Ile Ala Tyr Phe Asp Tyr
1               5                   10

<210> SEQ ID NO 45
<211> LENGTH: 5
<212> TYPE: PRT
<213> ORGANISM: Artificial Sequence
<220> FEATURE:
<223> OTHER INFORMATION: HCDR1

<400> SEQUENCE: 45

Ser Tyr Thr Met His
1               5

<210> SEQ ID NO 46
<211> LENGTH: 17
<212> TYPE: PRT
<213> ORGANISM: Artificial Sequence
<220> FEATURE:
<223> OTHER INFORMATION: HCDR2

<400> SEQUENCE: 46

Tyr Ile Asn Pro Thr Ile Gly Tyr Thr Glu Tyr Asn Gln Lys Phe Lys
1               5                   10                  15

Asp

<210> SEQ ID NO 47
<211> LENGTH: 13
<212> TYPE: PRT
<213> ORGANISM: Artificial Sequence
<220> FEATURE:
<223> OTHER INFORMATION: HCDR3

<400> SEQUENCE: 47

Leu Val Ile Thr Ser Val Leu Gly Arg Ala Met Asp Tyr
1               5                   10

<210> SEQ ID NO 48
<211> LENGTH: 5
<212> TYPE: PRT
<213> ORGANISM: Artificial Sequence
<220> FEATURE:
<223> OTHER INFORMATION: HCDR1

<400> SEQUENCE: 48
```

-continued

Asp Tyr Gly Val Asn
1               5

<210> SEQ ID NO 49
<211> LENGTH: 17
<212> TYPE: PRT
<213> ORGANISM: Artificial Sequence
<220> FEATURE:
<223> OTHER INFORMATION: HCDR2

<400> SEQUENCE: 49

Trp Val Asn Thr Asn Thr Arg Glu Ser Thr Tyr Val Glu Asp Phe Lys
1               5                  10                  15

Gly

<210> SEQ ID NO 50
<211> LENGTH: 14
<212> TYPE: PRT
<213> ORGANISM: Artificial Sequence
<220> FEATURE:
<223> OTHER INFORMATION: HCDR3

<400> SEQUENCE: 50

Gly Ala Tyr Asp Ala Tyr Tyr Tyr Tyr Gly Met Asp Tyr
1               5                  10

<210> SEQ ID NO 51
<211> LENGTH: 5
<212> TYPE: PRT
<213> ORGANISM: Artificial Sequence
<220> FEATURE:
<223> OTHER INFORMATION: HCDR1

<400> SEQUENCE: 51

Thr Tyr Val Met His
1               5

<210> SEQ ID NO 52
<211> LENGTH: 17
<212> TYPE: PRT
<213> ORGANISM: Artificial Sequence
<220> FEATURE:
<223> OTHER INFORMATION: HCDR2

<400> SEQUENCE: 52

Tyr Ile Asn Pro Asn Asn Asp Gly Pro Asn Tyr Asn Glu Lys Phe Lys
1               5                  10                  15

Gly

<210> SEQ ID NO 53
<211> LENGTH: 12
<212> TYPE: PRT
<213> ORGANISM: Artificial Sequence
<220> FEATURE:
<223> OTHER INFORMATION: HCDR3

<400> SEQUENCE: 53

Trp Asp Ser Tyr Asn Ser Ala Ala Gly Phe Ala Tyr
1               5                  10

<210> SEQ ID NO 54
<211> LENGTH: 8
<212> TYPE: PRT
<213> ORGANISM: Artificial Sequence
<220> FEATURE:

<223> OTHER INFORMATION: HCDR1

<400> SEQUENCE: 54

Gly Phe Thr Leu Ser Thr Tyr Thr
1               5

<210> SEQ ID NO 55
<211> LENGTH: 8
<212> TYPE: PRT
<213> ORGANISM: Artificial Sequence
<220> FEATURE:
<223> OTHER INFORMATION: HCDR2

<400> SEQUENCE: 55

Ile Thr Ser Gly Asp Thr Tyr Thr
1               5

<210> SEQ ID NO 56
<211> LENGTH: 8
<212> TYPE: PRT
<213> ORGANISM: Artificial Sequence
<220> FEATURE:
<223> OTHER INFORMATION: HCDR3

<400> SEQUENCE: 56

Thr Arg Asp Arg Pro Leu Phe His
1               5

<210> SEQ ID NO 57
<211> LENGTH: 8
<212> TYPE: PRT
<213> ORGANISM: Artificial Sequence
<220> FEATURE:
<223> OTHER INFORMATION: HCDR1

<400> SEQUENCE: 57

Gly Tyr Thr Phe Thr Asp Tyr Glu
1               5

<210> SEQ ID NO 58
<211> LENGTH: 8
<212> TYPE: PRT
<213> ORGANISM: Artificial Sequence
<220> FEATURE:
<223> OTHER INFORMATION: HCDR2

<400> SEQUENCE: 58

Ile His Pro Gly Ser Gly Gly Thr
1               5

<210> SEQ ID NO 59
<211> LENGTH: 12
<212> TYPE: PRT
<213> ORGANISM: Artificial Sequence
<220> FEATURE:
<223> OTHER INFORMATION: HCDR3

<400> SEQUENCE: 59

Thr Arg Ala Val Ser Gly Tyr Tyr Ala Met Asp Tyr
1               5                   10

<210> SEQ ID NO 60
<211> LENGTH: 8
<212> TYPE: PRT
<213> ORGANISM: Artificial Sequence
<220> FEATURE:
<223> OTHER INFORMATION: HCDR1

```
<400> SEQUENCE: 60

Gly Tyr Thr Phe Ser Asn Tyr Leu
1               5

<210> SEQ ID NO 61
<211> LENGTH: 8
<212> TYPE: PRT
<213> ORGANISM: Artificial Sequence
<220> FEATURE:
<223> OTHER INFORMATION: HCDR2

<400> SEQUENCE: 61

Ile Tyr Pro Gly Asp Asn Asn Thr
1               5

<210> SEQ ID NO 62
<211> LENGTH: 11
<212> TYPE: PRT
<213> ORGANISM: Artificial Sequence
<220> FEATURE:
<223> OTHER INFORMATION: HCDR3

<400> SEQUENCE: 62

Ala Gly Gly Thr Asp Tyr Asp Gly Phe Ala Asn
1               5                   10

<210> SEQ ID NO 63
<211> LENGTH: 12
<212> TYPE: PRT
<213> ORGANISM: Artificial Sequence
<220> FEATURE:
<223> OTHER INFORMATION: HCDR3

<400> SEQUENCE: 63

Ala Arg Ala Val Ser Gly Tyr Tyr Ala Met Asp Tyr
1               5                   10

<210> SEQ ID NO 64
<211> LENGTH: 106
<212> TYPE: PRT
<213> ORGANISM: Artificial Sequence
<220> FEATURE:
<223> OTHER INFORMATION: Light Chain (VL) Variable Domain Sequence

<400> SEQUENCE: 64

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Gly Val Asn Tyr Met
            20                  25                  30

Tyr Trp Tyr Gln Gln Lys Ser Asp Ala Ser Pro Lys Leu Leu Ile Tyr
        35                  40                  45

Tyr Thr Ser Ile Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 65
<211> LENGTH: 107
```

<212> TYPE: PRT
<213> ORGANISM: Artificial Sequence
<220> FEATURE:
<223> OTHER INFORMATION: Light Chain (VL) Variable Domain Sequence

<400> SEQUENCE: 65

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Gly Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Thr Trp Pro Leu
                85                  90                  95

Thr Phe Gly Asp Gly Thr Lys Leu Glu Leu Lys
            100                 105
```

<210> SEQ ID NO 66
<211> LENGTH: 108
<212> TYPE: PRT
<213> ORGANISM: Artificial Sequence
<220> FEATURE:
<223> OTHER INFORMATION: Light Chain (VL) Variable Domain Sequence

<400> SEQUENCE: 66

```
Glu Ile Val Leu Thr Gln Ser Pro Thr Thr Met Ala Ala Ser Pro Gly
1               5                   10                  15

Glu Lys Ile Thr Ile Ile Cys Ser Ala Ser Ser Ile Ile Gly Ser Asp
            20                  25                  30

Phe Leu His Trp Tyr Gln Gln Arg Pro Gly Phe Ser Pro Lys Phe Leu
        35                  40                  45

Ile Tyr Arg Thr Ser Ile Leu Ala Ser Gly Val Pro Thr Arg Phe Thr
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Gly Leu Pro
                85                  90                  95

Leu Thr Phe Gly Ser Gly Thr Lys Leu Glu Met Lys
            100                 105
```

<210> SEQ ID NO 67
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 67

```
Asp Ile Lys Leu Thr Gln Ser Gln Ser Ser Met Tyr Ser Ser Leu Gly
1               5                   10                  15

Gln Arg Val Thr Ile Thr Cys Lys Ala Ser Gln Asp Ile Asn Ser His
            20                  25                  30

Leu Ser Trp Phe Gln Glu Lys Pro Gly Lys Ser Pro Lys Thr Leu Ile
        35                  40                  45

Tyr Arg Ala Asn Arg Leu Ala Asp Gly Val Pro Ser Arg Phe Ser Gly
```

```
                    50                  55                  60
Ser Gly Ser Gly Gln Asp Tyr Phe Leu Thr Ile Ser Ser Leu Glu Tyr
 65                  70                  75                  80

Glu Asp Val Gly Ile Tyr Tyr Cys Leu Gln Tyr Asp Glu Phe Pro Tyr
                 85                  90                  95

Thr Phe Gly Gly Gly Thr Lys Leu Glu Ile Lys
            100                 105

<210> SEQ ID NO 68
<211> LENGTH: 106
<212> TYPE: PRT
<213> ORGANISM: Artificial Sequence
<220> FEATURE:
<223> OTHER INFORMATION: Light Chain (VL) Variable Domain Sequence

<400> SEQUENCE: 68

Gln Ile Val Leu Thr Gln Ser Pro Ala Leu Met Ser Ala Ser Pro Gly
 1               5                  10                  15

Glu Lys Val Thr Met Thr Cys Ser Ala Ser Ser Val Ser Tyr Met
                20                  25                  30

Tyr Trp Phe Gln Gln Lys Pro Arg Ser Ser Pro Lys Pro Trp Ile Tyr
             35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Phe Thr
                 85                  90                  95

Phe Gly Ser Gly Thr Lys Leu Glu Ile Lys
            100                 105

<210> SEQ ID NO 69
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 69

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Thr Trp Tyr Lys Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His Tyr Gly Ser Pro Arg
                 85                  90                  95

Thr Phe Gly Gly Gly Thr Lys Leu Glu Ile Lys
            100                 105

<210> SEQ ID NO 70
<211> LENGTH: 108
<212> TYPE: PRT
<213> ORGANISM: Artificial Sequence
<220> FEATURE:
```

<223> OTHER INFORMATION: Light Chain (VL) Variable Domain Sequence

<400> SEQUENCE: 70

```
Glu Ile Val Leu Thr Gln Ser Pro Thr Thr Met Ala Ala Ser Pro Gly
1               5                   10                  15
Glu Lys Ile Thr Ile Ile Cys Ser Ala Ser Ser Ser Ile Ser Ser Asn
            20                  25                  30
Phe Leu His Trp Tyr Gln Gln Lys Pro Gly Phe Ser Pro Arg Phe Leu
        35                  40                  45
Ile Tyr Arg Thr Ser Ile Leu Ala Ser Gly Val Pro Thr Arg Phe Ser
    50                  55                  60
Gly Ser Gly Ser Gly Thr Ser Tyr Ser Leu Thr Ile Asp Thr Met Glu
65                  70                  75                  80
Ala Glu Asp Val Ala Thr Tyr Tyr Cys Gln Gln Gly Ser Gly Leu Pro
                85                  90                  95
Leu Thr Phe Gly Ser Gly Thr Lys Leu Glu Ile Lys
            100                 105
```

<210> SEQ ID NO 71
<211> LENGTH: 106
<212> TYPE: PRT
<213> ORGANISM: Artificial Sequence
<220> FEATURE:
<223> OTHER INFORMATION: Light Chain (VL) Variable Domain Sequence

<400> SEQUENCE: 71

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
            20                  25                  30
Tyr Trp Tyr Gln Gln Lys Pro Gly Ser Ser Pro Arg Leu Leu Ile Tyr
        35                  40                  45
Asp Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Trp Ser Ser Phe Pro Trp Thr
                85                  90                  95
Phe Gly Gly Gly Thr Lys Leu Glu Ile Lys
            100                 105
```

<210> SEQ ID NO 72
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 72

```
Asp Ile Gln Met Thr Gln Ser Ser Ser Ser Phe Ser Gly Ser Leu Gly
1               5                   10                  15
Asp Arg Leu Thr Ile Asn Cys Lys Ala Ser Glu Asp Ile Tyr Asp Arg
            20                  25                  30
Val Ala Trp Tyr Gln Gln Lys Pro Gly Asn Ala Pro Arg Leu Leu Ile
        35                  40                  45
Ser Gly Thr Ala Ser Leu Glu Thr Gly Val Leu Ser Arg Phe Ser Gly
    50                  55                  60
Ser Gly Ser Gly Lys Asp Tyr Thr Leu Ser Ile Asn Gly Leu Gln Ala
```

Glu Asp Val Ala Thr Tyr Tyr Cys Gln Gln Tyr Trp Thr Thr Pro Trp
65                  70                  75                  80

Thr Phe Gly Gly Gly Thr Lys Leu Glu Ile Lys
            85                  90                  95

100                 105

<210> SEQ ID NO 73
<211> LENGTH: 106
<212> TYPE: PRT
<213> ORGANISM: Artificial Sequence
<220> FEATURE:
<223> OTHER INFORMATION: Light Chain (VL) Variable Domain Sequence

<400> SEQUENCE: 73

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
                20                  25                  30

Tyr Trp Tyr Gln Gln Lys Ser Asp Ala Ser Pro Lys Leu Trp Ile Tyr
            35                  40                  45

Tyr Thr Ser Lys Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Phe Thr
                85                  90                  95

Phe Gly Ser Gly Thr Lys Leu Glu Ile Lys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Light Chain (VL) Variable Domain Sequences

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser His
                20                  25                  30

Leu Ser Trp Tyr Gln Gln Lys Pro Gly Lys Ala Pro Lys Leu Leu Ile
            35                  40                  45

Tyr Arg Ala Asn Arg Leu Ala Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser His
            20                  25                  30

Leu Ser Trp Tyr Gln Gln Lys Pro Gly Lys Ala Pro Lys Leu Leu Ile
        35                  40                  45

Tyr Arg Ala Asn Arg Leu Ala Thr Gly Val Pro Ser Arg Phe Ser Gly
50                  55                  60

Ser Gly Ser Gly Thr Asp Phe Thr Phe Thr Ile Ser Ser Leu Glu Tyr
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 76
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser His
            20                  25                  30

Leu Ser Trp Tyr Gln Gln Lys Pro Gly Lys Ala Pro Lys Leu Leu Ile
        35                  40                  45

Tyr Arg Ala Asn Arg Leu Ala Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Glu Phe Pro Tyr
                85                  90                  95

Thr Phe Gly Gly Gly Thr Lys Leu Glu Ile Lys
            100                 105
```

<210> SEQ ID NO 77
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 77

```
Asp Ile Lys Met Thr Gln Ser Pro Ser Ser Met Tyr Ala Ser Leu Gly
1               5                   10                  15

Gln Arg Val Thr Ile Thr Cys Lys Ala Ser Gln Asp Ile Asn Ser His
            20                  25                  30

Leu Ser Trp Phe Gln Glu Lys Pro Gly Lys Ser Pro Lys Thr Leu Ile
        35                  40                  45

Tyr Arg Ala Asn Arg Leu Ala Asp Gly Val Pro Ser Arg Phe Ser Gly
50                  55                  60

Ser Gly Ser Gly Gln Asp Tyr Phe Leu Thr Ile Ser Ser Leu Glu Tyr
65                  70                  75                  80

Glu Asp Val Gly Ile Tyr Tyr Cys Leu Gln Tyr Asp Glu Phe Pro Tyr
```

```
                    85                  90                  95

Thr Phe Gly Gly Gly Thr Lys Leu Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asp Arg
            20                  25                  30

Val Ala Trp Tyr Gln Gln Lys Pro Gly Lys Ala Pro Lys Leu Leu Ile
        35                  40                  45

Tyr Gly Thr Ala Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Trp Thr Thr Pro Trp
                85                  90                  95

Thr Phe Gly Gly Gly Thr Lys Val Glu Ile Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asp Arg
            20                  25                  30

Val Ala Trp Tyr Gln Gln Lys Pro Gly Lys Ala Pro Lys Leu Leu Ile
        35                  40                  45

Tyr Gly Thr Ala Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Trp
                85                  90                  95

Thr Phe Gly Gly Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Light Chain (VL) Variable Domain Sequence

<400> SEQUENCE: 80

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Glu Asp Ile Tyr Asp Arg
            20                  25                  30

Val Ala Trp Tyr Gln Gln Lys Pro Gly Lys Ala Pro Lys Leu Leu Ile
        35                  40                  45

Tyr Gly Thr Ala Ser Leu Glu Thr Gly Val Leu Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Tyr Trp Thr Thr Pro Trp
                85                  90                  95

Thr Phe Gly Gly Gly Thr Lys Val Glu Ile Lys
            100                 105

<210> SEQ ID NO 81
<211> LENGTH: 121
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 81

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ser Phe Thr Lys Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Val Ile Thr Asn Tyr Asn Glu Lys Phe
    50                  55                  60

Lys Gly Lys Ala Thr Phe Thr Ala Asp Thr Ser Ser Asn Thr Val Tyr
65                  70                  75                  80

Met Gln Leu Ser Ser Leu Thr Ser Glu Asp Ser Ala Val Tyr Tyr Cys
                85                  90                  95

Thr Lys Trp Gly Leu Tyr Asp Ser Asp Asp Gly Val Asp Tyr Trp Gly
            100                 105                 110

Gln Gly Thr Thr Leu Thr Val Ser Ser
        115                 120

<210> SEQ ID NO 82
<211> LENGTH: 119
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 82

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Ser Phe Ser Gly Cys
            20                  25                  30

Thr Met Ser Trp Ile Arg Gln Thr Pro Glu Arg Arg Leu Glu Trp Val
        35                  40                  45

Ala Tyr Ile Ser Asn Gly Gly Asp Ile Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Lys Ser Glu Asp Thr Ala Met Tyr Tyr Cys 85                  90                  95

Ala Arg Leu Asp Gly Tyr Tyr Tyr Ala Met Asp Phe Trp Gly Gln Gly
            100                 105                 110

Thr Ser Val Thr Val Ser Ser
        115

<210> SEQ ID NO 83
<211> LENGTH: 121
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 83

Glu Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Pro Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Phe Cys
                85                  90                  95

Ala Arg Trp Asp Tyr Phe Asn Ser Ala Ser Gly Phe Ala Phe Trp Gly
            100                 105                 110

Gln Gly Thr Leu Val Thr Val Ser Ala
        115                 120

<210> SEQ ID NO 84
<211> LENGTH: 122
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 84

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Asp Tyr
            20                  25                  30

Phe Leu Asn Trp Val Lys Gln Ser His Gly Lys Ser Leu Glu Trp Ile
        35                  40                  45

Gly Arg Ile Asn Pro Tyr Asn Gly Asp Ser Phe Ile Asn Gln Asn Phe
    50                  55                  60

Arg Asp Lys Ala Thr Leu Thr Val Asp Lys Ser Ser Thr Thr Ala His
65                  70                  75                  80

Met Asp Leu Leu Ser Leu Thr Ser Glu Asp Ser Ala Ile Tyr Tyr Cys
                85                  90                  95

Gly Arg Gly Gly Tyr Asp Gly Tyr Phe Ile Ala Tyr Phe Asp Tyr Trp
            100                 105                 110

Gly Gln Gly Ser Leu Val Thr Val Ser Ala
        115                 120

<210> SEQ ID NO 85
<211> LENGTH: 122

```
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 85

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Thr Ile Gly Tyr Thr Glu Tyr Asn Gln Lys Phe
    50                  55                  60

Lys Asp Lys Thr Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Leu Val Ile Thr Ser Val Leu Gly Arg Ala Met Asp Tyr Trp
            100                 105                 110

Gly Gln Gly Thr Ser Val Thr Val Ser Ser
        115                 120

<210> SEQ ID NO 86
<211> LENGTH: 123
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 86

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Gly Val Asn Trp Val Lys Gln Gly Pro Gly Lys Asp Leu Gln Trp Met
        35                  40                  45

Gly Trp Val Asn Thr Asn Thr Arg Glu Ser Thr Tyr Val Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Ser Ser Thr Tyr Phe Cys
                85                  90                  95

Ala Arg Gly Ala Tyr Asp Ala Tyr Tyr Tyr Tyr Gly Met Asp Tyr
            100                 105                 110

Trp Gly Gln Gly Thr Ser Val Thr Val Ser Ser
        115                 120

<210> SEQ ID NO 87
<211> LENGTH: 121
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 87

Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Thr Phe Ser Thr Tyr
```

```
            20                  25                  30
Val Met His Trp Ile Lys His Arg Pro Gly Gln Gly Leu Glu Trp Ile
        35                  40                  45

Gly Tyr Ile Asn Pro Asn Asn Asp Gly Pro Asn Tyr Asn Glu Lys Phe
    50                  55                  60

Lys Gly Lys Ala Thr Leu Thr Ser Asp Ile Ser Ser Thr Ala Tyr
65                  70                  75                  80

Met Glu Leu Ser Ser Leu Thr Ser Glu Asp Ser Ala Val Tyr Phe Cys
                85                  90                  95

Ser Arg Trp Asp Ser Tyr Asn Ser Ala Ala Gly Phe Ala Tyr Trp Gly
                100                 105                 110

His Gly Thr Leu Val Thr Val Ser Ala
        115                 120
```

<210> SEQ ID NO 88
<211> LENGTH: 115
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 88

```
Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Leu Ser Thr Tyr
                20                  25                  30

Thr Met Ser Trp Val Arg Gln Thr Pro Glu Lys Arg Leu Glu Trp Val
        35                  40                  45

Ala Ile Ile Thr Ser Gly Asp Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Gly Met Tyr Tyr Cys
                85                  90                  95

Thr Arg Asp Arg Pro Leu Phe His Trp Gly Gln Gly Thr Thr Leu Thr
                100                 105                 110

Val Ser Thr
        115
```

<210> SEQ ID NO 89
<211> LENGTH: 119
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 89

```
Glu Val Gln Leu Gln Glu Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
                20                  25                  30

Glu Ile His Trp Val Lys Glu Thr Pro Val Tyr Gly Leu Glu Trp Ile
        35                  40                  45

Gly Asp Ile His Pro Gly Ser Gly Thr Ala Asn Asn Gln Lys Phe
    50                  55                  60

Lys Gly Lys Ala Thr Leu Thr Ala Asp Lys Ser Ser Asn Thr Ala Tyr
65                  70                  75                  80
```

```
Met Glu Leu Ser Ser Leu Thr Ser Glu Asp Ser Ala Val Tyr Tyr Cys
                85                  90                  95

Thr Arg Ala Val Ser Gly Tyr Tyr Ala Met Asp Tyr Trp Gly Gln Gly
            100                 105                 110

Thr Ser Val Thr Val Ser Ser
        115
```

<210> SEQ ID NO 90
<211> LENGTH: 118
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 90

```
Glu Val Gln Leu Gln Glu Ser Gly Ala Glu Leu Val Arg Pro Gly Thr
1               5                   10                  15

Ser Val Lys Met Ser Cys Lys Ala Ala Gly Tyr Thr Phe Ser Asn Tyr
            20                  25                  30

Leu Ile Gly Trp Ile Lys Gln Arg Pro Gly His Gly Leu Glu Trp Ile
        35                  40                  45

Gly Asp Ile Tyr Pro Gly Asp Asn Asn Thr Tyr Asn Glu Lys Phe
    50                  55                  60

Arg Val Lys Ala Thr Leu Thr Ala Asp Thr Ser Ser Asn Thr Ala Tyr
65                  70                  75                  80

Met His Leu Thr Ser Leu Thr Ser Glu Asp Ser Ala Ile Tyr Tyr Cys
                85                  90                  95

Ala Gly Gly Thr Asp Tyr Asp Gly Phe Ala Asn Trp Gly Gln Gly Thr
            100                 105                 110

Leu Val Thr Val Ser Ala
        115
```

<210> SEQ ID NO 91
<211> LENGTH: 122
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 91

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Phe Leu Asn Trp Val Arg Gln Ala Pro Gly Gln Gly Leu Glu Trp Met
        35                  40                  45

Gly Arg Ile Asn Pro Tyr Asn Gly Asp Ser Phe Ile Asn Gln Asn Phe
    50                  55                  60

Arg Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Tyr Phe Ile Ala Tyr Phe Asp Tyr Trp
            100                 105                 110

Gly Ala Gly Thr Thr Val Thr Val Ser Ser
        115                 120
```

<210> SEQ ID NO 92

```
<211> LENGTH: 122
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Phe Leu Asn Trp Val Arg Gln Ala Pro Gly Gln Gly Leu Glu Trp Met
        35                  40                  45

Gly Arg Ile Asn Pro Tyr Asn Gly Asp Ser Phe Ile Asn Gln Asn Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Tyr Phe Ile Ala Tyr Phe Asp Tyr Trp
            100                 105                 110

Gly Ala Gly Thr Thr Val Thr Val Ser Ser
        115                 120

<210> SEQ ID NO 93
<211> LENGTH: 122
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 93

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Phe Leu Asn Trp Val Arg Gln Met Pro Gly Lys Gly Leu Glu Trp Met
        35                  40                  45

Gly Arg Ile Asn Pro Tyr Asn Gly Asp Ser Phe Ile Asn Gln Asn Phe
    50                  55                  60

Arg Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Gly Tyr Phe Ile Ala Tyr Phe Asp Tyr Trp
            100                 105                 110

Gly Ala Gly Thr Thr Val Thr Val Ser Ser
        115                 120

<210> SEQ ID NO 94
<211> LENGTH: 122
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 94

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Phe Thr Asp Tyr
            20                  25                  30

Phe Leu Asn Trp Val Arg Gln Ala Pro Gly Gln Gly Leu Glu Trp Met
        35                  40                  45

Gly Arg Ile Asn Pro Tyr Asn Gly Asp Ser Phe Ile Asn Gln Asn Phe
    50                  55                  60

Arg Asp Arg Val Thr Met Thr Val Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Tyr Phe Ile Ala Tyr Asp Tyr Trp
            100                 105                 110

Gly Ala Gly Thr Thr Val Thr Val Ser Ser
        115                 120
```

<210> SEQ ID NO 95
<211> LENGTH: 119
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Met
        35                  40                  45

Gly Asp Ile His Pro Gly Ser Gly Gly Thr Ala Asn Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Val Ser Gly Tyr Tyr Ala Met Asp Tyr Trp Gly Gln Gly
            100                 105                 110

Thr Leu Val Thr Val Ser Ser
        115
```

<210> SEQ ID NO 96
<211> LENGTH: 119
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 96

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Met
        35                  40                  45

Gly Asp Ile His Pro Gly Ser Gly Gly Thr Ala Asn Asn Gln Lys Phe
    50                  55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Ala Val Ser Gly Tyr Tyr Ala Met Asp Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Heavy Chain (VH) Variable Domain Sequence

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Ile His Trp Val Arg Gln Ala Pro Gly Gln Gly Leu Glu Trp Met
        35                  40                  45

Gly Asp Ile His Pro Gly Ser Gly Gly Thr Ala Asn Asn Gln Lys Phe
50                  55                  60

Lys Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Thr Arg Ala Val Ser Gly Tyr Tyr Ala Met Asp Tyr Trp Gly Gln Gly
            100                 105                 110

Thr Leu Val Thr Val Ser Ser
        115

<210> SEQ ID NO 98
<211> LENGTH: 213
<212> TYPE: PRT
<213> ORGANISM: Artificial Sequence
<220> FEATURE:
<223> OTHER INFORMATION: Light Chain (LC) Sequence

<400> SEQUENCE: 98

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Gly Val Asn Tyr Met
            20                  25                  30

Tyr Trp Tyr Gln Gln Lys Ser Asp Ala Ser Pro Lys Leu Leu Ile Tyr
        35                  40                  45

Tyr Thr Ser Ile Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
            85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
```

```
                  130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210
```

<210> SEQ ID NO 99
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 99

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Gly Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Thr Trp Pro Leu
                85                  90                  95

Thr Phe Gly Asp Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 100
<211> LENGTH: 215
<212> TYPE: PRT
<213> ORGANISM: Artificial Sequence
<220> FEATURE:
<223> OTHER INFORMATION: Light Chain (LC) Sequence

<400> SEQUENCE: 100

```
Glu Ile Val Leu Thr Gln Ser Pro Thr Thr Met Ala Ala Ser Pro Gly
1               5                   10                  15

Glu Lys Ile Thr Ile Ile Cys Ser Ala Ser Ser Ile Ile Gly Ser Asp
            20                  25                  30

Phe Leu His Trp Tyr Gln Gln Arg Pro Gly Phe Ser Pro Lys Phe Leu
        35                  40                  45

Ile Tyr Arg Thr Ser Ile Leu Ala Ser Gly Val Pro Thr Arg Phe Thr
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Gly Leu Pro
                85                  90                  95

Leu Thr Phe Gly Ser Gly Thr Lys Leu Glu Met Lys Arg Ala Asp Ala
            100                 105                 110

Ala Pro Thr Val Ser Ile Phe Pro Pro Ser Glu Gln Leu Thr Ser
            115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 101
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser His
            20                  25                  30

Leu Ser Trp Tyr Gln Gln Lys Pro Gly Lys Ala Pro Lys Leu Leu Ile
        35                  40                  45

Tyr Arg Ala Asn Arg Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 102
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser His
            20                  25                  30

Leu Ser Trp Tyr Gln Gln Lys Pro Gly Lys Ala Pro Lys Leu Leu Ile
        35                  40                  45

Tyr Arg Ala Asn Arg Leu Ala Thr Gly Val Pro Ser Arg Phe Ser Gly
    50                  55                  60

Ser Gly Ser Gly Thr Asp Phe Thr Phe Thr Ile Ser Ser Leu Glu Tyr
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 103
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 103

```
Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Ile Asn Ser His
            20                  25                  30

Leu Ser Trp Tyr Gln Lys Pro Gly Lys Ala Pro Lys Leu Leu Ile
        35                  40                  45

Tyr Arg Ala Asn Arg Leu Ala Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 104
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 104

Asp Ile Lys Met Thr Gln Ser Pro Ser Ser Met Tyr Ala Ser Leu Gly
1               5                   10                  15

Gln Arg Val Thr Ile Thr Cys Lys Ala Ser Gln Asp Ile Asn Ser His
            20                  25                  30

Leu Ser Trp Phe Gln Glu Lys Pro Gly Lys Ser Pro Lys Thr Leu Ile
        35                  40                  45

Tyr Arg Ala Asn Arg Leu Ala Asp Gly Val Pro Ser Arg Phe Ser Gly
50                  55                  60

Ser Gly Ser Gly Gln Asp Tyr Phe Leu Thr Ile Ser Ser Leu Glu Tyr
65                  70                  75                  80

Glu Asp Val Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 105
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asp Arg
            20                  25                  30

Val Ala Trp Tyr Gln Gln Lys Pro Gly Lys Ala Pro Lys Leu Leu Ile
            35                  40                  45

Tyr Gly Thr Ala Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Trp Thr Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 106
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asp Arg
```

```
             20                  25                  30
Val Ala Trp Tyr Gln Gln Lys Pro Gly Lys Ala Pro Lys Leu Leu Ile
         35                  40                  45

Tyr Gly Thr Ala Ser Leu Glu Thr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Thr Thr Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 107
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ala Ser Glu Asp Ile Tyr Asp Arg
             20                  25                  30

Val Ala Trp Tyr Gln Gln Lys Pro Gly Lys Ala Pro Lys Leu Leu Ile
         35                  40                  45

Tyr Gly Thr Ala Ser Leu Glu Thr Gly Val Leu Ser Arg Phe Ser Gly
     50                  55                  60

Ser Gly Ser Gly Thr Asp Phe Thr Leu Thr Ile Ser Ser Leu Gln Ala
 65                  70                  75                  80

Glu Asp Phe Ala Thr Tyr Tyr Cys Gln Gln Tyr Trp Thr Thr Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 108
<211> LENGTH: 214
<212> TYPE: PRT
<213> ORGANISM: Artificial Sequence
<220> FEATURE:
<223> OTHER INFORMATION: Light Chain (LC) Sequence

<400> SEQUENCE: 108

Asp Ile Gln Met Thr Gln Ser Ser Ser Phe Ser Gly Ser Leu Gly
1               5                   10                  15

Asp Arg Leu Thr Ile Asn Cys Lys Ala Ser Glu Asp Ile Tyr Asp Arg
            20                  25                  30

Val Ala Trp Tyr Gln Gln Lys Pro Gly Asn Ala Pro Arg Leu Leu Ile
        35                  40                  45

Ser Gly Thr Ala Ser Leu Glu Thr Gly Val Leu Ser Arg Phe Ser Gly
    50                  55                  60

Ser Gly Ser Gly Lys Asp Tyr Thr Leu Ser Ile Asn Gly Leu Gln Ala
65                  70                  75                  80

Glu Asp Val Ala Thr Tyr Tyr Cys Gln Gln Tyr Trp Thr Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 109
<211> LENGTH: 445
<212> TYPE: PRT
<213> ORGANISM: Artificial Sequence
<220> FEATURE:
<223> OTHER INFORMATION: Heavy Chain (HC) Sequence

<400> SEQUENCE: 109

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ser Phe Thr Lys Tyr
            20                  25                  30
```

-continued

```
Trp Ile Glu Trp Val Lys Gln Arg Pro Gly His Gly Leu Glu Trp Ile
         35                  40                  45
Gly Glu Ile Leu Pro Gly Ser Val Ile Thr Asn Tyr Asn Glu Lys Phe
 50                  55                  60
Lys Gly Lys Ala Thr Phe Thr Ala Asp Thr Ser Ser Asn Thr Val Tyr
 65                  70                  75                  80
Met Gln Leu Ser Ser Leu Thr Ser Glu Asp Ser Ala Val Tyr Tyr Cys
                 85                  90                  95
Thr Lys Trp Gly Leu Tyr Asp Ser Asp Gly Val Asp Tyr Trp Gly
                100                 105                 110
Gln Gly Thr Thr Leu Thr Val Ser Ser Ala Lys Thr Thr Pro Pro Ser
             115                 120                 125
Val Tyr Pro Leu Ala Pro Gly Ser Ala Ala Gln Thr Asn Ser Met Val
         130                 135                 140
Thr Leu Gly Cys Leu Val Lys Gly Tyr Phe Pro Glu Pro Val Thr Val
145                 150                 155                 160
Thr Trp Asn Ser Gly Ser Leu Ser Ser Gly Val His Thr Phe Pro Ala
                165                 170                 175
Val Leu Gln Ser Asp Leu Tyr Thr Leu Ser Ser Ser Val Thr Val Pro
            180                 185                 190
Ser Ser Thr Trp Pro Ser Glu Thr Val Thr Cys Asn Val Ala His Pro
        195                 200                 205
Ala Ser Ser Thr Lys Val Asp Lys Lys Ile Val Pro Arg Asp Cys Gly
    210                 215                 220
Cys Lys Pro Cys Ile Cys Thr Val Pro Glu Val Ser Ser Val Phe Ile
225                 230                 235                 240
Phe Pro Pro Lys Pro Lys Asp Val Leu Thr Ile Thr Leu Thr Pro Lys
                245                 250                 255
Val Thr Cys Val Val Val Asp Ile Ser Lys Asp Asp Pro Glu Val Gln
            260                 265                 270
Phe Ser Trp Phe Val Asp Asp Val Glu Val His Thr Ala Gln Thr Gln
        275                 280                 285
Pro Arg Glu Glu Gln Phe Asn Ser Thr Phe Arg Ser Val Ser Glu Leu
    290                 295                 300
Pro Ile Met His Gln Asp Trp Leu Asn Gly Lys Glu Phe Lys Cys Arg
305                 310                 315                 320
Val Asn Ser Ala Ala Phe Pro Ala Pro Ile Glu Lys Thr Ile Ser Lys
                325                 330                 335
Thr Lys Gly Arg Pro Lys Ala Pro Gln Val Tyr Thr Ile Pro Pro Pro
            340                 345                 350
Lys Glu Gln Met Ala Lys Asp Lys Val Ser Leu Thr Cys Met Ile Thr
        355                 360                 365
Asp Phe Phe Pro Glu Asp Ile Thr Val Glu Trp Gln Trp Asn Gly Gln
    370                 375                 380
Pro Ala Glu Asn Tyr Lys Asn Thr Gln Pro Ile Met Asp Thr Asp Gly
385                 390                 395                 400
Ser Tyr Phe Val Tyr Ser Lys Leu Asn Val Gln Lys Ser Asn Trp Glu
                405                 410                 415
Ala Gly Asn Thr Phe Thr Cys Ser Val Leu His Glu Gly Leu His Asn
            420                 425                 430
His His Thr Glu Lys Ser Leu Ser His Ser Pro Gly Lys
        435                 440                 445
```

-continued

```
<210> SEQ ID NO 110
<211> LENGTH: 443
<212> TYPE: PRT
<213> ORGANISM: Artificial Sequence
<220> FEATURE:
<223> OTHER INFORMATION: Heavy Chain (HC) Sequence

<400> SEQUENCE: 110
```

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Ser Phe Ser Gly Cys
            20                  25                  30

Thr Met Ser Trp Ile Arg Gln Thr Pro Glu Arg Arg Leu Glu Trp Val
        35                  40                  45

Ala Tyr Ile Ser Asn Gly Gly Asp Ile Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Lys Ser Glu Asp Thr Ala Met Tyr Tyr Cys
                85                  90                  95

Ala Arg Leu Asp Gly Tyr Tyr Tyr Ala Met Asp Phe Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala

```
              370                 375                 380
Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 111
<211> LENGTH: 445
<212> TYPE: PRT
<213> ORGANISM: Artificial Sequence
<220> FEATURE:
<223> OTHER INFORMATION: Heavy Chain (HC) Sequence

<400> SEQUENCE: 111

Glu Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Pro Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Phe Cys
                85                  90                  95

Ala Arg Trp Asp Tyr Phe Asn Ser Ala Ser Gly Phe Ala Phe Trp Gly
                100                 105                 110

Gln Gly Thr Leu Val Thr Val Ser Ala Ala Lys Thr Thr Pro Pro Ser
            115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
```

```
                290             295             300
Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
                370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
                435                 440                 445

<210> SEQ ID NO 112
<211> LENGTH: 449
<212> TYPE: PRT
<213> ORGANISM: Artificial Sequence
<220> FEATURE:
<223> OTHER INFORMATION: Heavy Chain (HC) Sequence

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Phe Leu Asn Trp Val Arg Gln Ala Pro Gly Gln Gly Leu Glu Trp Met
                35                  40                  45

Gly Arg Ile Asn Pro Tyr Asn Gly Asp Ser Phe Ile Asn Gln Asn Phe
50                  55                  60

Arg Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Tyr Phe Ile Ala Tyr Phe Asp Tyr Trp
                100                 105                 110

Gly Ala Gly Thr Thr Val Thr Val Ser Ser Ala Ser Thr Lys Gly Pro
                115                 120                 125

Ser Val Phe Pro Leu Ala Pro Cys Ser Arg Ser Thr Ser Glu Ser Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
```

```
                210                 215                 220
Gly Pro Pro Cys Pro Pro Cys Pro Ala Pro Glu Phe Leu Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 113
<211> LENGTH: 449
<212> TYPE: PRT
<213> ORGANISM: Artificial Sequence
<220> FEATURE:
<223> OTHER INFORMATION: Heavy Chain (HC) Sequence

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Phe Leu Asn Trp Val Arg Gln Ala Pro Gly Gln Gly Leu Glu Trp Met
            35                  40                  45

Gly Arg Ile Asn Pro Tyr Asn Gly Asp Ser Phe Ile Asn Gln Asn Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Tyr Phe Ile Ala Tyr Phe Asp Tyr Trp
                100                 105                 110

Gly Ala Gly Thr Thr Val Thr Val Ser Ser Ala Ser Thr Lys Gly Pro
            115                 120                 125
```

```
Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 114
<211> LENGTH: 449
<212> TYPE: PRT
<213> ORGANISM: Artificial Sequence
<220> FEATURE:
<223> OTHER INFORMATION: Heavy Chain (HC) Sequence

<400> SEQUENCE: 114

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30
```

```
Phe Leu Asn Trp Val Arg Gln Met Pro Gly Lys Gly Leu Glu Trp Met
         35                  40                  45
Gly Arg Ile Asn Pro Tyr Asn Gly Asp Ser Phe Ile Asn Gln Asn Phe
 50                  55                  60
Arg Asp Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gly Gly Tyr Asp Gly Tyr Phe Ile Ala Tyr Phe Asp Tyr Trp
             100                 105                 110
Gly Ala Gly Thr Thr Val Thr Val Ser Ser Ala Ser Thr Lys Gly Pro
         115                 120                 125
Ser Val Phe Pro Leu Ala Pro Cys Ser Arg Ser Thr Ser Glu Ser Thr
     130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
             180                 185                 190
Val Pro Ser Ser Ser Leu Gly Thr Lys Thr Tyr Thr Cys Asn Val Asp
         195                 200                 205
His Lys Pro Ser Asn Thr Lys Val Asp Lys Arg Val Glu Ser Lys Tyr
     210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser Gln Glu Asp
             260                 265                 270
Pro Glu Val Gln Phe Asn Trp Tyr Val Asp Gly Val Glu Val His Asn
         275                 280                 285
Ala Lys Thr Lys Pro Arg Glu Glu Gln Phe Asn Ser Thr Tyr Arg Val
     290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                 325                 330                 335
Thr Ile Ser Lys Ala Lys Gly Gln Pro Arg Glu Pro Gln Val Tyr Thr
             340                 345                 350
Leu Pro Pro Ser Gln Glu Glu Met Thr Lys Asn Gln Val Ser Leu Thr
         355                 360                 365
Cys Leu Val Lys Gly Phe Tyr Pro Ser Asp Ile Ala Val Glu Trp Glu
     370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                 405                 410                 415
Ser Arg Trp Gln Glu Gly Asn Val Phe Ser Cys Ser Val Met His Glu
             420                 425                 430
Ala Leu His Asn His Tyr Thr Gln Lys Ser Leu Ser Leu Ser Leu Gly
         435                 440                 445
Lys
```

<210> SEQ ID NO 115
<211> LENGTH: 449
<212> TYPE: PRT
<213> ORGANISM: Artificial Sequence
<220> FEATURE:
<223> OTHER INFORMATION: Heavy Chain (HC) Sequence

<400> SEQUENCE: 115

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Thr | Asp | Tyr |
| | | | 20 | | | | | 25 | | | | | 30 | | |
| Phe | Leu | Asn | Trp | Val | Arg | Gln | Ala | Pro | Gly | Gln | Gly | Leu | Glu | Trp | Met |
| | | 35 | | | | | 40 | | | | | 45 | | | |
| Gly | Arg | Ile | Asn | Pro | Tyr | Asn | Gly | Asp | Ser | Phe | Ile | Asn | Gln | Asn | Phe |
| 50 | | | | | 55 | | | | | 60 | | | | | |
| Arg | Asp | Arg | Val | Thr | Met | Thr | Val | Asp | Thr | Ser | Thr | Ser | Thr | Val | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Gly | Tyr | Asp | Gly | Tyr | Phe | Ile | Ala | Tyr | Phe | Asp | Tyr | Trp |
| | | | 100 | | | | | 105 | | | | | 110 | | |
| Gly | Ala | Gly | Thr | Thr | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Cys | Ser | Arg | Ser | Thr | Ser | Glu | Ser | Thr |
| 130 | | | | | 135 | | | | | 140 | | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Lys | Thr | Tyr | Thr | Cys | Asn | Val | Asp |
| | | 195 | | | | | 200 | | | | | 205 | | | |
| His | Lys | Pro | Ser | Asn | Thr | Lys | Val | Asp | Lys | Arg | Val | Glu | Ser | Lys | Tyr |
| 210 | | | | | 215 | | | | | 220 | | | | | |
| Gly | Pro | Pro | Cys | Pro | Pro | Cys | Pro | Ala | Pro | Glu | Phe | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | Gln | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Tyr | Arg | Val |
| 290 | | | | | 295 | | | | | 300 | | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ser | Ser | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Gln | Glu | Glu | Met | Thr | Lys | Asn | Gln | Val | Ser | Leu | Thr |
| | | 355 | | | | | 360 | | | | | 365 | | | |

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 116
<211> LENGTH: 449
<212> TYPE: PRT
<213> ORGANISM: Artificial Sequence
<220> FEATURE:
<223> OTHER INFORMATION: Heavy Chain (HC) Sequence

<400> SEQUENCE: 116

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Asp Tyr
            20                  25                  30

Phe Leu Asn Trp Val Lys Gln Ser His Gly Lys Ser Leu Glu Trp Ile
        35                  40                  45

Gly Arg Ile Asn Pro Tyr Asn Gly Asp Ser Phe Ile Asn Gln Asn Phe
50                  55                  60

Arg Asp Lys Ala Thr Leu Thr Val Asp Lys Ser Ser Thr Thr Ala His
65                  70                  75                  80

Met Asp Leu Leu Ser Leu Thr Ser Glu Asp Ser Ala Ile Tyr Tyr Cys
                85                  90                  95

Gly Arg Gly Gly Tyr Asp Gly Tyr Phe Ile Ala Tyr Phe Asp Tyr Trp
            100                 105                 110

Gly Gln Gly Ser Leu Val Thr Val Ser Ala Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

-continued

```
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Lys

<210> SEQ ID NO 117
<211> LENGTH: 446
<212> TYPE: PRT
<213> ORGANISM: Artificial Sequence
<220> FEATURE:
<223> OTHER INFORMATION: Heavy Chain (HC) Sequence

<400> SEQUENCE: 117

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Glu Ile His Trp Val Arg Gln Ala Pro Gly Gln Gly Leu Glu Trp Met
        35                  40                  45
Gly Asp Ile His Pro Gly Ser Gly Gly Thr Ala Asn Asn Gln Lys Phe
    50                  55                  60
Lys Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ala Val Ser Gly Tyr Tyr Ala Met Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
```

```
                180             185             190
Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
            210             215             220

Cys Pro Pro Cys Pro Ala Pro Glu Phe Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Phe Asn Ser Thr Tyr Arg Val Val Ser Val
            290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
            370             375             380

Gln Pro Glu Asn Asn Tyr Lys Thr Thr Pro Pro Val Leu Asp Ser Asp
385             390             395             400

Gly Ser Phe Phe Leu Tyr Ser Arg Leu Thr Val Asp Lys Ser Arg Trp
            405             410             415

Gln Glu Gly Asn Val Phe Ser Cys Ser Val Met His Glu Ala Leu His
            420             425             430

Asn His Tyr Thr Gln Lys Ser Leu Ser Leu Ser Leu Gly Lys
            435             440             445

<210> SEQ ID NO 118
<211> LENGTH: 446
<212> TYPE: PRT
<213> ORGANISM: Artificial Sequence
<220> FEATURE:
<223> OTHER INFORMATION: Heavy Chain (HC) Sequence

<400> SEQUENCE: 118

Gln Val Gln Leu Val Gln Ser Gly Ala Glu Val Lys Lys Pro Gly Ser
1               5               10              15

Ser Val Lys Val Ser Cys Lys Ala Ser Gly Tyr Thr Phe Thr Asp Tyr
            20              25              30

Glu Ile His Trp Val Arg Gln Ala Pro Gly Gln Gly Leu Glu Trp Met
            35              40              45

Gly Asp Ile His Pro Gly Ser Gly Gly Thr Ala Asn Asn Gln Lys Phe
        50              55              60

Lys Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Ala Val Ser Gly Tyr Tyr Ala Met Asp Tyr Trp Gly Gln Gly
```

```
            100                 105                 110
Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 119
<211> LENGTH: 446
<212> TYPE: PRT
<213> ORGANISM: Artificial Sequence
<220> FEATURE:
<223> OTHER INFORMATION: Heavy Chain (HC) Sequence

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
            20                  25                  30
Glu Ile His Trp Val Arg Gln Ala Pro Gly Gln Gly Leu Glu Trp Met
         35                  40                  45
Gly Asp Ile His Pro Gly Ser Gly Thr Ala Asn Asn Gln Lys Phe
 50                  55                  60
Lys Gly Arg Val Thr Met Thr Ala Asp Thr Ser Thr Thr Val Tyr
 65                  70                  75                  80
Met Glu Leu Ser Ser Leu Arg Ser Glu Asp Thr Ala Val Tyr Tyr Cys
                 85                  90                  95
Thr Arg Ala Val Ser Gly Tyr Tyr Ala Met Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
 210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
 290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445
```

<210> SEQ ID NO 120
<211> LENGTH: 446
<212> TYPE: PRT
<213> ORGANISM: Artificial Sequence
<220> FEATURE:
<223> OTHER INFORMATION: Heavy Chain (HC) Sequence

<400> SEQUENCE: 120

Glu Val Gln Leu Gln Glu Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
            20                  25                  30

Glu Ile His Trp Val Lys Glu Thr Pro Val Tyr Gly Leu Glu Trp Ile
        35                  40                  45

Gly Asp Ile His Pro Gly Ser Gly Gly Thr Ala Asn Asn Gln Lys Phe
    50                  55                  60

Lys Gly Lys Ala Thr Leu Thr Ala Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Thr Arg Ala Val Ser Gly Tyr Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 121
<211> LENGTH: 473
<212> TYPE: PRT
<213> ORGANISM: Artificial Sequence
<220> FEATURE:
<223> OTHER INFORMATION: SIRP alpha sequence

<400> SEQUENCE: 121

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
                165                 170                 175

Ser Ile His Ser Thr Ala Lys Val Val Leu Thr Arg Glu Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser Glu Thr Ile Arg Val Pro Pro Thr
    210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
                245                 250                 255

Leu Glu Asn Gly Asn Val Ser Arg Thr Glu Thr Ala Ser Thr Val Thr
            260                 265                 270

Glu Asn Lys Asp Gly Thr Tyr Asn Trp Met Ser Trp Leu Leu Val Asn
        275                 280                 285
```

```
Val Ser Ala His Arg Asp Asp Val Lys Leu Thr Cys Gln Val Glu His
    290                 295                 300

Asp Gly Gln Pro Ala Val Ser Lys Ser His Asp Leu Lys Val Ser Ala
305                 310                 315                 320

His Pro Lys Glu Gln Gly Ser Asn Thr Ala Ala Glu Asn Thr Gly Ser
                325                 330                 335

Asn Glu Arg Asn Ile Tyr Ile Val Val Gly Val Val Cys Thr Leu Leu
            340                 345                 350

Val Ala Leu Leu Met Ala Ala Leu Tyr Leu Val Arg Ile Arg Gln Lys
        355                 360                 365

Lys Ala Gln Gly Ser Thr Ser Ser Thr Arg Leu His Glu Pro Glu Lys
    370                 375                 380

Asn Ala Arg Glu Ile Thr Gln Asp Thr Asn Asp Ile Thr Tyr Ala Asp
385                 390                 395                 400

Leu Asn Leu Pro Lys Gly Lys Lys Pro Ala Pro Gln Ala Ala Glu Pro
                405                 410                 415

Asn Asn His Thr Glu Tyr Ala Ser Ile Gln Thr Ser Pro Gln Pro Ala
            420                 425                 430

Ser Glu Asp Thr Leu Thr Tyr Ala Asp Leu Asp Met Val His Leu Asn
        435                 440                 445

Arg Thr Pro Lys Gln Pro Ala Pro Lys Pro Glu Pro Ser Phe Ser Glu
    450                 455                 460

Tyr Ala Ser Val Gln Val Pro Arg Lys
465                 470

<210> SEQ ID NO 122
<211> LENGTH: 359
<212> TYPE: PRT
<213> ORGANISM: Artificial Sequence
<220> FEATURE:
<223> OTHER INFORMATION: SIRP gamma sequence

<400> SEQUENCE: 122

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser Ala Pro Val Val Leu Gly Pro Ala Ala
        115                 120                 125

Arg Thr Thr Pro Glu His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175
```

```
Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
        195                 200                 205

Pro Leu Arg Gly Thr Ala Asn Leu Ser Glu Ala Ile Arg Val Pro Pro
    210                 215                 220

Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
                245                 250                 255

Trp Ser Glu Asn Gly Asn Val Cys Gln Arg Glu Thr Ala Ser Thr Leu
            260                 265                 270

Thr Glu Asn Lys Asp Gly Thr Tyr Asn Trp Thr Ser Trp Phe Leu Val
        275                 280                 285

Asn Ile Ser Asp Gln Arg Asp Asp Val Val Leu Thr Cys Gln Val Lys
    290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro Gly Pro Ala Ser
                325                 330                 335

Ser Leu Thr Ala Leu Leu Leu Ile Ala Val Leu Leu Gly Pro Ile Tyr
            340                 345                 350

Val Pro Trp Lys Gln Lys Thr
        355

<210> SEQ ID NO 123
<211> LENGTH: 330
<212> TYPE: PRT
<213> ORGANISM: Artificial Sequence
<220> FEATURE:
<223> OTHER INFORMATION: Human Fc IgG1 Sequence

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 330
<212> TYPE: PRT
<213> ORGANISM: Artificial Sequence
<220> FEATURE:
<223> OTHER INFORMATION: Human Fc IgG1-N297Q Sequence

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 125
<211> LENGTH: 326
<212> TYPE: PRT
<213> ORGANISM: Artificial Sequence
<220> FEATURE:
<223> OTHER INFORMATION: Human Fc-IgG2 Sequence

<400> SEQUENCE: 125

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 126
<211> LENGTH: 377
<212> TYPE: PRT
<213> ORGANISM: Artificial Sequence
<220> FEATURE:
<223> OTHER INFORMATION: Human Fc-IgG3 Sequence

<400> SEQUENCE: 126

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

```
Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 127
<211> LENGTH: 326
<212> TYPE: PRT
<213> ORGANISM: Artificial Sequence
<220> FEATURE:
<223> OTHER INFORMATION: Human Fc-IgG4 Sequence

<400> SEQUENCE: 127

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 128
<211> LENGTH: 326
<212> TYPE: PRT
<213> ORGANISM: Artificial Sequence
<220> FEATURE:
<223> OTHER INFORMATION: Human Fc-IgG4 S228P Sequence

<400> SEQUENCE: 128

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 129
<211> LENGTH: 327
<212> TYPE: PRT
<213> ORGANISM: Artificial Sequence
<220> FEATURE:
<223> OTHER INFORMATION: Human Fc-IgG4 PE Sequence

<400> SEQUENCE: 129

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
                325

<210> SEQ ID NO 130
<211> LENGTH: 326
<212> TYPE: PRT
<213> ORGANISM: Artificial Sequence
<220> FEATURE:
<223> OTHER INFORMATION: Human Fc-IgG4 PE' Sequence

<400> SEQUENCE: 130

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 131
```

```
<211> LENGTH: 107
<212> TYPE: PRT
<213> ORGANISM: Artificial Sequence
<220> FEATURE:
<223> OTHER INFORMATION: Human kappa LC Sequence

<400> SEQUENCE: 131

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```